United States Patent
Ma et al.

(10) Patent No.: US 12,378,329 B2
(45) Date of Patent: Aug. 5, 2025

(54) ZWITTERIONICALLY MODIFIED POLYMERS AND HYDROGELS

(71) Applicant: Cornell University, Ithaca, NY (US)

(72) Inventors: Minglin Ma, Ithaca, NY (US); Qingsheng Liu, Ithaca, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 0 days.

(21) Appl. No.: 18/122,416

(22) Filed: Mar. 16, 2023

(65) Prior Publication Data

US 2024/0018276 A1   Jan. 18, 2024

Related U.S. Application Data

(62) Division of application No. 16/480,996, filed as application No. PCT/US2018/015613 on Jan. 27, 2018, now Pat. No. 11,634,512.

(60) Provisional application No. 62/451,629, filed on Jan. 27, 2017.

(51) Int. Cl.
| | |
|---|---|
| A61K 9/00 | (2006.01) |
| A61K 9/06 | (2006.01) |
| A61K 9/48 | (2006.01) |
| A61K 47/34 | (2017.01) |
| C08B 37/00 | (2006.01) |
| C08F 116/06 | (2006.01) |

(52) U.S. Cl.
CPC ........ *C08B 37/0084* (2013.01); *A61K 9/0024* (2013.01); *A61K 9/06* (2013.01); *A61K 9/4866* (2013.01); *A61K 47/34* (2013.01); *C08F 116/06* (2013.01)

(58) Field of Classification Search
None
See application file for complete search history.

(56) References Cited

U.S. PATENT DOCUMENTS

| | | | |
|---|---|---|---|
| 2,744,130 | A | 5/1956 | Winberg et al. |
| 6,642,363 | B1 | 11/2003 | Mooney et al. |
| 9,394,435 | B2 | 7/2016 | Jiang et al. |
| 9,422,373 | B2 | 8/2016 | Vegas et al. |
| 11,634,512 | B2 | 4/2023 | Ma et al. |
| 2004/0208883 | A1 | 10/2004 | Davis et al. |
| 2012/0308650 | A1 | 12/2012 | Vegas et al. |
| 2016/0030360 | A1 | 2/2016 | Vegas et al. |
| 2016/0297761 | A1* | 10/2016 | Bhavar .................. A61P 11/02 |
| 2016/0324793 | A1 | 11/2016 | Vegas et al. |
| 2017/0009069 | A1 | 1/2017 | Jiang et al. |
| 2017/0239397 | A1 | 8/2017 | Vegas et al. |
| 2017/0355799 | A1 | 12/2017 | Veiseh et al. |

FOREIGN PATENT DOCUMENTS

| | | |
|---|---|---|
| JP | H05148288 A | 6/1993 |
| JP | 2009514807 A | 4/2009 |
| JP | 2012031400 A | 2/2012 |
| RU | 2586931 C2 | 6/2016 |

(Continued)

OTHER PUBLICATIONS

Translation of the Office Action for Korean Patent Application No. 10-2019-7023740 (Dec. 25, 2022).

(Continued)

*Primary Examiner* — Melissa S Mercier
(74) *Attorney, Agent, or Firm* — Troutman Pepper Locke LLP (Rochester)

(57) ABSTRACT

The present invention is directed to a polymer of Formula (IV):

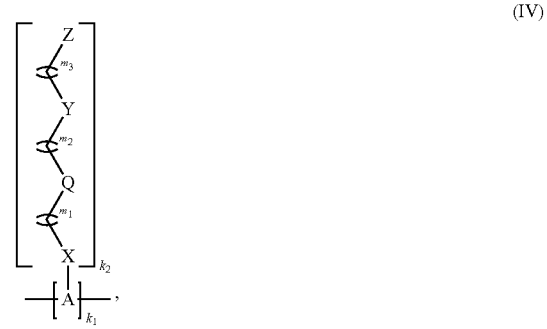

wherein A, X, Q, Y, Z, $m_1$, $m_2$, $m_3$, $k_1$, and $k_2$ are as described herein and wherein the monomer units of the polymer are the same or different. The present invention also relates to a monomer of Formula (III):

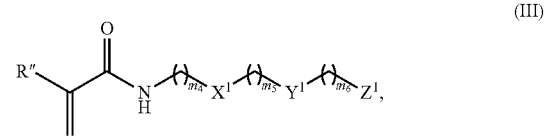

wherein R", $X^1$, $Y^1$, $Z^1$, $m_4$, $m_5$, and $m_6$ are as described herein, and a polymeric network comprising two or more monomers of Formula (III). The present invention also relates to a hydrogel comprising any of the polymers and monomers described herein, a capsule comprising the hydrogel, and a method of delivering a therapeutic agent to a subject using the capsule.

18 Claims, 26 Drawing Sheets

(56) References Cited

FOREIGN PATENT DOCUMENTS

| WO | 99/04824 A1 | 2/1999 |
|---|---|---|
| WO | 2014/194268 A1 | 12/2014 |
| WO | 2015/057645 A1 | 4/2015 |
| WO | 2016/138528 A1 | 9/2016 |
| WO | 2017/218207 A1 | 12/2017 |
| WO | 2017/218507 A1 | 12/2017 |

OTHER PUBLICATIONS

Communication Pursuant to Article 94(3) EPC for Europe Patent Application No. 18744703.2 (Sep. 21, 2022).
Translation of the Office Action for Chinese Patent Application No. 201880017027.8 (Jun. 13, 2022).
Informal Translation of the Office Action for Brazil Patent Application No. BR112019015141-9 (Jul. 20, 2022).
Translation of the Office Action for Mexican Patent Application No. MX/a/2019/008388 (Jan. 20, 2022) (redacted).
Translation of the Notice of Reasons for Rejection for Japanese Patent Application No. 2019-540665 (Dec. 20, 2021).
Translation of the Office Action for Israel Patent Application No. 267991 (Jul. 22, 2021).
Translation of the Office Action for Mexican Patent Application No. MX/a/2019/008388 (Jun. 3, 2021).
Translation of the Office Action for Russian Patent Application No. 2019126801 (May 24, 2021).
Examination Report for Singapore Patent Application No. 11201906804U (Dec. 14, 2020).
Kirzhanova et al., "Mikro—i Nanochastitsy iz Al'ginata i Khitozana Dlya Transmukozal'noy Dostavki Belka [Alginate/Chitosan Micro- and Nanoparticles for Protein Mucosal Delivery]," Vestn. Mosk. Un-ta, Ser. 2, Khimiya 57(2):103-111 (2016) (Article in Russian, English Title and Abstract at p. 111).
Translation of the Office Action for Mexican Patent Application No. MX/a/2019/008388 (Sep. 29, 2020).
First Written Opinion for Singapore Patent Application No. 11201906804U (Jun. 23, 2020).
Extended European Search Report for Europe Patent Application No. 18744703.2 (Sep. 17, 2020).
Ning et al., "Characteristics of Zwitterionic Sulfobetaine Acrylamide Polymer and the Hydrogels Prepared by Free-Radical Polymerization and Effects of Physical and Chemical Crosslinks on the UCST," Reactive and Functional Polymers 73:969-978 (2013).
Wang et al., "Ionic Starch-Based Hydrogels for the Prevention of Nonspecific Protein Adsorption," Carbohydrate Polymers, 117:384-391 (2015).
Wang et al., "Preparation and Characterization of Protein Resistant Zwitterionic Starches: The Effect of Substitution Degrees," Starch 67:1-10 (2015).
International Preliminary Report on Patentability for corresponding Application No. PCT/US2018/015613 (mailed Aug. 8, 2019).
Suzuki et al., "Ammonia or Ammonium Ion as Substrate for Oxidation by Nitrosomonas europaea Cells and Extracts," Journal of Bacteriology 120(1):556-558 (1974).
Laschewsky, André, "Structures and Synthesis of Zwitterionic Polymers," Polymers 6:1544-1601 (2014).
Schanté et al., "Chemical Modifications of Hyaluronic Acid for the Synthesis of Derivatives for a Broad Range of Biomedical Applications," Carbohydrate Polymers 85:469-489 (2011).
Pubchem CID for beta-D-Mannuronate (2009) Retreived from internet at https://pubchem.ncbi.nlm.nih.gov/compound.
Bayramgil, Nursel Pekel, "Synthesis, Characterization and Drug Release Behavior of Poly (1-vinyl 1,2,4-triazole) Hydrogels Prepared by Gamma Irradiation," Colloids and Surfaces B: Biointerfaces 97:182-189 (2012).
Ye et al., "Physical Cross-Linking Starch-Based Switterionic Hydrogel Exhibiting Excellent Biocompatability, Protein Resistance, and Biodegradability," Applied Materials & Interfaces 8:15710-15723 (2016).
Martini et al., "Charged Triazole Cross-Linkers for Hyaluronan-Based Hybrid Hydrogels," Materials 9:1-11 (2016).
Mishra et al., "Triazole-Containing Hydrogels for Time-Dependent Sustained Drug Release," Macromolecular Rapid Communication 35:442-446 (2014).
Zhang et al., "Zwitterionic Hydrogels Implanted in Mice Resist the Foreign-Body Reaction," Nature Biotechnology 31(6):553-557 (2013).
Vegas et al., "Combinatorial Hydrogel Library Enables Identification of Materials That Mitigate the Foreign Body Response in Primates," Nature Biotechnology 34(3):345-352 and addendum pp. 1-6 (2016).
PCT International Search Report and Written Opinion for corresponding PCT/US2018/015613, mailed May 4, 2018.
Office Action for Canadian Patent Application No. 3,051,142 (Dated Apr. 29, 2024).
Translation of the Second Office Action for Chinese Patent Application No. 201880017027.8 (Mar. 22, 2023).
Translation of the Notice of Preliminary Rejection for Korean Patent Application No. 10-2019-7023740 (Dec. 25, 2022).
Examination Report for Australia Patent Application No. 2018212895 (Mar. 7, 2023).

* cited by examiner (a)

(b)

10a (A)

(B)

ZWITTERIONICALLY MODIFIED POLYMERS AND HYDROGELS

This application is a divisional of U.S. patent application Ser. No. 16/480,996, filed Jul. 25, 2019, which is a national stage application under 35 U.S.C. § 371 of International Application No. PCT/US2018/015613, filed Jan. 27, 2018, which claims the benefit of U.S. Provisional Patent Application Ser. No. 62/451,629, filed Jan. 27, 2017, which is hereby incorporated by reference in its entirety.

FIELD OF THE INVENTION

The present invention relates to a zwitterionic monomers, polymers, and hydrogels, and their use to coat and/or encapsulate biological materials.

BACKGROUND OF THE INVENTION

Although many advanced therapeutic cell treatments have been developed recently, type 1 diabetes (T1D) is still a global epidemic affecting over millions of people worldwide. Pancreatic islet transplantation has been considered as an alternative and promising approach for the treatment of T1D. However, islet transportation in the clinic is limited by two major hurdles: shortage of donor islets and long-term immuno-suppression. Recently, human stem cell-derived beta cells have been developed, providing a pathway to produce an unlimited supply of insulin-producing cells. Therefore, there is a critical need for development of novel materials or medical devices that encapsulate islets to protect them from the host immune response effectively.

The performance of implanted biomaterials is often impeded by the foreign body response (FBR), which leads to the formation of a dense collagenous capsule and then the failure of the medical device. Nonspecific protein adsorption on the implanted material is considered the first step of the foreign body response. Incorporation of an antifouling material or a surface that highly resists protein adsorption and cell attachment is expected to suppress FBR and the subsequent formation of a fibrotic capsule. Recently, the use of zwitterionic polymers, bearing zwitterion of carboxybetaine, sulfobetaine, and phosphorycholine, have drawn much attention due to the ultra-low-fouling properties of these polymers (Jiang et al., "Ultralow-Fouling, Functionalizable, and Hydrolyzable Zwitterionic Materials and Their Derivatives for Biological Applications," *Advanced Materials* 22(9): 920-932 (2010)). For example, zwitterionic poly(carboxybetaine methacrylate) (PCBMA) has shown to resist the formation of a capsule for at least 3 months after subcutaneous implantation in mice (Zhang et al., "Zwitterionic Hydrogels Implanted in Mice Resist the Foreign-Body Reaction," *Nature Biotechnology* 31(6):553-556 (2013)). However, the harsh conditions associated with gelation of the zwitterionic materials, e.g., UV irradiation and free radical generation, can cause much harm to the encapsulated cell, limiting the applications of these materials for cell encapsulation.

The naturally derived material, alginate, has also shown potential for use in numerous applications including tissue regeneration, drug delivery and cell encapsulation, due in a large part to its mild gelation and low toxicity (Drury et al., "The Tensile Properties of Alginate Hydrogels," *Biomaterials* 25(16):3187-3199 (2004)). However, alginate elicits a fibrotic response which is worsened with the encapsulation of cells or xenogeneic donor tissue. The fibrotic tissue on the alginate surface cuts off the diffusion of nutrients and oxygen to the encapsulated cell, causing cell necrosis. Thus there is a need in the art for a polymeric material that does not elicit the FBR and promotes the health of the encapsulated cells or tissue.

The present invention is directed to overcoming these and other deficiencies in the art.

SUMMARY OF THE INVENTION

A first aspect of the present invention is directed to a monomer of Formula (I):

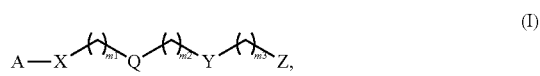

wherein

A is selected from a saccharide containing unit and a polyvinyl alcohol containing unit;

X is selected from the group consisting of O, NH, NR', C(O), and $C_{1-20}$ alkylene, wherein $C_{1-20}$ alkylene is optionally substituted from 1 to 20 times with a substituent selected independently at each occurrence thereof from the group consisting of OH, halogen, cyano, —$CF_3$, and $C_{1-6}$ alkoxy.

Q is absent or is a linker;

Y is selected from the group consisting of

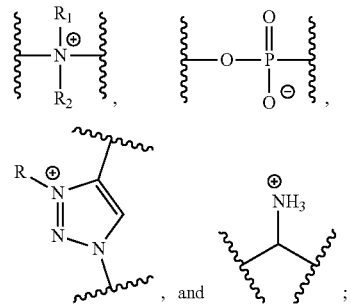

Z is selected from the group consisting of

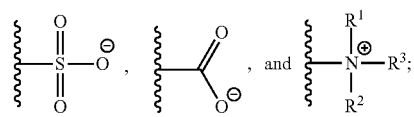

$m_1$ is 0 to 50;

$m_2$ is 0 to 50;

$m_3$ is 0 to 50;

R is $C_{1-20}$ alkyl;

R' is —C(O)—$C_{1-6}$ alkene;

$R^1$ is $C_{1-20}$ alkyl;

$R^2$ is $C_{1-20}$ alkyl; and $R^3$ is $C_{1-20}$ alkyl.

Another aspect of the present invention relates to a polymer of Formula (IV):

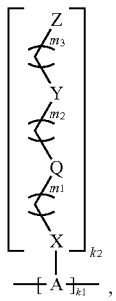
(IV)

wherein
A is independently selected from a saccharide containing unity and a polyvinyl alcohol containing unit for each monomer unit of the polymer;
X is selected from the group consisting of O, NH, NR', C(O), and $C_{1-20}$ alkylene, wherein $C_{1-20}$ alkylene is optionally substituted from 1 to 20 times with a substituent selected independently at each occurrence thereof from the group consisting of OH, halogen, cyano, —$CF_3$, and $C_{1-6}$ alkoxy
Q is absent or is a linker;
Y is selected from the group consisting of

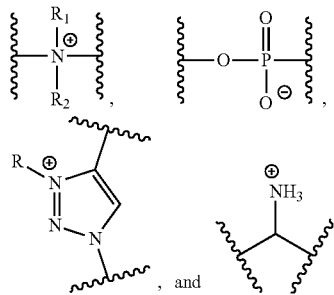

Z is selected from the group consisting of

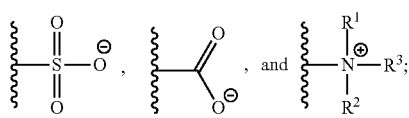

$m_1$ is 0 to 50;
$m_2$ is 0 to 50;
$m_3$ is 0 to 50;
R is $C_{1-20}$ alkyl;
R' is —C(O)—$C_{1-6}$ alkene;
$R^1$ is $C_{1-20}$ alkyl;
$R^2$ is $C_{1-20}$ alkyl;
$R^3$ is $C_{1-20}$ alkyl,
$k_1$ is any integer; and
$k_2$ is independently selected for each monomer unit from 0 or 1, with the proviso that at least one $k_2$ is 1;
wherein the monomer units of the polymer are the same or different.

Another aspect of the present invention relates to a polymer, wherein said polymer comprises one or more monomers of Formula (I):

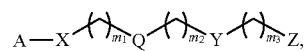
(I)

and further comprises
one or more monomers of Formula (II):

$$A\text{-}L^1\text{-}L^2\text{-}L^3\text{-}R^4 \quad (II)$$

wherein
$L^1$ is selected from the group consisting of O, NH, NR', C(O), and $C_{1-20}$ alkylene, wherein $C_{1-20}$ alkylene is optionally substituted from 1 to 20 times with a substituent selected independently at each occurrence thereof from the group consisting of OH, halogen, cyano, —$CF_3$, and $C_{1-6}$ alkoxy;
$L^2$ is absent or is $C_{1-20}$ alkylene, wherein $C_{1-20}$ alkylene is optionally substituted from 1 to 20 times with a substituent selected independently at each occurrence thereof from the group consisting of OH, halogen, cyano, —$CF_3$, and $C_{1-6}$ alkoxy;
$L^3$ is selected from the group consisting of $C_{1-20}$ alkylene, $C_{1-20}$ alkenylene, $C_{3-12}$ cycloalkenylene, and arylene, wherein arylene is optionally substituted from 1 to 3 times with a substituent selected independently at each occurrence thereof from the group consisting of heteroarylene and heterocyclylene; and
$R^4$ is selected from the group consisting of H, SH, $N_3$, $C_{1-6}$ alkyl, $C_{2-20}$ alkenyl, $C_{2-20}$ alkynyl, $C_{3-12}$ cycloalkenyl, $C_{3-12}$ cycloalkynyl, heteroaryl, and heterocyclyl, wherein $C_{1-6}$ alkyl, $C_{2-20}$ alkenyl, $C_{2-20}$ alkynyl, $C_{3-12}$ cycloalkenyl, $C_{3-12}$ cycloalkynyl, heteroaryl, and heterocyclyl is optionally substituted from 1 to 3 times with a substituent selected independently at each occurrence thereof from the group consisting of H, OH, halogen, cyano, —$CF_3$, and $C_{1-6}$ alkoxy.

Another aspect of the present invention relates to a monomer of Formula (III):

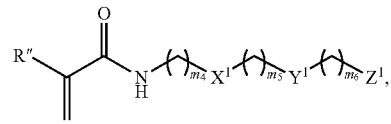
(III)

wherein
$X^1$ is absent or is

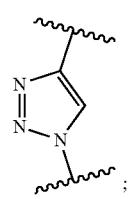 [SMILES: *c1cn(*)nn1]

$Y^1$ is

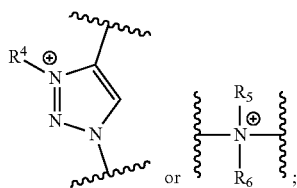

$Z^1$ is

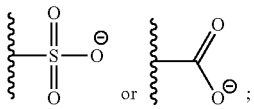

$m_4$ is 1 to 50;
$m_5$ is 0 to 10;
$m_6$ is 1 to 50;
R" is H or $C_{1-6}$ alkyl;
$R^4$ is $C_{1-20}$ alkyl;
$R^5$ is $C_{1-20}$ alkyl; and
$R^6$ is $C_{1-20}$ alkyl,
with the proviso that when $X^1$ is absent, $Y^1$ is not

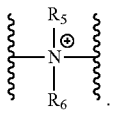

Yet another aspect of the present invention relates to a polymeric network comprising crosslinked monomers of Formula (III):

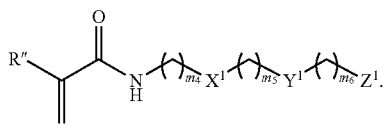

(III)

Another aspect of the present invention relates to a hydrogel comprising any one of the polymers as described herein, the polymeric network as described herein, or any combination thereof.

Another aspect of the present invention relates to a capsule comprising a hydrogel of the present invention and a therapeutic agent encapsulated in the hydrogel.

Another aspect of the present invention is directed to a method of delivering a therapeutic agent to a subject. This method involves administering, to a subject, a capsule comprising the hydrogel and a therapeutic agent encapsulated by the hydrogel as described herein.

A further aspect of the present invention is directed to a method of treating a diabetic subject. This method involves implanting, into a subject having diabetes, a capsule comprising a therapeutic agent as described herein.

Alginates and other polymers chemically modified with ultra-low fouling, zwitterionic groups such as sulfobetaine and carboxybetaine as described herein exhibit superior biocompatibility. The zwitterionic moiety endowed alginate with excellent long-term biocompatibility and suppressed the fibrotic response, while the alginate backbone remains crosslinkable under mild gelation condition. These materials are particularly suitable for cell encapsulation and transplantation as well as in other biological applications using alginate and hydrogels. This is the first work to develop zwitterion-based alginate conjugates, which have applicability in areas such as islet encapsulation for type 1 diabetes treatment.

BRIEF DESCRIPTION OF THE DRAWINGS

FIG. 2A shows synthetic pathway of the sulfobetaine-based alginate conjugates. FIG. 2B shows $^1$H NMR spectrum of alginate, sulfobetaine-based alginate conjugate, and sulfobetaine-$NH_2$ monomer in $D_2O$.

FIG. 3A shows synthetic pathway of the carboxybetaine-based alginate conjugates. FIG. 3B shows $^1$H NMR spectrum of alginate, carboxybetaine-based alginate conjugate, and carboxybetaine-$NH_2$ monomer in $D_2O$.

FIG. 9A is a representative dark-field phase contrast image of encapsulated rat islets in 1000 μm SB-SLG20 microcapsules. Scale bars, 500 μm. FIG. 9B is a graph showing blood glucose concentrations of mice from 3-month transplantation studies (n=3 mice per treatment group). FIG. 9C is representative dark-field phase contrast image (scale bars, 2000 μm) and FIG. 9D is an H&E stained cross-sectional image of retrieved islet-containing SLG 20 microcapsules after 90 days implantation. The whiteness of the capsule indicates the presence of fibrosis. FIG. 9E is a representative dark-field phase contrast image (scale bars, 2000 μm) and FIG. 9F is an H&E stained cross-sectional image of retrieved islet-containing SB-SLG 20 microcapsules after 90 days implantation. Note the absence of fibrosis on the capsules and numerous islets inside the capsules. FIG. 9G is an image showing immunohistochemical staining of islets (DAPI) in retrieved SB-SLG 20 microcapsules. Insulin also visualized with stain; scale bars, 50 μm.

FIG. 20A shows the chemical structure of qTR-CB. FIG. 20B shows synthetic route of qTR-CB. FIG. 20C shows typical surface plasmon resonance (SPR) sensorgrams showing protein adsorption from 1 mg/mL fibrinogen (Fg) or undiluted human plasma on the P(qTR-CB)-grafted or bare gold surfaces. Lines from top to bottom at 15 minutes are in the same order as the legend. FIG. 20D is an image of a P(qTR-CB) hydrogel.

FIG. 21A is a schematic illustration showing the π-π stacking between the triazole rings as potential mechanism for energy dissipation. FIG. 21B shows images of poly(carboxybetaine) (PCB) and P(qTR-CB) hydrogels during folding test. FIG. 21C is a graph showing stress-strain curves for PCB and P(qTR-CB) hydrogels in tensile test. FIG. 21D is a graph showing stress-strain curves for PCB and P(qTR-CB) hydrogels in compression test. FIG. 21E is a graph showing stress-strain curves of ten consecutive loading-unloading cycles for the P(qTR-CB) hydrogel.

FIG. 22A shows fluorescent microscopic images of NIH/3T3 cells after 3-days of culturing on tissue culture polystyrene (TCPS), poly(2-hydroxyethyl methacrylate) (PHEMA), PCB, and P(qTR-CB) hydrogel surfaces (Scale bars: 100 μm), and quantification of the cell density (Mean±s.d; n=5; *, p<0.05; ns, not significant). FIG. 22B is a graph showing quantification of TNF-α and IL10 secretion from macrophages cultured on various surfaces. (Mean±s.d; n=6; *, p<0.05; ns, not significant). The order of bars in each condition of each graph from left to right: TCPS, PHEMA, PCB, P(qTR-CB).

FIG. 23A shows synthetic routes to TR-CB and TR-SB monomers. FIG. 23B shows images of P(TR-CB) and P(TR-SB) hydrogels during folding test. FIG. 23C shows stretching of a P(TR-SB) hydrogel. FIG. 23D is a graph showing stress-strain curves for the PCB, P(TR-CB), and P(TR-SB) hydrogels in tensile test. FIG. 23E is a graph showing stress-strain curves for the PCB, P(TR-CB), and P(TR-SB) hydrogels in compression test.

FIG. 24A shows representative Masson's trichrome staining images of different hydrogels retrieved at the indicated time points after subcutaneous implantation. The blue staining indicates fibrosis or collagen deposition surrounding implants (Scale bars: 100 μm; asterisks indicate the location of the implanted hydrogel). FIG. 24B are graphs showing quantification of collagen density around the implants (n=5).

FIG. 26A (left) shows representative Masson's trichrome stain image of PCB hydrogel (the blue staining indicates fibrosis or collagen deposition surrounding implants; scale bar: 100 μm; asterisks indicate the location of the implanted hydrogel). The graph of FIG. 26A (right) shows quantification of collagen density around the implants. FIG. 26B (left) shows representative CD31 immunostaining image of PCB hydrogel (blood vessels are stained dark green and nuclei are stained blue; scale bars: 50 μm; asterisks indicate the location of the implanted hydrogel and dashed lines indicate the border between the fibrotic layer and the skin tissue). The graph of FIG. 26B (right) shows quantification of blood vessel density around the implants. All data are presented as mean value±s.d. (Five mice per type of hydrogel); *, P<0.05; ns, not significant.

DETAILED DESCRIPTION OF THE INVENTION

Figure 1A:
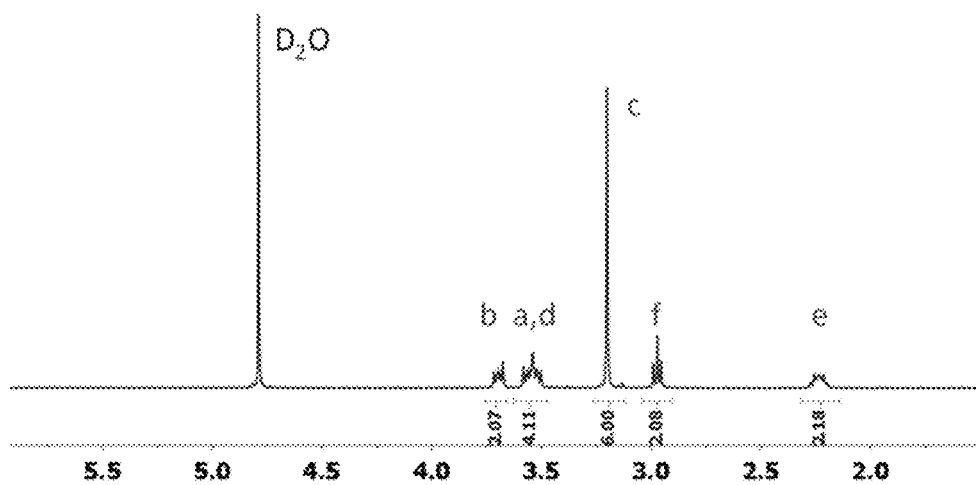
FIGS. 1A-1B show $^1$H NMR of spectrums of the sulfobetaine-$NH_2$ (FIG. 1A) and carboxybetaine-$NH_2$ (FIG. 1B) monomers.

One aspect of the present invention relates to a monomer of Formula (I):

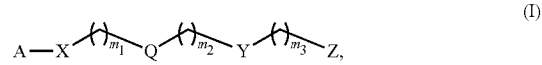

wherein
- A is selected from a saccharide containing unit and a polyvinyl alcohol containing unit;
- X is selected from the group consisting of O, NH, NR', C(O), and C$_{1-20}$ alkylene, wherein C$_{1-20}$ alkylene is optionally substituted from 1 to 20 times with a substituent selected independently at each occurrence thereof from the group consisting of OH, halogen, cyano, —CF$_3$, and C$_{1-6}$ alkoxy
- Q is optional, and if present is a linker;
- Y is selected from the group consisting of

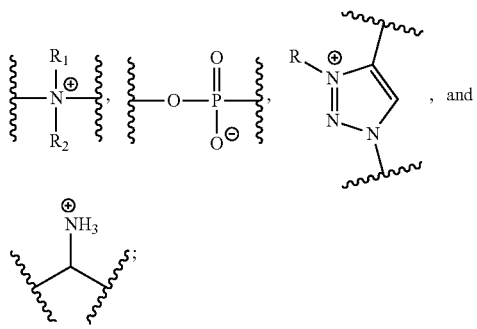

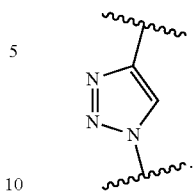

Z is selected from the group consisting of

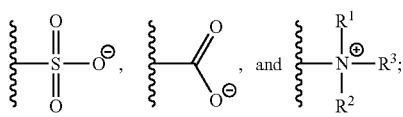

$m_1$ is 0 to 50;

$m_2$ is 0 to 50;

$m_3$ is 0 to 50;

R is $C_{1-20}$ alkyl;

R' is —C(O)—$C_{1-6}$ alkene;

$R^1$ is $C_{1-20}$ alkyl;

$R^2$ is $C_{1-20}$ alkyl; and $R^3$ is $C_{1-20}$ alkyl.

In one embodiment, Q is absent from the monomer of the present invention. In another embodiment, Q is present as a linker in the monomer of the present invention. Q is an organic grouping containing any number of carbon atoms, 1-30 carbon atoms, 1-20 carbon atoms, or 1-14 carbon atoms, and optionally including one or more heteroatoms such as nitrogen, sulfur, or nitrogen in linear, branched, or cyclic structural formats. Representative Q groupings being $C_{1-20}$ alkylene, substituted $C_{1-20}$ alkylene, phenoxy, substituted phenoxy, alkoxy, substituted alkoxy, $C_{3-20}$ cycloalkylene, substituted $C_{3-20}$ cycloalkylene, $C_{3-20}$ cycloalkenylene, substituted $C_{3-20}$ cycloalkenylene, $C_{8-20}$ cycloalkynylene, substituted $C_{8-20}$ cycloalkynylene, heterocyclylene, substituted heterocyclylene, arylene, substituted arylene, triazole, poly(ethylene glycol), or polypeptide moiety.

In one embodiment, Q is selected from the group consisting of $C_{1-20}$ alkylene, $C_{3-20}$ cycloalkylene, arylene, heteroarylene, heterocyclene, —O—$C_{1-20}$ alkylene, poly(ethylene glycol), and polypeptide, wherein $C_{1-20}$ alkylene, $C_{3-20}$ cycloalkylene, arylene, heteroarylene, heterocyclylene, or —O—$C_{1-20}$ alkylene is optionally substituted from 1 to 20 times with a substituent selected independently at each occurrence thereof from the group consisting of —OH, halogen, cyano, —CF$_3$, $C_{1-6}$ alkyl, and $C_{1-6}$ alkoxy, and wherein $C_{1-20}$ alkylene is optionally interrupted by one or more heteroatoms selected from the group consisting of oxygen nitrogen, sulfur, or nitrogen.

In another embodiment, Q is heteroarylene.

In yet another embodiment, Q is

As used above, and throughout the description herein, the following terms, unless otherwise indicated, shall be understood to have the following meanings. If not defined otherwise herein, all technical and scientific terms used herein have the same meaning as is commonly understood by one of ordinary skill in the art to which this technology belongs. In the event that there is a plurality of definitions for a term herein, those in this section prevail unless stated otherwise.

The term "alkyl" means an aliphatic hydrocarbon group which may be straight or branched having about 1 to about 20 (e.g., 1, 2, 3, 4, 5, 6, 7, 8, 9, 10, 11, 12, 13, 14, 15, 16, 17, 18, 19, 20) carbon atoms in the chain, unless otherwise specified. Branched means that one or more lower alkyl groups such as methyl, ethyl, or propyl are attached to a linear alkyl chain. Exemplary alkyl groups include methyl, ethyl, n-propyl, i-propyl, n-butyl, t-butyl, n-pentyl, and 3-pentyl.

The term "alkylene" means a group obtained by removal of a hydrogen atom from an alkyl group. An alkylene is a divalent, straight or branched chain alkane group. Non-limiting examples of alkylene include methylene and ethylene.

The term "alkenyl" means an aliphatic hydrocarbon group containing a carbon-carbon double bond and which may be straight or branched having about 2 to about 20 (e.g., 2, 3, 4, 5, 6, 7, 8, 9, 10, 11, 12, 13, 14, 15, 16, 17, 18, 19, 20) carbon atoms in the chain. Preferred alkenyl groups have 2 to about 6 (e.g., 2, 3, 4, 5, 6) carbon atoms in the chain. Exemplary alkenyl groups include ethenyl, propenyl, n-butenyl, and i-butenyl. An alkenylene is a divalent, straight or branched chain alkene group.

The term "alkynyl" means an aliphatic hydrocarbon group containing a carbon-carbon triple bond and which may be straight or branched having about 2 to about 20 (e.g., 2, 3, 4, 5, 6, 7, 8, 9, 10, 11, 12, 13, 14, 15, 16, 17, 18, 19, 20) carbon atoms in the chain. Preferred alkynyl groups have 2 to about 6 (e.g., 2, 3, 4, 5, 6) carbon atoms in the chain. Exemplary alkynyl groups include ethynyl, propynyl, n-butynyl, 2-butynyl, 3-methylbutynyl, and n-pentynyl. An alkynylene is a divalent, straight or branched chain alkyne.

The term "cycloalkyl" refers to a non-aromatic saturated mono- or polycyclic ring system which may contain 3 to 20 (e.g., 3, 4, 5, 6, 7, 8, 9, 10, 11, 12, 13, 14, 15, 16, 17, 18, 19, 20) carbon atoms. Exemplary cycloalkyl groups include, without limitation, cyclopropyl, cyclobutyl, cyclopentyl, cyclohexyl.

The term "cycloalkylene" means a group obtained by removal of a hydrogen atom from a cycloalkyl group. Non-limiting examples of cycloalkylene include cyclobutylene and cyclopropylene.

The term "cycloalkenyl" refers to a non-aromatic unsaturated mono- or polycyclic ring system which may contain 3 to 12 (e.g., 3, 4, 5, 6, 7, 8, 9, 10, 11, or 12) carbon atoms, and which includes at least one double bond. Exemplary cycloalkenyl groups include, without limitation, cyclopropenyl, cyclobutenyl, cyclopentenyl, cyclohexenyl. A cycloalkenylene is a divalent, straight or branched chain cycloalkene group.

The term "cycloalkynyl" refers to a non-aromatic unsaturated mono- or polycyclic ring system which may contain 8 to 12 carbon atoms, and which includes at least one triple bond. Exemplary cycloalkynyl groups include, without limitation, cyclononyne and cyclooctyne. A cycloalkynylene is a divalent, straight or branched chain cycloalkyne group.

As used herein, the term "heterocyclyl" refers to a stable 3- to 18-membered (e.g., 3-, 4-, 5-, 6-, 7-, 8-, 9-, 10-, 11-, 12-, 13-, 14-, 15-, 16-, 17-, or 18-membered) ring system that consists of carbon atoms and from one to five (e.g., 1, 2, 3, 4, or 5) heteroatoms selected from the group consisting of nitrogen, oxygen, sulfur, and silicon. The heterocyclyl may be a monocyclic or a polycyclic ring system, which may include fused, bridged, or spiro ring systems; and the nitrogen, carbon, sulfur, or silicon atoms in the heterocyclyl may be optionally oxidized; the nitrogen atom may be optionally quaternized; and the ring may be partially or fully saturated. Representative monocyclic heterocyclyls include piperidine, piperazine, pyrimidine, morpholine, thiomorpholine, pyrrolidine, tetrahydrofuran, pyran, tetrahydropyran, oxetane, and the like. Representative polycyclic heterocyclyls include indole, isoindole, indolizine, quinoline, isoquinoline, purine, carbazole, dibenzofuran, chromene, xanthene, and the like.

The term "heterocyclylene" means a group obtained by removal of a hydrogen atom from a heterocyclyl group. Non-limiting examples of heterocyclylene include piperidylene, pyrrolidinylene, piperazinylene, morpholinylene, thiomorpholinylene, thiazolidinylene, 1,4-dioxanylene, tetrahydrofuranylene and tetrahydrothiophenylene.

As used herein, the term "aryl" refers to an aromatic monocyclic or polycyclic ring system containing from 6 to 19 (e.g., 6, 7, 8, 9, 10, 11, 12, 13, 14, 15, 16, 17, 18, or 19) carbon atoms, where the ring system may be optionally substituted. Aryl groups of the present invention include, but are not limited to, groups such as phenyl, naphthyl, azulenyl, phenanthrenyl, anthracenyl, fluorenyl, pyrenyl, triphenylenyl, chrysenyl, and naphthacenyl.

The term "arylene" means a group obtained by removal of a hydrogen atom from an aryl group. Non-limiting examples of arylene include phenylene and naphthylene.

As used herein, "heteroaryl" refers to an aromatic ring radical which consists of carbon atoms and from one to five (e.g., 1, 2, 3, 4, or 5) heteroatoms selected from the group consisting of nitrogen, oxygen, sulfur, and silicon. Examples of heteroaryl groups include, without limitation, pyrrolyl, pyrazolyl, imidazolyl, triazolyl, furyl, thiophenyl, oxazolyl, isoxazolyl, thiazolyl, isothiazolyl, oxadiazolyl, thiadiazolyl, pyridyl, pyrazinyl, pyrimidinyl, pyridazinyl, triazinyl, thienopyrrolyl, furopyrrolyl, indolyl, azaindolyl, isoindolyl, indolinyl, indolizinyl, indazolyl, benzimidazolyl, imidazopyridinyl, benzotriazolyl, benzoxazolyl, benzoxadiazolyl, benzothiazolyl, pyrazolopyridinyl, triazolopyridinyl, thienopyridinyl, benzothiadiazolyl, benzofuyl, benzothiophenyl, quinolinyl, isoquinolinyl, tetrahydroquinolyl, tetrahydroisoquinolyl, cinnolinyl, quinazolinyl, quinolizilinyl, phthalazinyl, benzotriazinyl, chromenyl, naphthyridinyl, acrydinyl, phenanzinyl, phenothiazinyl, phenoxazinyl, pteridinyl, and purinyl. Additional heteroaryls are described in COMPREHENSIVE HETEROCYCLIC CHEMISTRY: THE STRUCTURE, REACTIONS, SYNTHESIS AND USE OF HETEROCYCLIC COMPOUNDS (Katritzky et al. eds., 1984), which is hereby incorporated by reference in its entirety.

The term "heteroarylene" means a group obtained by removal of a hydrogen atom from a heteroaryl group. Non-limiting examples of heteroarylene include pyridylene, pyrazinylene, furanylene, thienylene and pyrimidinylene.

The term "optionally substituted" is used to indicate that a group may have a substituent at each substitutable atom of the group (including more than one substituent on a single atom), provided that the designated atom's normal valency is not exceeded and the identity of each substituent is independent of the others. Up to three H atoms in each residue are replaced with alkyl, halogen, haloalkyl, hydroxy, loweralkoxy, carboxy, carboalkoxy (also referred to as alkoxycarbonyl), carboxamido (also referred to as alkylaminocarbonyl), cyano, carbonyl, nitro, amino, alkylamino, dialkylamino, mercapto, alkylthio, sulfoxide, sulfone, acylamino, amidino, phenyl, benzyl, heteroaryl, phenoxy, benzyloxy, or heteroaryloxy. "Unsubstituted" atoms bear all of the hydrogen atoms dictated by their valency. When a substituent is keto (i.e., =O), then two hydrogens on the atom are replaced. Combinations of substituents and/or variables are permissible only if such combinations result in stable compounds; by "stable compound" or "stable structure" is meant a compound that is sufficiently robust to survive isolation to a useful degree of purity from a reaction mixture, and formulation into an efficacious therapeutic agent.

The term "substituted" or "substitution" means that one or more hydrogen on a designated atom is replaced with a selection from the indicated group, provided that the designated atom's normal valency is not exceeded. "Unsubstituted" atoms bear all of the hydrogen atoms dictated by their valency. When a substituent is oxo (i.e., =O), then 2 hydrogens on the atom are replaced. Combinations of substituents and/or variables are permissible only if such combinations result in stable compounds. By "stable compound" it is meant a compound that is sufficiently robust to survive isolation to a useful degree of purity from a reaction mixture, and formulation into an efficacious therapeutic agent. Exemplary substituents include, without limitation, oxo, thio (i.e., =S), nitro, cyano, halo, OH, $NH_2$, $C_1$-$C_6$ alkyl, $C_1$-$C_6$ alkoxy, $C_2$-$C_6$ alkenyl, $C_2$-$C_6$ alkynyl, $C_3$-$C_6$ cycloalkyl, $C_4$-$C_7$ cycloalkylalkyl, monocyclic aryl, monocyclic hetereoaryl, polycyclic aryl, and polycyclic heteroaryl.

The term "monocyclic" indicates a molecular structure having one ring.

The term "polycyclic" indicates a molecular structure having two or more rings, including, but not limited to, fused, bridged, or spiro rings.

The term "halogen" means fluorine, chlorine, bromine, or iodine.

The term "cyano" means a cyano group as shown below

The term "alkoxy" means groups of from 1 to 8 carbon atoms of a straight, branched, or cyclic configuration and combinations thereof attached to the parent structure through an oxygen. Examples include methoxy, ethoxy, propoxy, isopropoxy, cyclopropyloxy, cyclohexyloxy, and the like. Lower-alkoxy refers to groups containing one to four carbons. For the purposes of the present patent application, alkoxy also includes methylenedioxy and ethylenedioxy in which each oxygen atom is bonded to the atom, chain, or ring from which the methylenedioxy or ethylenedioxy group is pendant so as to form a ring. Thus, for example, phenyl substituted by alkoxy may be, for example,

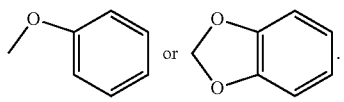

Monomers and compounds as described herein may contain one or more asymmetric centers and may thus give rise to enantiomers, diastereomers, and other stereoisomeric forms. Each chiral center may be defined, in terms of absolute stereochemistry, as (R)- or (S)-. The present invention is meant to include all such possible isomers, as well as mixtures thereof, including racemic and optically pure forms. Optically active (R)- and (S)-, (−)- and (+)-, or (D)- and (L)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included.

As referred to herein, a "polyvinyl alcohol containing unit" is a unit comprising the chemical formula of $CH_2=CH(OH)$ or

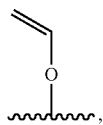

wherein

is the point of attachment of A to X and wherein $CH_2=CH(OH)$ and

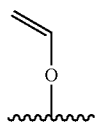

can be optionally substituted.

As used herein, a "saccharide containing unit" is any chemical unit comprising a saccharide, in particular, a chemical unit comprising a monosaccharide, a disaccharide, or an oligosaccharide.

Monosaccharides are aldehydes or ketone derivatives of polyhydroxy alcohols having the general structure of $(CH_2O)_n$, where $n \geq 3$. The monosaccharide can be, without limitation, a substituted or unsubstituted triose, triulose, tetrose, tetulose, pentose, pentulose, penturonic acid, hexose, hexulose, hexuronic acid, heptose, heptulose, or hepturonic acid in its dextro (D-) or levo (L) form. Exemplary monosaccharides include, without limitation, a substituted or unsubstituted, erythrose, threose, ribose, arabinose, xylose, lyxose, allose, altrose, glucose, mannose, gulose, idose, galactose, talose, fucose, fructose, erythrulose, ribulose, xylulose, psicose, sorbose, tagatose, and derivatives thereof, such as aldonic and uronic acids (e.g., gluconic acid, mannuronic acid, glucuronic acid, galacturonic acid, mannuronic acid, xyluronic acid), deoxy sugars (e.g., deoxyribose, rhamnose, and fucose), and amino sugars (e.g., glucosamine, galactosamine, N-acetylmuramic acid), the like. Other monosaccharides suitable for use in the monomers and polymers as described herein are well known in the art.

Disaccharides comprise two monosaccharides linked together by glycosidic bonds, and oligosaccharides comprise more than two, usually three to ten monosaccharides linked together by glycosidic bonds. A disaccharide or oligosaccharide containing unit of the monomers and polymers as described herein may comprise one type, or more than one type, of monosaccharide. Exemplary disaccharides include, without limitation, sucrose, lactose, maltose, trehalose, cellobiose, isomaltose, maltitol and the like. Exemplary oligosaccharides include, without limitation, fructo-oligosaccharides, galacto-oligosaccharides, gluco-oligosaccharides, raffinose, and the like.

In one embodiment, the saccharide containing unit of the monomer described herein is mannuronate or guluronate selected from the following:

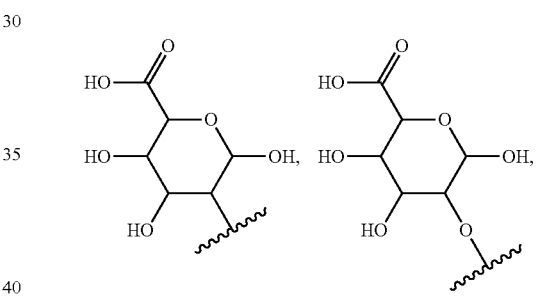

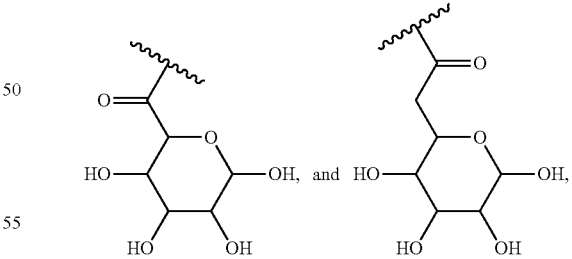

where

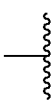

is the point of attachment of A to X.

In one embodiment, the monomer of the present invention has the Formula (Ia):
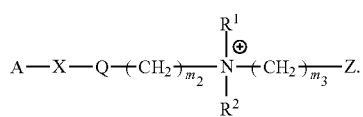 (Ia)
In one embodiment, the monomer of the present invention has the Formula (Ib):
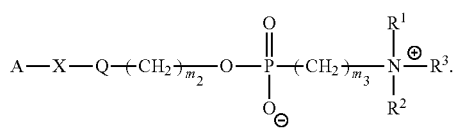 (Ib)
In another embodiment the monomer of the present invention has the Formula (Ic):
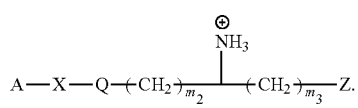 (Ic)
In another embodiment the monomer of the present invention has the formula selected from the group consisting of:
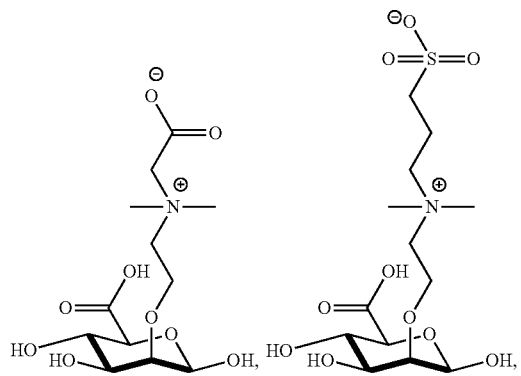
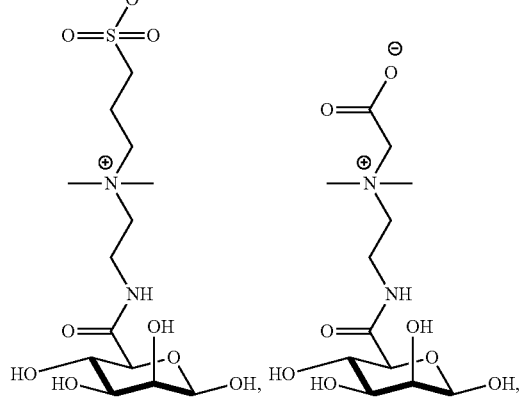
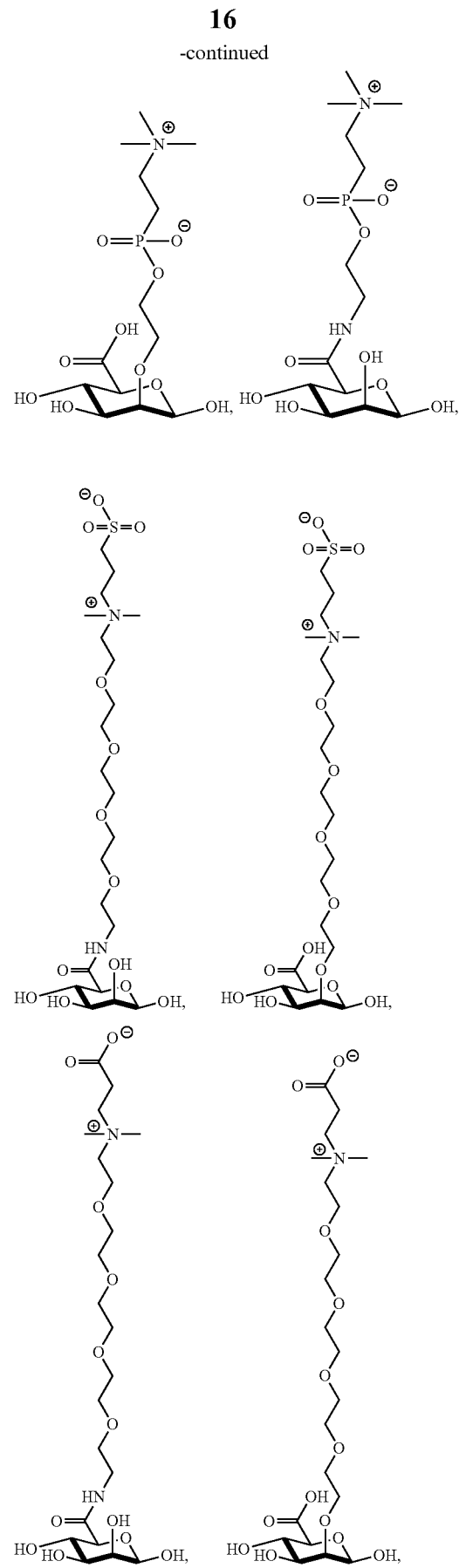

-continued

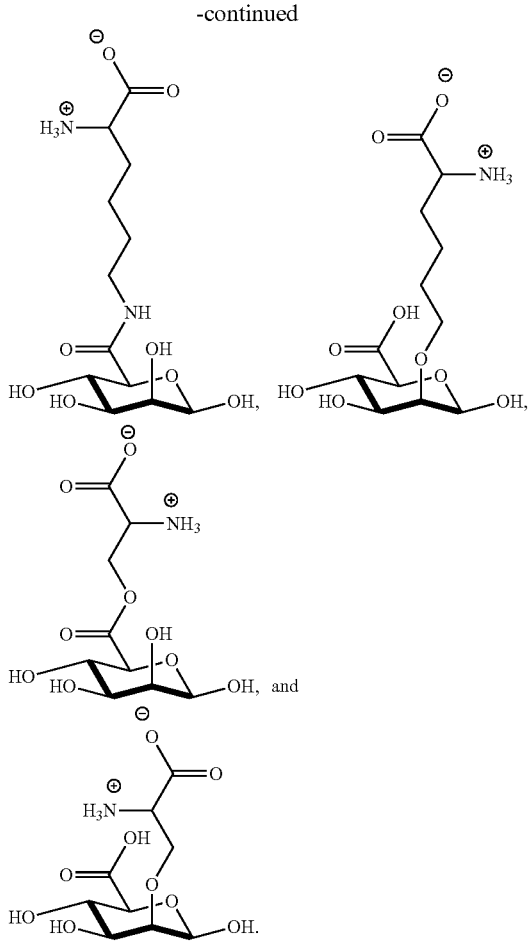

Another aspect of the present invention is directed to a polymer of Formula (IV):

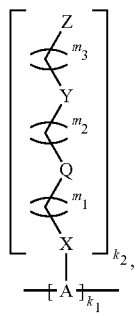

(IV)

wherein
A is independently selected from a saccharide containing unit and a polyvinyl alcohol containing unit for each monomer unit of the polymer;
X is selected from the group consisting of O, NH, NR', C(O), and $C_{1-20}$ alkylene, wherein $C_{1-20}$ alkylene is optionally substituted from 1 to 20 times with a substituent selected independently at each occurrence thereof from the group consisting of OH, halogen, cyano, —$CF_3$, and $C_{1-6}$ alkoxy.

Q is absent or is a linker;
Y is selected from the group consisting of

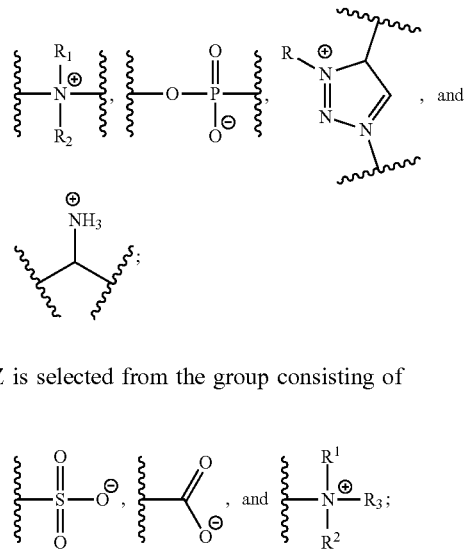

, and

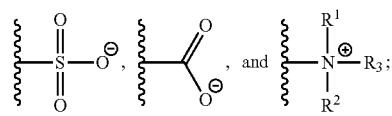

;

Z is selected from the group consisting of

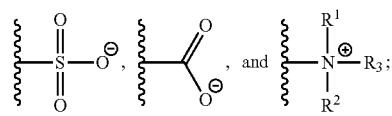

$m_1$ is 0 to 50;
$m_2$ is 0 to 50;
$m_3$ is 0 to 50;
R is $C_{1-20}$ alkyl;
R' is —C(O)—$C_{1-6}$ alkene;
$R^1$ is $C_{1-20}$ alkyl;
$R^2$ is $C_{1-20}$ alkyl;
$R^3$ is $C_{1-20}$ alkyl,
$k_1$ is any integer; and
$k_2$ is independently selected for each monomer unit from 0 or 1, with the proviso that at least one $k_2$ is 1;
wherein the monomer units of the polymer are the same or different.

In one embodiment, Q is absent from the monomer unit of the polymer. In another embodiment, Q is present as a linker in the monomer unit of the polymer. Q is an organic grouping containing any number of carbon atoms, 1-30 carbon atoms, 1-20 carbon atoms, or 1-14 carbon atoms, and optionally including one or more heteroatoms such as nitrogen, sulfur, or nitrogen in linear, branched, or cyclic structural formats. Representative Q groupings being $C_{1-20}$ alkylene, substituted $C_{1-20}$ alkylene, phenoxy, substituted phenoxy, alkoxy, substituted alkoxy, $C_{3-20}$ cycloalkylene, substituted $C_{3-20}$ cycloalkylene, $C_{3-20}$ cycloalkenylene, substituted $C_{3-20}$ cycloalkenylene, $C_{8-20}$ cycloalkynylene, substituted $C_{8-20}$ cycloalkynylene, heterocyclylene, substituted heterocyclylene, arylene, substituted arylene, triazole, poly(ethylene glycol), or polypeptide moiety.

In one embodiment, Q is selected from the group consisting of $C_{1-20}$ alkylene, $C_{3-20}$ cycloalkylene, arylene, heteroarylene, heterocyclene, —O—$C_{1-20}$ alkylene, poly(ethylene glycol), and polypeptide, wherein $C_{1-20}$ alkylene, $C_{3-20}$ cycloalkylene, arylene, heteroarylene, heterocyclylene, or —O—$C_{1-20}$ alkylene is optionally substituted from 1 to 20 times with a substituent selected independently at each occurrence thereof from the group consisting of —OH, halogen, cyano, —$CF_3$, $C_{1-6}$ alkyl, and $C_{1-6}$ alkoxy, and wherein $C_{1-20}$ alkylene is optionally interrupted by one or more heteroatoms selected from the group consisting of oxygen nitrogen, sulfur, or nitrogen.

In another embodiment, Q is heteroarylene.

In yet another embodiment, Q is

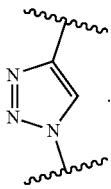 [SMILES: *c1cn(*)nn1]

In one embodiment, the polymer of the present invention has Formula (IVa):

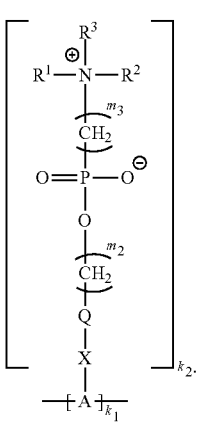

(IVa)

In another embodiment, the polymer of the present invention has Formula (IVb):

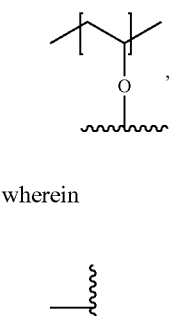

(IVb)

In another embodiment, the polymer of the present invention Formula (IVc):

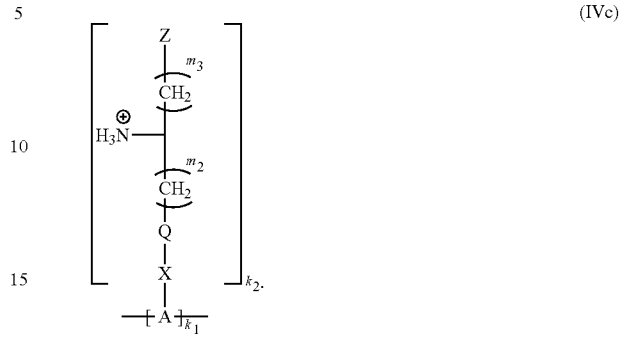

(IVc)

A "polymer" as referred to herein, is a macromolecule comprising a set of regularly repeated chemical units, i.e., monomer units, that are joined together to form a chain molecule. The repeated monomers can be of the same type, or of a limited number of different types. The number of monomer units in the polymers as described herein can be any integer. In one embodiment, the number ($k_1$) of monomer units in the polymer is from about 5 to about 1,000 units, from about 5 to about 10,000 units, or from about 5 to about 100,000 units.

The monomers of the polymer may be joined together end-to-end, or in a more complicated fashion when forming the chemical chain. The polymers described herein can be homopolymers, i.e., comprising only one type of repeating monomer unit, or copolymers, i.e., comprising more than one type of repeating monomer unit. Copolymers of the present disclosure include alternating polymers, periodic polymers, random polymers, and block polymers. The polymers described herein include linear polymers and branched polymers, including star polymers, brush polymers and comb polymers.

In one embodiment, the polymer as described herein is a polyvinyl alcohol containing polymer (i.e., the polymer has a polyvinyl alcohol backbone), where A at each instance of Formula IV is a polyvinyl alcohol containing unit.

As referred to herein, a "polyvinyl alcohol containing unit" is a unit comprising the chemical formula of —$CH_2CH(OH)$— or wherein is the point of attachment of A to X and wherein —$CH_2CH(OH)$— and

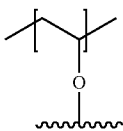

can be optionally substituted.

In another embodiment, the polymer as described herein is a saccharide containing polymer (i.e., the polymer has a saccharide backbone). In this embodiment, A of Formula IV is a saccharide containing unit. As described supra, a saccharide containing unit is any chemical unit comprising a saccharide, in particular, a chemical unit comprising a monosaccharide, a disaccharide, or an oligosaccharide. In accordance with this embodiment, A is independently selected at each occurrence from a monosaccharide, disaccharide, and oligosaccharide. Exemplary saccharides are described supra.

In one embodiment, the polymer as described herein is a homopolymer comprising one type of monosaccharide containing monomer unit as described herein. In another embodiment, the homopolymer comprises one type of disaccharide containing monomer unit as described herein. In another embodiment, the homopolymer comprises one type of oligosaccharide containing monomer unit as described herein.

In another embodiment, the polymer is a copolymer containing two or more different monomer units. In one embodiment the copolymer comprises two or more different monosaccharide containing monomer units as described herein. In another embodiment, the copolymer comprises two or more different disaccharide containing monomer units. In another embodiment, the copolymer comprises two or more different oligosaccharide containing monomer units. In another embodiment, the copolymer comprises two or more different monomer units, where each monomer unit is independently selected from a monosaccharide, disaccharide, and oligosaccharide containing monomer unit.

In one embodiment, the polymer of the present invention is a modified saccharide polymer. Saccharide polymers, also known as polysaccharides or polymeric carbohydrates, are polymers comprising repeating monomeric units of one or more saccharides linked together by glycosidic linkages. Saccharide polymers are well known in the art, including, for example and without limitation, alginate, hyaluronic acid, chitin, cellulose, starch, agarose, dextran, carrageenan, guar, chondroitin, dermatan, among others. Thus, a modified saccharide polymer of the present invention is a polymer where A of Formula IV is a monomeric saccharide unit or a monosaccharide unit of a known saccharide polymer, and $k_2$ of one or more monomeric units is 1.

Accordingly, in one embodiment, the polymer of the present invention is a modified cellulose polymer. According to this embodiment, A of Formula IV comprises a glucose unit or substituted glucose unit to form the modified cellulose polymer or derivative thereof (e.g., a modified alkyl cellulose, hydroxyalkyl cellulose, carboxyalkyl cellulose, or cellulose ester).

In another embodiment, the polymer of the present invention is a modified dextran polymer. According to this embodiment, A of Formula IV is a D-glucopyranosyl unit to form the modified dextran polymer.

In another embodiment, the polymer of the present invention is a modified agarose polymer. According to this embodiment, A of Formula IV alternates and is selected from D-galactose and 3,6-anhydro-L-galactopyranose to form a modified agarose polymer.

In another embodiment, the polymer of the present invention is a modified chitosan polymer. According to the embodiment, A of Formula IV is independently selected from D-glucosamine and N-acetyl-D-glucosamine to form a modified chitosan polymer.

In another embodiment, the polymer of the present invention is a modified carrageenan polymer. According to this embodiment, A of Formula IV alternates and is selected from galactose and 3,6 anhydrogalactose to form the modified carrageenan polymer.

In another embodiment, the polymer of the present invention is a modified hyaluronan polymer. According to this embodiment, A of Formula IV alternates and is selected from glucuronic acid and N-acetyl-D-glucosamine to form a modified hyaluronan polymer.

In another embodiment, the polymer of the present invention is a modified chondroitin polymer. According to this embodiment, A of Formula IV alternates and is selected from glucuronic acid and N-acetylgalactosamine to form the modified chondroitin sulfate polymer.

In another embodiment, the polymer of the present invention is a modified dermatan polymer. According to this embodiment, A of Formula IV alternates and is selected from iduronic acid and N-acetylgalactosamine to form a modified dermatan sulfate polymer.

In another embodiment, the polymer of the present invention is a guar polymer. According to this embodiment, A of Formula IV is independently selected from galactose and mannose to form a modified guar polymer.

In one embodiment, the polymer of the present disclosure is a modified alginate polymer. Alginate is a linear copolymer with homopolymeric blocks of (1-4)-linked β-D-mannuronate and α-L-guluronate. In accordance with this embodiment, A at each occurrence in Formula IV is selected from β-D-mannuronate and α-L-guluronate. In one embodiment, the polymer comprises homopolymeric blocks of mannuronate containing monomer units. In another embodiment, the polymer comprises homopolymeric blocks of guluronate containing monomer units. In another embodiment, the polymer comprises alternating mannuronate and guluronate containing monomer units or alternating blocks of mannuronate and guluronate containing monomer units. In one embodiment, the ratio of mannuronate to guluronate in the polymer of the present invention is about 1. In another embodiment, the ratio of mannuronate to guluronate is greater than 1. In another embodiment, the ratio of mannuronate to guluronate is less than 1.

In accordance with this aspect of the present invention, exemplary alginate polymers of the disclosure comprise monomer units where A is independently selected at each occurrence from:

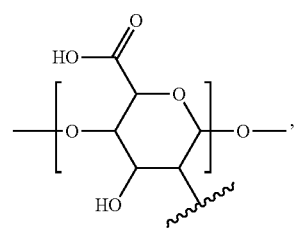

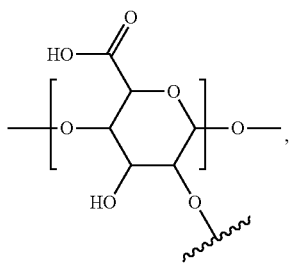
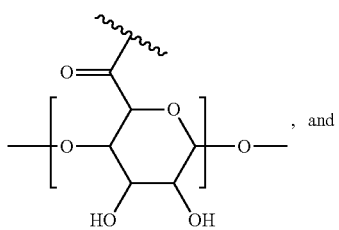, and
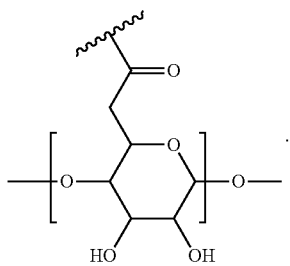
where
is the point of attachment of A to X.
Exemplary modified alginate polymers of the present invention include monomeric units independently selected at each occurrence from the following:
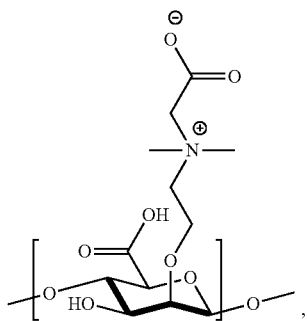
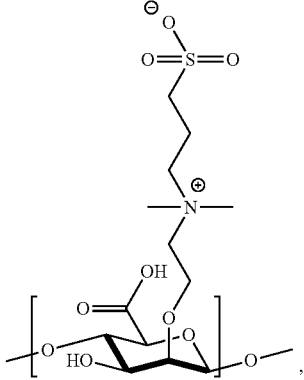
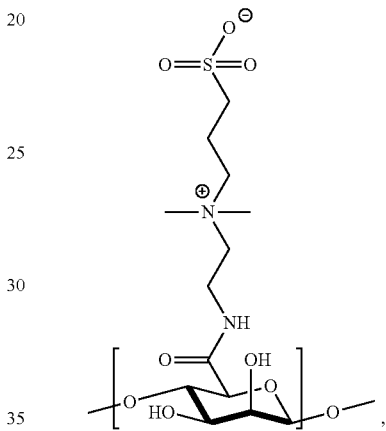
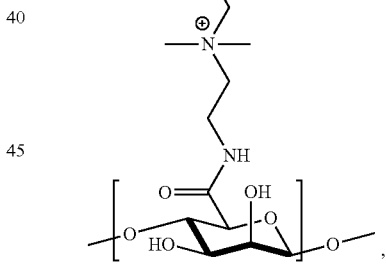
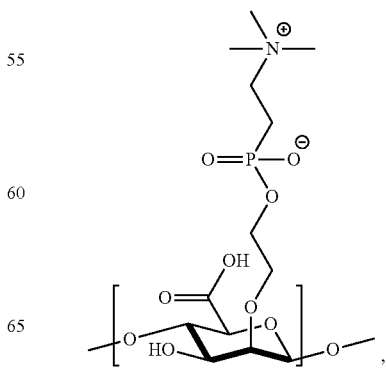

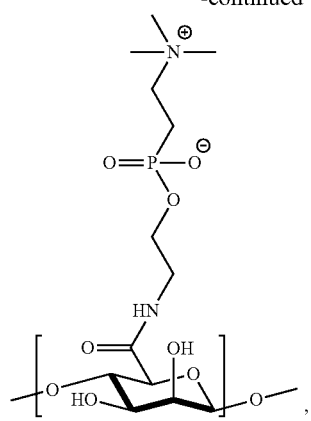
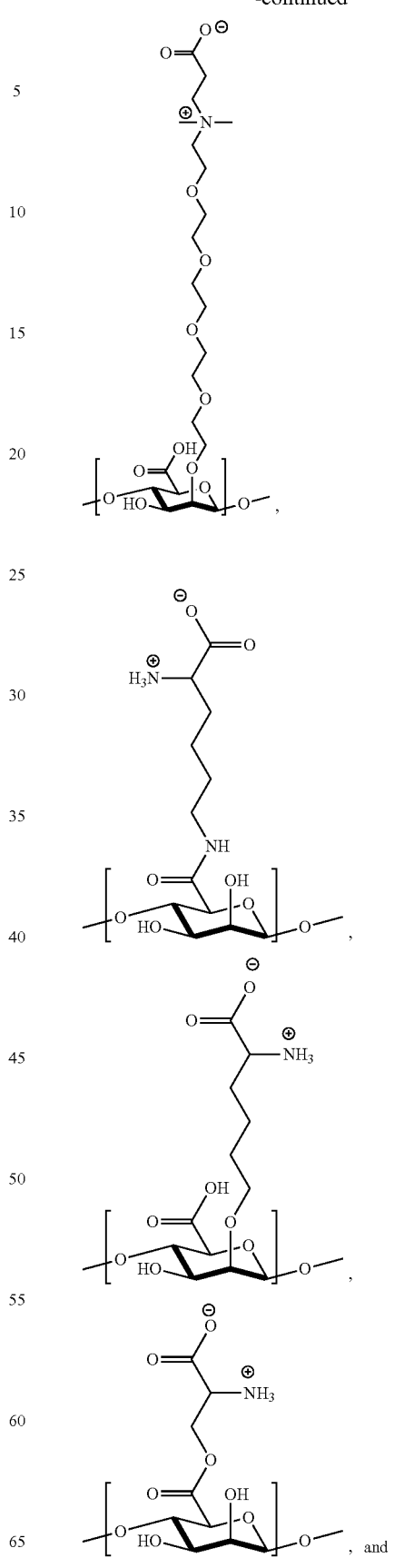

-continued

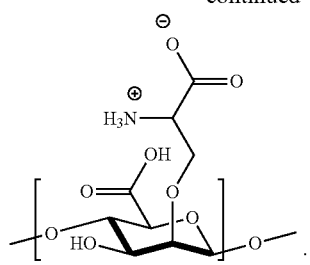

In accordance this aspect of the invention, $k_2$ of the polymer of Formula IV is independently selected for each monomer unit from 0 or 1, with the proviso that at least one $k_2$ is 1. In one embodiment, $k_2$ is 1 for at least 1% of the monomer units of the polymer as described herein. In another embodiment, $k_2$ is 1 for at least 5%, 10%, 15%, 20%, 25%, 30%, 35%, 40%, 45%, 50%, 55%, 60%, 65%, 70%, 75%, 80%, 85%, 90%, 95% or more of the monomer units of the polymer as described herein. In one embodiment, $k_2$ is 1 for 100% of the monomer units of the polymer as described herein.

Another aspect of the present invention relates to a polymer comprising one or more monomers of Formula (I):

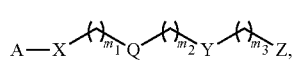  (I)

and further comprising
one or more monomers of Formula (II):

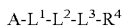  (II), wherein $L^1$ is selected from the group consisting of O, NH, NR', C(O), and $C_{1-20}$ alkylene, wherein $C_{1-20}$ alkylene is optionally substituted from 1 to 20 times with a substituent selected independently at each occurrence thereof from the group consisting of OH, halogen, cyano, —$CF_3$, and $C_{1-6}$ alkoxy, $L^2$ is absent or is $C_{1-20}$ alkylene, wherein $C_{1-20}$ alkylene is optionally substituted from 1 to 20 times with a substituent selected independently at each occurrence thereof from the group consisting of OH, halogen, cyano, —$CF_3$, and $C_{1-6}$ alkoxy;

$L^3$ is selected from the group consisting of $C_{1-20}$ alkylene, $C_{1-20}$ alkenylene, $C_{3-12}$ cycloalkenylene, and arylene, wherein arylene is optionally substituted from 1 to 3 times with a substituent selected independently at each occurrence thereof from the group consisting of heteroarylene and heterocyclylene;

$R^4$ is selected from the group consisting of H, SH, $N_3$, $C_{1-6}$ alkyl, $C_{2-20}$ alkenyl, $C_{2-20}$ alkynyl, $C_{3-12}$ cycloalkenyl, $C_{3-12}$ cycloalkynyl, heteroaryl, and heterocyclyl, wherein $C_{1-6}$ alkyl, $C_{2-20}$ alkenyl, $C_{2-20}$ alkynyl, $C_{3-12}$ cycloalkenyl, $C_{3-12}$ cycloalkynyl, heteroaryl, and heterocyclyl is optionally substituted from 1 to 3 times with a substituent selected independently at each occurrence thereof from the group consisting of H, OH, halogen, cyano, —$CF_3$, and $C_{1-6}$ alkoxy.

In one embodiment of this aspect of the present invention, the polymer has Formula (IIa):

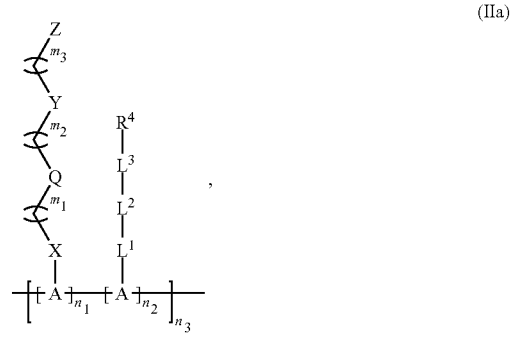  (IIa)

wherein $n_1$, $n_2$, and $n_3$ are any integer.

In one embodiment, $n_1$, $n_2$, and $n_3$ are each selected independently from an integer of 1 to 10,000.

Exemplary polymers in accordance with this aspect of the disclosure, include, without limitation, the following polymers:

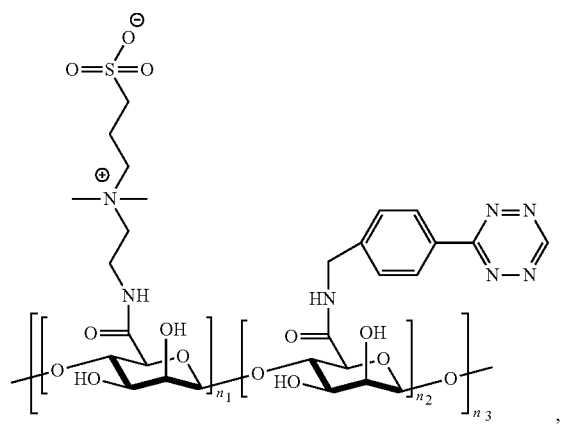

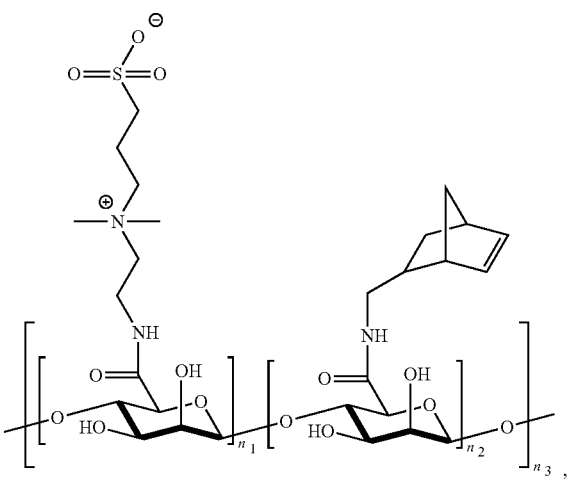

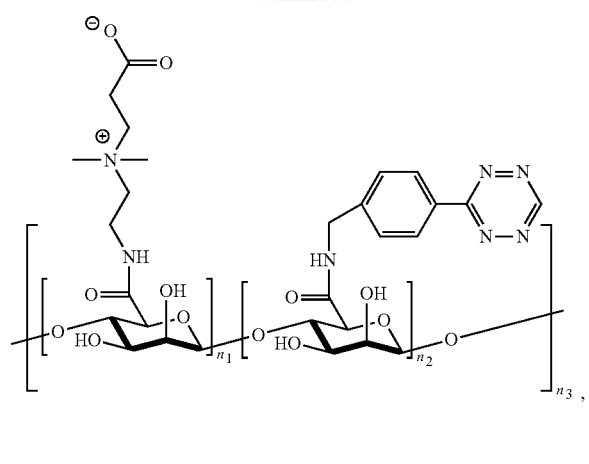
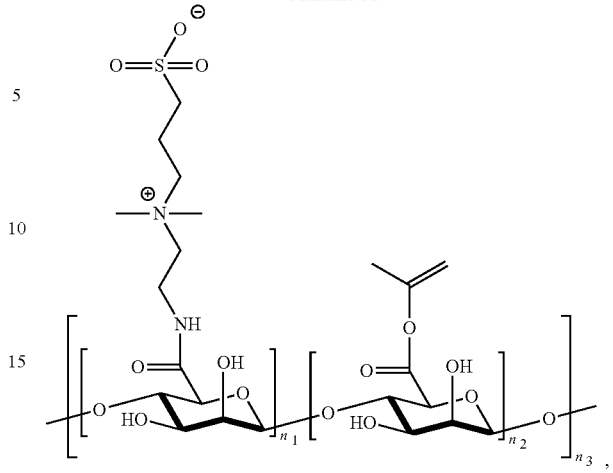
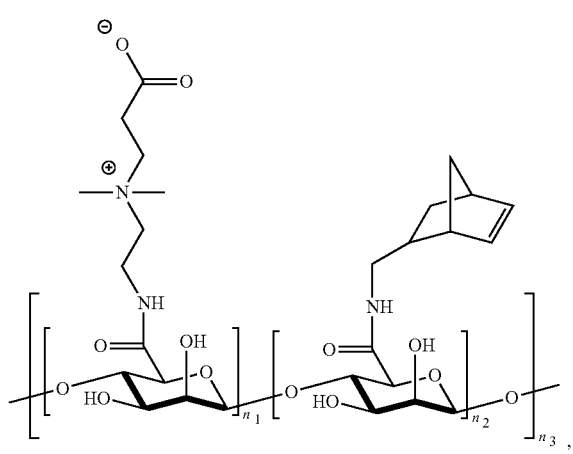
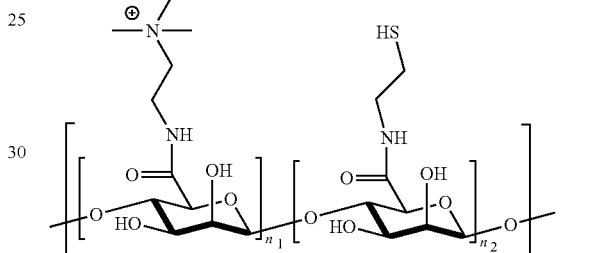
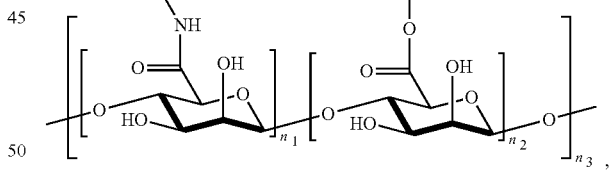
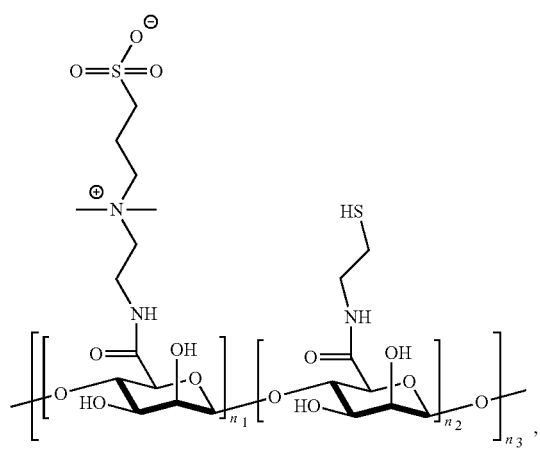
where $n_1$, $n_2$ and $n_3$ are any integer. In one embodiment, $n_1$, $n_2$, and $n_3$ are each selected independently from an integer of 1 to 10,000.
Another aspect of the present invention relates to a monomer of Formula (III):
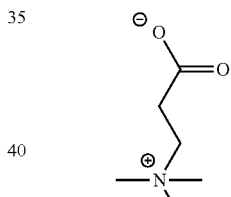
(III)

wherein $X^1$ is absent or is

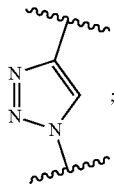

;

$Y^1$ is

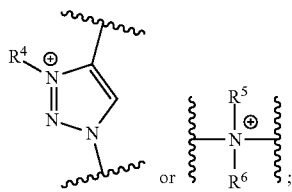

$Z^1$ is

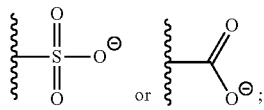

;

$m_4$ is 1 to 50;
$m_5$ is 0 to 10;
$m_6$ is 1 to 50;
R" is H or $C_{1-6}$ alkyl;
$R^4$ is $C_{1-20}$ alkyl;
$R^5$ is $C_{1-20}$ alkyl; and
$R^6$ is $C_1$-20 alkyl,
with the proviso that when $X^1$ is absent, $Y^1$ is not

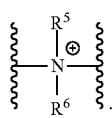

.

In one embodiment, the monomer of Formula (III) has Formula (III'):

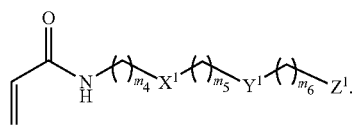

(III')

In one embodiment the monomer of Formula (III) has Formula (IIIa):

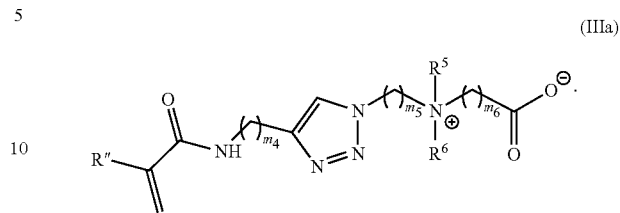

(IIIa)

In one embodiment, the monomer of Formula (III) has Formula (IIIa'):

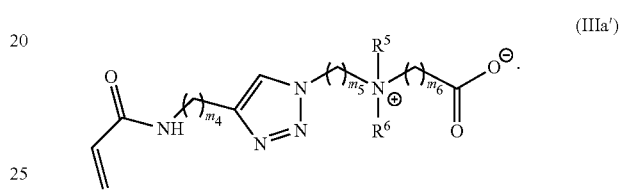

(IIIa')

In another embodiment, the monomer of Formula (III) has Formula (IIb):

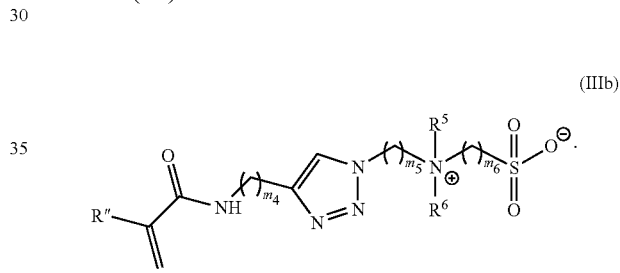

(IIIb)

In another embodiment, the monomer of Formula (III) has Formula (IIIb'):

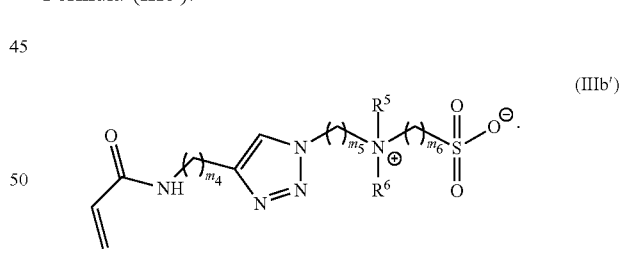

(IIIb')

In another embodiment, the monomer of Formula (III) has Formula (IIc):

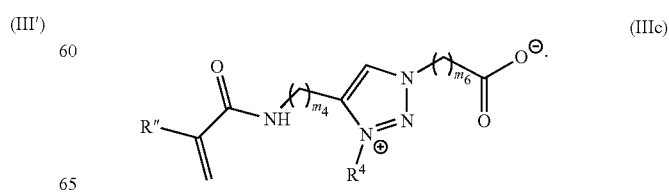

(IIIc)

In another embodiment, the monomer of Formula (III) has Formula (IIIc'):

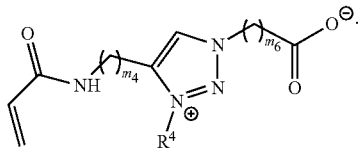

(IIIc')

In another embodiment, an exemplary monomer of Formula (III) is selected from the group consisting of:

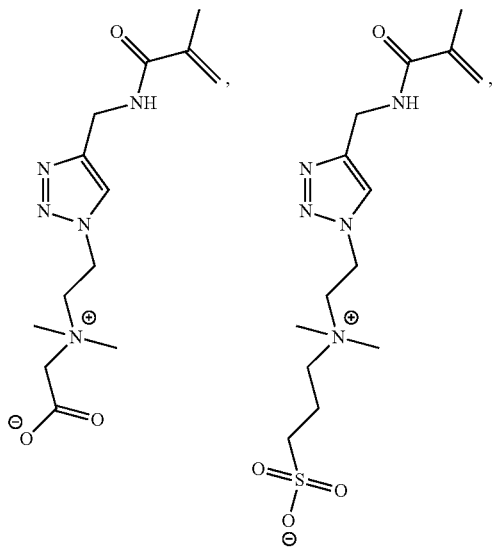

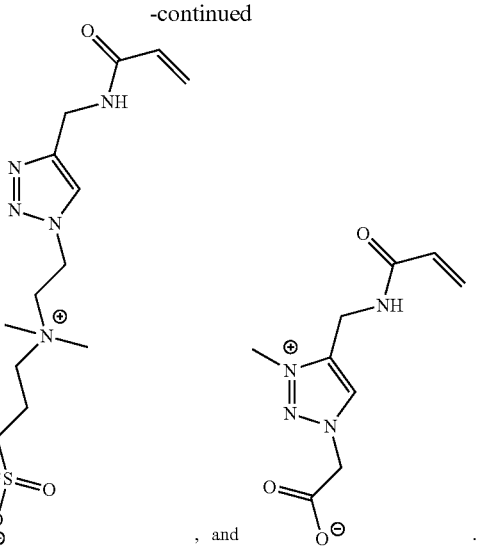

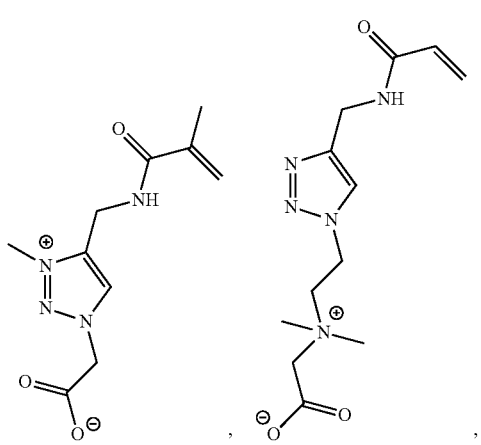

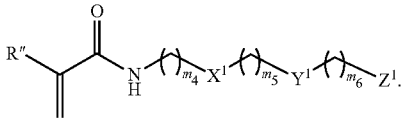

, and

Another aspect of the present invention relates to a polymeric network of crosslinked monomers of Formula (III):

$$R''\text{—}C(=O)\text{—}NH\text{—}(\ )_{m_4}\text{—}X^1\text{—}(\ )_{m_5}\text{—}Y^1\text{—}(\ )_{m_6}\text{—}Z^1.$$

(III)

In one embodiment, the network is a homopolymeric network, comprising one type of monomer of Formula (III). In another embodiment, the network is heteropolymeric, comprising two or more different monomers of Formula (III).

In accordance with this embodiment, the polymeric network of monomers is formed using a crosslinker agent, and the monomers of the network are linked together via the crosslinker. In one embodiment, the crosslinking agent is a zwitterionic crosslinking agent. The zwitterionic crosslinking agent can be copolymerized with the monomers and co-monomers of Formula III to provide crosslinked polymeric networks of the present invention. Suitable crosslinkers that can be used according to the present invention include bifunctional zwitterionic carboxybetaine diacrylamide cross-linker (CBAAX), as well as any of the zwitterionic crosslinking agents disclosed in U.S. Patent Application Publication No. 20170009069 to Jiang et al., which is hereby incorporated by reference in its entirety.

Another aspect of the present invention relates to a hydrogel comprising any one or more of the polymers described herein (i.e., polymers of Formula IV), any one or more monomers of Formula III, any one or more of the polymeric networks as described herein, or any combination thereof. Preferred hydrogels as described herein are zwitterionic hydrogels.

Hydrogels of the present invention can be homopolymeric hydrogels, copolymeric hydrogels, or multipolymeric hydrogels. In one embodiment, the hydrogel comprises one type of polymer as described herein. In another embodiment, the hydrogel comprises two or more different types of polymers as described herein. In another embodiment, the hydrogel is made from a single type of monomer of Formula III. In another embodiment, the hydrogel comprises two or more different types of monomers of Formula III. In another embodiment, the hydrogel is made from a polymeric network comprising a single type of monomer of Formula III. In another embodiment, the hydrogel is made from a polymeric network comprising one or more different types of monomers of Formula III.

In one embodiment, the hydrogel is a saccharide hydrogel, i.e., a hydrogel comprising saccharide containing polymers as described here. In another embodiment, the hydrogel is an alginate hydrogel, i.e., a hydrogel comprising modified alginate polymers as described herein.

Hydrogels of the present invention are formed using conventional methods known to those in the art and described in the Examples herein. For example the cross-links between the polymers and monomers of the hydrogel can be formed via chemical crosslinking reaction, ionizing radiation, or physical interactions.

In one embodiment, the hydrogel is formed using click chemistry. Click chemistry encompasses chemical reactions used to couple two compounds together which are high yielding, wide in scope, create only byproducts that can be removed without chromatography, are stereospecific, simple to perform, and can be conducted in easily removable or benign solvents. Examples of reactions which fulfill these criteria include the nucleophilic ring opening of epoxides and aziridines, non-aldol type carbonyl reactions, including the formation of hydrazones and heterocycles, additions to carbon-carbon multiple bonds, including Michael Additions, and cycloaddition reactions, such as a 1,3-dipolar cycloaddition reaction (i.e. a Huisgen cycloaddition reaction). See e.g., Moses and Moorhouse, *Chem Soc. Rev.*, 36:1249-1262 (2007); Kolb and Sharpless, *Drug Discovery Today*, 8(24): 1128-1137 (2003); and Kolb et al., *Angew. Chem. Int. Ed.* 40:2004-2021 (2001), which are hereby incorporated by reference in their entirety.

In one embodiment the hydrogel is formed by the reaction between alkene and tetrazine substituents of the polymers. In another embodiment the hydrogel is formed by the reaction between norbornene and tetrazine substituents of the polymers.

Hydrogels according to the present invention can be prepared according to the Schemes A and B.

Scheme A

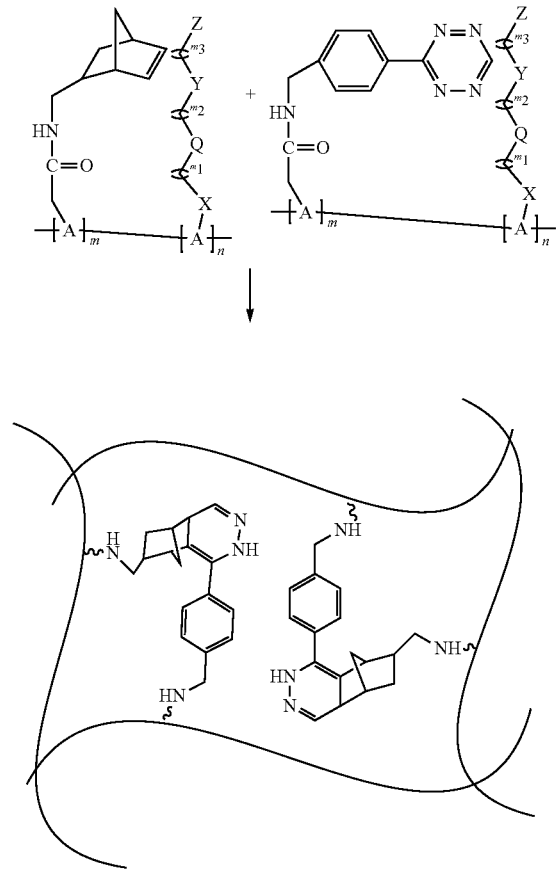

Scheme B

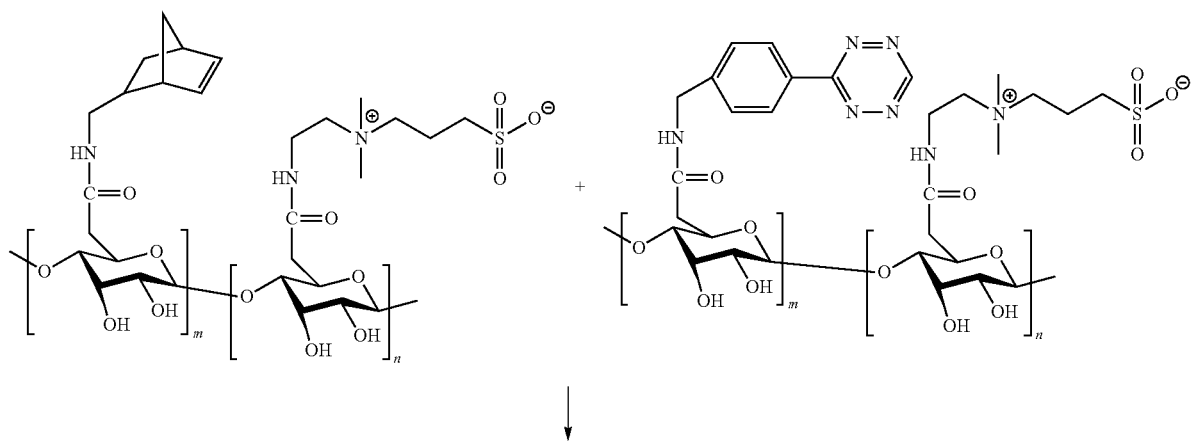

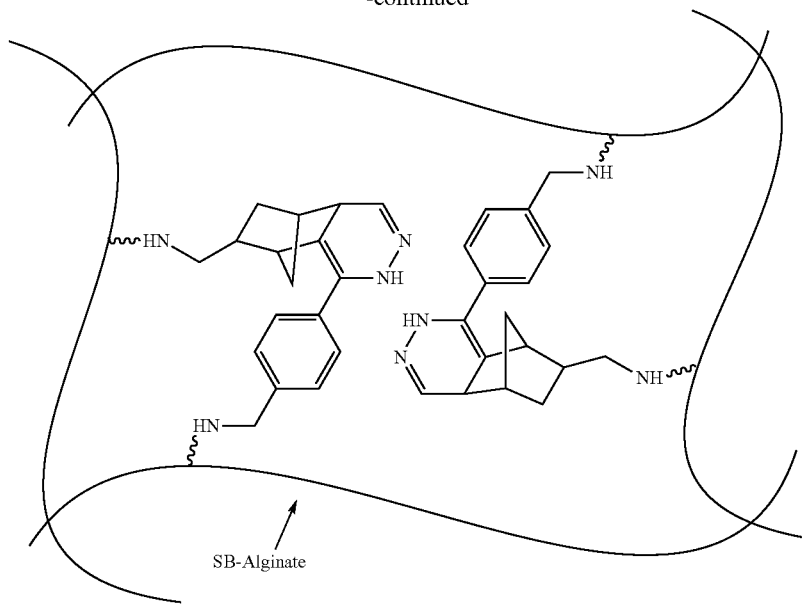

Another aspect of the present invention relates to a capsule comprising the hydrogel of the present invention and a therapeutic agent encapsulated in the hydrogel.

A "capsule," as used herein, refers to a particle having a mean diameter of about 150 μm to about 5 cm. In one embodiment, the capsules of the present invention have a mean diameter of about 150 μm to about 8 mm. A "microcapsule" as referred to herein has a mean diameter of about 150 μm to about 1000 μm. The capsule or microcapsule is formed of the polymers, polymeric matrix, or hydrogels as described herein. The capsule may comprise a cross-linked hydrogel core that is surrounded by one or more polymeric shells, one or more cross-linked hydrogel layers, a cross-linked hydrogel coating, or a combination thereof. The capsule can be any suitable shape for cell encapsulation or encapsulation of a therapeutic agent. Useful shapes include spheres, sphere-like shapes, spheroids, spheroid-like shapes, ellipsoids, ellipsoid-like shapes, stadiumoids, stadiumoid-like shapes, disks, disk-like shapes, cylinders, cylinder-like shapes, rods, rod-like shapes, cubes, cube-like shapes, cuboids, cuboid-like shapes, toruses, torus-like shapes, and flat and curved surfaces.

When used for cell encapsulation, the capsule may contain one or more cells dispersed in the cross-linked hydrogel, thereby "encapsulating" the cells. The rate of molecules entering the capsule necessary for cell viability and the rate of therapeutic products and waste material exiting the capsule membrane can be selected by modulating capsule permeability. Capsule permeability can also be modified to limit entry of immune cells, antibodies, and cytokines into the capsule. Generally, known methods of forming hydrogel capsules can produce capsules having limited entry of immune cells, antibodies, and cytokines into the capsule. Since different cell types have different metabolic requirements, the permeability of the capsule can be optimized based on the cell type encapsulated in the hydrogel. The diameter of the capsules is an important factor that influences both the immune response towards the cell capsules as well as the mass transport across the capsule membrane.

The therapeutic agent can be any biologically reactive agent including, for example, and without limitation, therapeutic proteins, peptides, antibodies or fragments thereof, antibody mimetics, and other binding molecules, nucleic acids, small molecules, hormones, growth factors, angiogenic factors, cytokines, and anti-inflammatory agents.

The types of drugs (or therapeutic agents) that can be delivered using the capsules and microcapsules as described herein are numerous, and include both small molecular weight compounds in the size range from 100 daltons to about 1,000 daltons as well as the larger macromolecular drugs, such as peptide and protein drugs in the size range from about 1,000 daltons to about 100,000 daltons, and beyond. The capsules made of the polymers and hydrogels described herein are particularly well suited to deliver drugs having relatively low effective doses, e.g., in the micrograms/day, nanograms/day, and even picograms/day range.

Protein and/or peptide therapeutic agents which may be contained within the capsule for delivery upon implantation in a subject include, without limitation, peptide hormones such as insulin, glucagon, parathyroid hormone, calcitonin, vasopression, renin, prolactin, growth hormone, the gonadotropins, including chorionic gonadotropin, follicle stimulating hormone, thyroid stimulating hormone, and luteinizing hormone; physiologically active enzymes such as transferases, hydrolases, lyases, isomerases, phosphatases, glycosidases, superoxide dismutase, factor VIII, plasminogen activators; and other therapeutic agents including protein factors such as epidermal growth factor, insulin-like growth factor, tumour necrosis factor, transforming growth factors, fibroblast growth factors, platelet-derived growth factors, erythropoietin, colony stimulating factors, bone morphogenetic proteins, interleukins, and interferons. Non-protein macromolecules, particularly including polysaccharides, nucleic acid polymers, and therapeutic secondary metabolites, including plant products such as vinblastine, vincristine, taxol, and the like may also be delivered using the present system. Small molecular weight compounds may also be delivered.

In one embodiment, the therapeutic agent is a biological agent produced and/or secreted or released from tissue and/or a preparation of cells encapsulated within or residing within the capsule as described herein. The cells may comprise naturally occurring or genetically engineered cells which may be in the form of single cells and/or cell clusters. In one embodiment, the cells within the capsule secrete one or more biological factors that are useful in the treatment of a disease or condition. These factors are secreted from the cells, released from the hydrogel or polymeric layer of the capsule, and are delivered to or diffuse to surrounding target cells, tissue, or organ in need thereof. Suitable cells include, without limitation, one or more cell types selected from the group consisting of smooth muscle cells, cardiac myocytes, platelets, epithelial cells, endothelial cells, urothelial cells, fibroblasts, embryonic fibroblasts, myoblasts, chondrocytes, chondroblasts, osteoblasts, osteoclasts, keratinocytes, hepatocytes, bile duct cells, pancreatic islet cells, thyroid, parathyroid, adrenal, hypothalamic, pituitary, ovarian, testicular, salivary gland cells, adipocytes, stem cells, including mesenchymal stem cells, neural cells, endothelial progenitor cells, hematopoietic cells, embryonic stem cells, induced pluripotent stem cells, or cells derived from such stem cells. Suitable cells include xenogeneic, autologous, or allogeneic cells. Cells can be primary cells or cells derived from the culture and expansion of a cell obtained from a subject. Cells can also be immortalized cells.

In one embodiment, the cells are insulin secreting cells. An insulin secreting cells is a cell that produces insulin, preferably in response to glucose levels. Insulin secreting cells include pancreatic islet cells, insulin-producing cells derived from stem cells, and cells genetically engineered to produce insulin. In one embodiment, the cells are mammalian insulin secreting cells. In one embodiment, the cells are human insulin secreting cells. In one embodiment, the cells are human pancreatic islet cells. Islet cells are endocrine cells derived from a mammalian pancreas. Islet cells include alpha cells that secrete glucagon, beta cells that secrete insulin and amylin, delta cells that secrete somatostatin, PP cells that secrete pancreatic polypeptide, or epsilon cells that secrete ghrelin. The term includes homogenous and heterogeneous populations of these cells. In preferred embodiments, a population of islet cells contains at least beta cells.

Methods of isolating pancreatic islet cells that are suitable for encapsulation in the capsule as described herein are known in the art. See e.g. Field et al., Transplantation 61:1554 (1996); Linetsky et al., Diabetes 46:1120 (1997), which are incorporated by reference in their entirety). Fresh pancreatic tissue can be divided by mincing, teasing, comminution and/or collagenase digestion. The islets can then be isolated from contaminating cells and materials by washing, filtering, centrifuging or picking procedures. Methods and apparatus for isolating and purifying islet cells are described in U.S. Pat. No. 5,447,863 to Langley, U.S. Pat. No. 5,322,790 to Scharp et al., U.S. Pat. No. 5,273,904 to Langley, and U.S. Pat. No. 4,868,121 to Scharp et al., which are hereby incorporated by reference in their entirety. The isolated pancreatic cells may optionally be cultured prior to inclusion in the hydrogel capsule using any suitable method of culturing islet cells as is known in the art. See e.g., U.S. Pat. No. 5,821,121 to Brothers which is hereby incorporated by reference in its entirety. Isolated cells may be cultured in a medium under conditions that helps to eliminate antigenic components. Insulin-producing cells can also be derived from stem cells and cell lines and can be cells genetically engineered to produce insulin. See e.g., U.S. Patent Application Publication No. 20040005301 to Goldman and U.S. Pat. No. 9,624,472 to Firpo, which are hereby incorporated by reference in their entirety.

As noted above, suitable cells include progenitor and/or stem cells. Suitable stem cells may be pluripotent, multipotent, oligopotent, or unipotent cells or cell populations, and include embryonic stem cells, epiblast cells, primitive ectoderm cells, and primordial germ cells. In another embodiment, suitable stem cells also include induced pluripotent stem (iPS) cells, which are pluripotent stem cells derived from a non-pluripotent cell. See Zhou et al., *Cell Stem Cell* 4:381-384 (2009); Yu et al., *Science* 324(5928):797-801 (2009); Yu et al., *Science* 318(5858):1917-20 (2007); Takahashi et al., *Cell* 131:861-72 (2007); and Takahashi and Yamanaka, *Cell* 126:663-76 (2006), which are hereby incorporated by reference in their entirety. In accordance with this embodiment, the capsule may further comprise the growth and differentiation factors suitable for promoting stem cell differentiation into a desired population of cells capable of producing and releasing the therapeutic agent of interest.

Suitable cells for encapsulation in the capsule described herein can be derived from any animal capable of generating the desired cells. The animals from which the cells are harvested may be vertebrate or invertebrate, mammalian or non-mammalian, human or non-human. Examples of animal sources include, but are not limited to, primate, rodent, canine, feline, equine, bovine, or porcine. The cells may be obtained from or comprise a primary cell preparation or immortalized cells preparations. The encapsulated cells may be isolated from the same species as the implant recipient or from a different species than the implant recipient.

In some embodiments, the capsule described herein comprises a cell density between approximately $1\times10^5$ or $1\times10^6$ cells/ml to about $1\times10^{10}$ cells/mL or more. In one embodiment, the cell holding capacity of the capsule is based, at least in part, on the size of the capsule. In one embodiment, the capsule membrane prohibits cells in the hydrogel from escaping the capsule. The cells are capable of surviving in vivo in the capsule for at least a month, two months, three months, four months, five months, six months, seven months, eight months, nine months, ten months, eleven months, twelve months or a year or more with a functionality that represents at least about 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% of the function expressed at the time the cells are/were introduced into the capsule or at the time the cells fully develop and/or mature in the capsule, e.g., implantation of progenitor cells which need to further develop or mature to functional cells in vivo. In some embodiments, the cells or cell preparation in the system expand within the capsule to increase cell density and/or cell function upon implantation of the system in vivo.

When the capsule contains cells or a cell preparation, additional cell specific growth and/or differentiation factors may be added to the hydrogel or polymeric solution to enhance cell growth, differentiation, and survival. These factors include supplements (e.g., glutamine, non-essential amino acids), growth factors (e.g., epidermal growth factors, fibroblast growth factors, transforming growth factor/bone morphogenetic proteins, platelet derived growth factors, insulin growth factors, cytokines), extracellular matrix proteins (e.g., fibronectin, laminin, heparin, collagen, glycosaminoglycan, proteoglycan, elastin, chitin derivatives, fibrin, and fibrinogen), angiogenic factors (e.g., FGF, bFGF, acid FGF (aFGF), FGF-2, FGF-4, EGF, PDGF, TGF-beta, angiopoietin-1, angiopoietin-2, placental growth factor (PlGF), VEGF, and PMA (phorbol 12-myristate 13-acetate)), and signaling factors and/or transcription factors.

Another aspect of the present invention is directed to a method of delivering a therapeutic agent to a subject. This method involves administering the capsule comprising the hydrogel and a therapeutic agent encapsulated by the hydrogel to the subject.

The capsule described herein can be employed for treating a variety of diseases and conditions requiring a continuous supply of biologically active substance or substances to the subject. The capsule may contain homogenous or heterogenous mixtures of biologically active agents and/or cells, or cells producing one or more biologically active substances of interest. The biologically active agents and/or cells are wholly encapsulated within the hydrogel layer of the capsule. Such a semi-permeable outer layer allows the encapsulated biologically active substance of interest (e.g., insulin, glucagon, pancreatic polypeptide, and the like in the case of treating diabetes) to pass out of the system, making the active substance available to target cells outside the system and in the recipient subject's body. In one embodiment, the capsule membrane is a semi-permeable membrane that allows nutrients naturally present in the subject to pass through the membrane to provide essential nutrients to cells present in the hydrogel. At the same time, such a semi-permeable membrane prevents the recipient subject's cells, more particularly, their immune system cells, from passing through and into the capsule to harm the cells in the system. For example, in the case of diabetes, this approach can allow glucose and oxygen (e.g., contained within the body) to stimulate insulin-producing cells of the capsule to release insulin as required by the body in real time while preventing host immune system cells from recognizing and destroying the implanted cells.

Another aspect of the present invention is directed to a method of treating a diabetic subject. This method involves selecting a subject having diabetes, and implanting the capsule comprising the hydrogel and a therapeutic agent encapsulated by the hydrogel to the subject. In accordance with this embodiment, the capsule contains a preparation of insulin secreting cells encapsulated in the hydrogel, and the therapeutic agent delivered to the subject is insulin.

In accordance with one embodiment of this aspect of the invention, the subject having diabetes has type-1 diabetes (also called juvenile diabetes). In another embodiment, the subject has type-2 diabetes. In another embodiment, the subject has Maturity Onset Diabetes of the Young (MODY).

The capsule can be surgically implanted into subjects. In one embodiment, the capsule is implanted using minimally invasive surgical techniques such as laparoscopy. The capsule can be implanted percutaneously, subcutaneously, intraperitoneally, intrathoracically, intramuscularly, intraarticularly, intraocularly, or intracerebrally depending on the therapeutic agent being delivered, condition to be treated, and tissue or organ targeted for delivery.

Subjects amenable to treatment with the capsule according to the present invention include mammals (e.g., a human, horse, pig, rabbit, dog, sheep, goat, non-human primate, cow, cat, guinea pig or rodent), fish, birds, reptiles, and amphibians. The term does not denote a particular age or sex. Thus, adult and newborn subjects, as well as fetuses, whether male or female, are intended to be covered. In some embodiments, the subject is afflicted with a disease or disorder. The term "subject" includes human and veterinary subjects.

Another aspect of the present invention is directed to surfaces coated with the polymers, polymeric networks, and hydrogels described herein. The polymers, polymeric networks, and hydrogels can be advantageously used to coat surfaces of a variety of devices including, for example, medical devices to provide biocompatible, non-fibrotic, and non-fouling surfaces. Accordingly, in another aspect, the invention provides devices and materials having a surface (i.e., one or more surfaces) to which have been applied (e.g., coated, covalently coupled, ionically associated, hydrophobically associated) one or more polymers, polymeric networks, or hydrogels of the invention. Representative devices and carriers that may be advantageously treated or coated with the polymers and polymeric networks described herein include: particles (e.g., nanoparticles) having a surface treated with, modified to include, or incorporating the polymers or polymeric network described herein; a drug carrier having a surface treated with, modified to include, or incorporating the polymers or polymeric network described herein; a non-viral gene delivery system having a surface treated with, modified to include, or incorporating the polymers or polymeric network described herein; a biosensor having a surface treated with, modified to include, or incorporating the polymers or polymeric network described herein; devices for bioprocesses or bioseparations, such as membranes for microbial suspension, hormone separation, protein fractionation, cell separation, waste water treatment, oligosaccharide bioreactors, protein ultrafiltration, and dairy processing having a surface treated with, modified to include, or incorporating the polymers or polymeric network described herein; implantable sensor having a surface treated with, modified to include, or incorporating the polymers or polymeric network described herein; subcutaneous sensor having a surface treated with, modified to include, or incorporating the polymers or polymeric network described herein; an implant, such as a breast implant, cochlear implant, and dental implant having a surface treated with, modified to include, or incorporating the polymers or polymeric network described herein; a tissue scaffold having a surface treated with, modified to include, or incorporating the polymers or polymeric network described herein; implantable medical devices, such as an artificial joint, artificial heart valve, artificial blood vessel, pacemaker, left ventricular assist device (LVAD), artery graft, and stent having a surface treated with, modified to include, or incorporating the polymers or polymeric network described herein; and medical devices, such as an ear drainage tube, feeding tube, glaucoma drainage tube, hydrocephalous shunt, keratoprosthesis, nerve guidance tube, urinary catheter, tissue adhesive, and x-ray guide having a surface treated with, modified to include, or incorporating the polymers or polymeric network described herein.

The capsules, products, devices, and surfaces made from or coated with the polymers or polymeric network as described herein can remain substantially free of fibrotic effects, or can continue to exhibit a reduced foreign body response, for 2 weeks, 3 weeks, 4 weeks, 5 weeks, 6 weeks, 7 weeks, 8 weeks, 9 weeks, 10 weeks, 2 months, 3 months, 4 months, 5 months, 6 months, 7 months, 8, months, 9 months, 10 months, 11 months, 1 year, 2 years, or longer after administration or implantation in a subject.

Methods of Synthesis

Another aspect of the present invention relates to methods of preparing the monomers and polymers as described herein.

Accordingly, the polymers comprising one or more monomers of Formula (I) can be prepared according to Schemes 1-2 outlined below.

Scheme 1

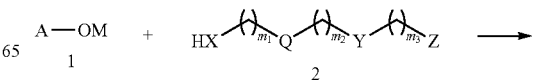

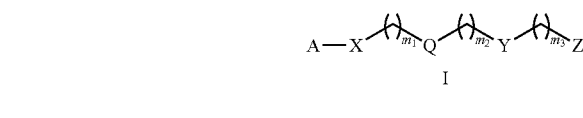

M is metal

Reaction between the saccharide salt (1) and compound (2) leads to formation of the saccharide polymers comprising one or more covalently modified monomers of Formula (I).

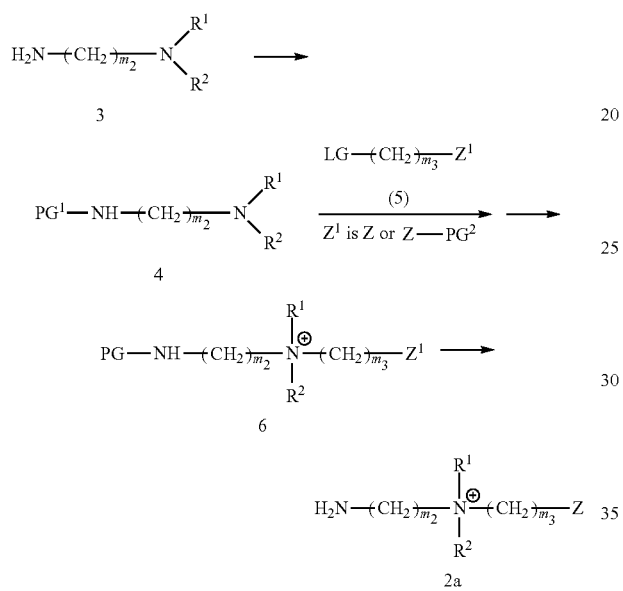

Amine (3) can be protected using a suitable protecting group. Coupling of the protected amine (4) with the compound (5) leads to formation of the compound (6). The coupling reaction can be carried out in a variety of solvents, for example in acetonitrile, methanol, ethanol, methylene chloride ($CH_2Cl_2$), tetrahydrofuran (THF), dimethylformamide (DMF), or other such solvents or in the mixture of such solvents. During the coupling process, the non-participating carboxylic acids on the compound 5 can be protected by a suitable protecting group which can be selectively removed at a later time if desired. A detailed description of these groups and their selection and chemistry is contained in "The Peptides, Vol 3", Gross and Meinenhofer, Eds., Academic Press, New York, 1981, which is hereby incorporated by reference in its entirety. Thus, useful protective groups for the amino group are benzyloxycarbonyl (Cbz), t-butyloxycarbonyl (t-BOC), 2,2,2-trichloroethoxycarbonyl (Troc), t-amyloxycarbonyl, 4-methoxybenzyloxycarbonyl, 2-(trichlorosilyl)ethoxycarbonyl, 9-fluorenylmethoxy carbonyl (Fmoc), phthaloyl, acetyl (Ac), formyl, trifluoroacetyl, and the like. Removal of the protecting groups leads to formation of compound (2a).

Another aspect of the present invention relates to methods of synthesizing monomers of Formula (III). These monomers can be prepared according to Schemes 3-5 outlined below.

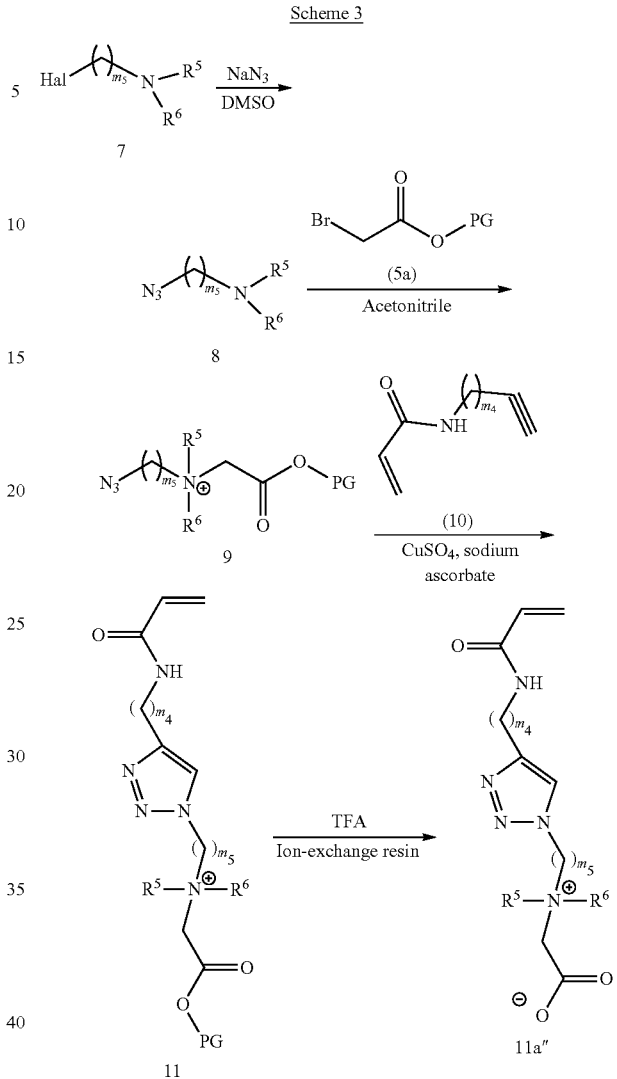

Reaction between compound (7) and sodium azide leads to formation of azide (8). The reaction can be carried out in a variety of solvents, for example in dimethyl sulfoxide (DMSO), methanol, ethanol, dimethylformamide (DMF), or other such solvents or in the mixture of such solvents. Reaction between the azide (8) and the compound (5a) leads to formation of the compound (9). The reaction can be carried out in a variety of solvents, for example in acetonitrile, methanol, ethanol, methylene chloride ($CH_2Cl_2$), tetrahydrofuran (THF), dimethylformamide (DMF), or other such solvents or in the mixture of such solvents. During this process, the non-participating carboxylic acids on the compound 5a can be protected by a suitable protecting group which can be selectively removed at a later time if desired. A detailed description of these groups and their selection and chemistry is contained in "The Peptides, Vol. 3", Gross and Meinenhofer, Eds., Academic Press, New York, 1981, which is hereby incorporated by reference in its entirety. Thus, useful protective groups for the amino group are benzyloxycarbonyl (Cbz), t-butyloxycarbonyl (t-BOC), 2,2,2-trichloroethoxycarbonyl (Troc), t-amyloxycarbonyl, 4-methoxybenzyloxycarbonyl, 2-(trichlorosilyl)ethoxycarbonyl, 9-fluorenylmethoxycarbonyl (Fmoc), phthaloyl, acetyl (Ac), formyl, trifluoroacetyl, and the like.

Reaction between azide (9) and alkyne (10) leads to formation of triazole (11). The reaction can be carried out in a variety of solvents, for example in dimethyl sulfoxide (DMSO), methanol, ethanol, dimethylformamide (DMF), or other such solvents or in the mixture of such solvents. Removal of the protecting groups leads to formation of compound (IIIa").

Scheme 4

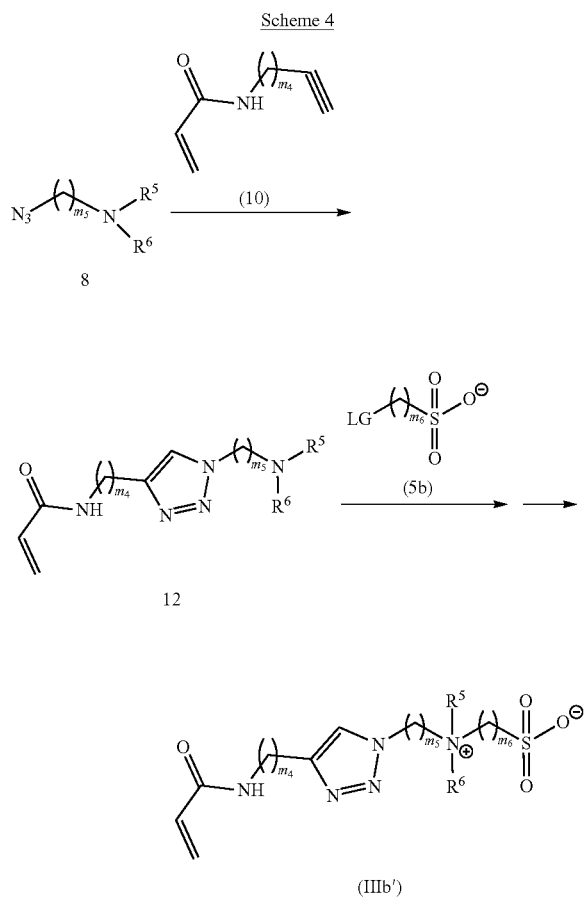

Reaction between the azide (8) and alkyne (10) leads to formation of the triazole (12). The reaction can be carried out in a variety of solvents, for example in acetonitrile, methanol, ethanol, methylene chloride ($CH_2Cl_2$), tetrahydrofuran (THF), dimethylformamide (DMF), or other such solvents or in the mixture of such solvents. Reaction between the azide (12) and the compound (5b) leads to formation of the monomer (IIIb'). The reaction can be carried out in a variety of solvents, for example in acetonitrile, methanol, ethanol, methylene chloride ($CH_2Cl_2$), tetrahydrofuran (THF), dimethylformamide (DMF), or other such solvents or in the mixture of such solvents.

Scheme 5

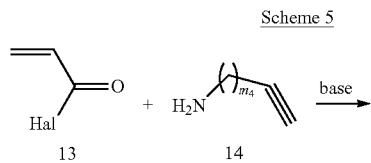

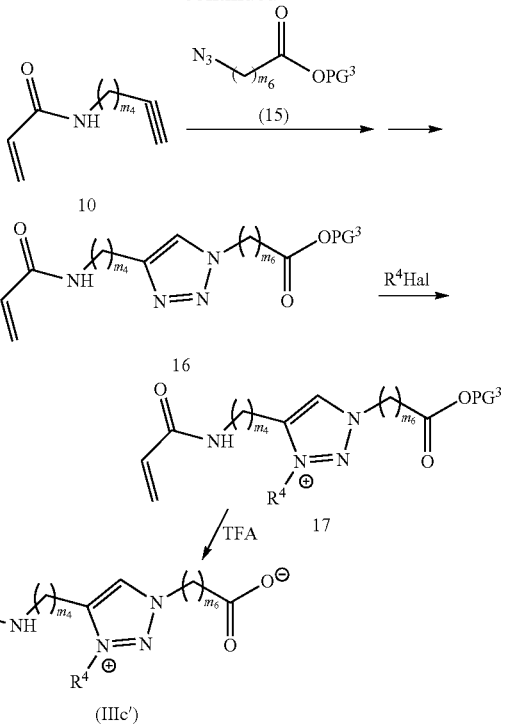

Alkyne (10) can be prepared by reacting compound (13) with alkyne (14) in the presence of a base. This reaction can be carried out in a variety of solvents, for example in acetonitrile, methanol, ethanol, methylene chloride ($CH_2Cl_2$), tetrahydrofuran (THF), dimethylformamide (DMF), or other such solvents or in the mixture of such solvents. Reaction between the alkyne (10) and azide (15) leads to formation of the triazole (16). During this process, the non-participating carboxylic acids on the compound 5a can be protected by a suitable protecting group which can be selectively removed at a later time if desired. A detailed description of these groups and their selection and chemistry is contained in "The Peptides, Vol 3", Gross and Meinenhofer, Eds., Academic Press, New York, 1981, which is hereby incorporated by reference in its entirety. Thus, useful protective groups for the amino group are benzyloxycarbonyl (Cbz), t-butyloxycarbonyl (t-BOC), 2,2,2-trichloroethoxycarbonyl (Troc), t-amyloxycarbonyl, 4-methoxybenzyloxycarbonyl, 2-(trichlorosilyl)ethoxycarbonyl, 9-fluorenylmethoxycarbonyl (Fmoc), phthaloyl, acetyl (Ac), formyl, trifluoroacetyl, and the like. The reaction can be carried out in a variety of solvents, for example in acetonitrile, methanol, ethanol, methylene chloride ($CH_2Cl_2$), tetrahydrofuran (THF), dimethylformamide (DMF), or other such solvents or in the mixture of such solvents. During this process, the non-participating carboxylic acids on the compound 15 can be protected by a suitable protecting group which can be selectively removed at a later time if desired. A detailed description of these groups and their selection and chemistry is contained in "The Peptides, Vol. 3", Gross and Meinenhofer, Eds., Academic Press, New York, 1981, which is hereby incorporated by reference in its entirety. Thus, useful protective groups for the amino group are benzyloxycarbonyl (Cbz), t-butyloxycarbonyl (t-BOC), 2,2,2-trichloroethoxycarbonyl (Troc), t-amyloxycarbonyl, 4-methoxybenzyloxycarbonyl, 2-(trichlorosilyl)ethoxycarbonyl, 9-fluorenylmethoxycarbonyl (Fmoc), phthaloyl, acetyl (Ac), formyl, trifluoroacetyl, and the like. Azide (12) can be alkylated with alkyl halide (R⁴Hal) to form the compound (17). The reaction can be carried out in a variety of solvents, for example in acetonitrile, methanol, ethanol, methylene chloride ($CH_2Cl_2$), tetrahydrofuran (THF), dimethylformamide (DMF), or other such solvents or in the mixture of such solvents. Removal of the protecting groups leads to formation of monomer (IIIc').

Another aspect of the invention relates to a process for preparation of a monomer of Formula (IIIa'):

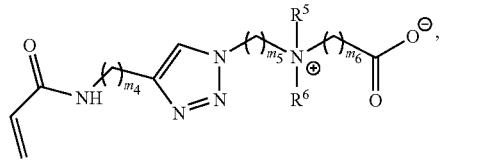
(IIIa')

where
m$_4$ is 1 to 50;
m$_5$ is 0 to 10;
m$_6$ is 1 to 50;
R$^5$ is $C_{1-20}$ alkyl; and
R$^6$ is $C_{1-20}$ alkyl.

This process includes:
providing a compound of Formula (V):

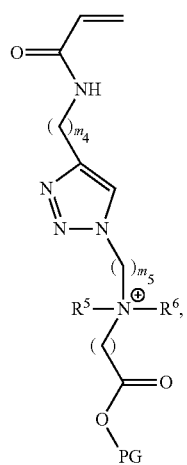
(V)

where
PG is a suitable protecting group; and
forming the monomer of Formula (IIIa') from compound of Formula (V).

Any suitable protecting group (PG) can be used. A detailed description of these groups and their selection and chemistry is contained in "The Peptides, Vol. 3", Gross and Meinenhofer, Eds., Academic Press, New York, 1981, which is hereby incorporated by reference in its entirety.

In one embodiment, PG is selected form the group consisting of t-butyloxycarbonyl (t-BOC), 9-fluorenylmethoxycarbonyl (Fmoc), benzyloxycarbonyl (Cbz), 2,2,2-trichloroethoxycarbonyl (Troc), t-amyloxycarbonyl, 4-methoxybenzyloxycarbonyl, 2-(trichlorosilyl)ethoxycarbonyl, phthaloyl, acetyl (Ac), formyl, and trifluoroacetyl.

One embodiment relates to a process for preparation of a monomer of Formula (IIIa'), wherein said forming the monomer of Formula (IIIa') comprises reacting the compound of Formula (V) with a suitable protecting group removing agent.

Another embodiment relates to a process for preparation of a monomer of Formula (IIIa') that further includes:
providing a compound of Formula (VI):

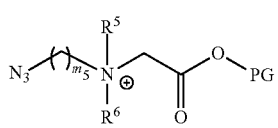
(VI)

and
forming the compound of Formula (V) from the compound of Formula (VI).

A further embodiment relates to a process for preparation of a monomer of Formula (IIIa'), wherein said forming the compound of Formula (V) comprises reacting the compound of Formula (VI) with the compound of Formula (VII):

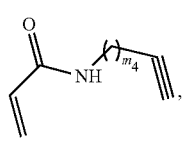
(VII)

under conditions effective to produce the compound of Formula (V).

Another embodiment relates to a process for preparation of a monomer of Formula (IIIa') that further includes:
providing a compound of Formula (VIII):

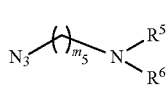
(VIII)

and
forming the compound of Formula (VI) from the compound of Formula (VIII).

A further embodiment relates to a process for preparation of a monomer of Formula (IIIa'), wherein said forming the compound of Formula (VI) comprises reacting the compound of Formula (VIII) with the compound of Formula (IX):

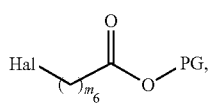
(IX)

wherein Hal is halogen,
under conditions effective to produce the compound of Formula (VI).

Yet another embodiment relates to a process for preparation of a monomer of Formula (IIIa') that further includes:
providing a compound of Formula (X):

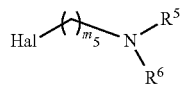
(X)

and
forming the compound of Formula (VIII) from the compound of Formula (X).

A further embodiment relates to a process for preparation of a monomer of Formula (IIIa'), wherein said forming the compound of Formula (VIII) comprises reacting the compound of Formula (X) with metal azide ($MN_3$), wherein M is any suitable metal, under conditions effective to produce the compound of Formula (VIII).

Yet another embodiment relates to a process for preparation of a monomer of Formula (IIIa') that further includes:
providing a compound of Formula (XI):

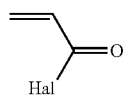
(XI)

and
forming the compound of Formula (VII) from the compound of Formula (XI).

A further embodiment relates to a process for preparation of a monomer of Formula (IIIa'), wherein said forming the compound of Formula (VII) comprises reacting the compound of Formula (XI) with the compound of Formula (XII):

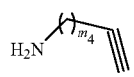
(XII)

under conditions effective to produce the compound of Formula (VII).

Another aspect of the invention relates to a process for preparation of a monomer of Formula (IIIb'):

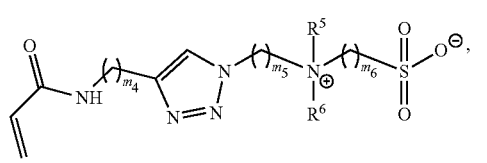
(IIIb')

where
$m_4$ is 1 to 50;
$m_5$ is 0 to 10;
$m_6$ is 1 to 50;
$R^5$ is $C_{1-20}$ alkyl; and
$R^6$ is $C_{1-20}$ alkyl.

This process includes:
providing a compound of Formula (XIII):

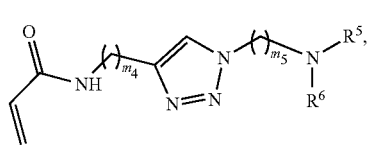
(XIII)

and
forming the monomer of Formula (IIIb') from compound of Formula (XIII).

One embodiment relates to a process for preparation of a monomer of Formula (IIIb'), wherein said forming the monomer of Formula (IIIb') comprises reacting the compound of Formula (XIII) with a compound of Formula (XIV):

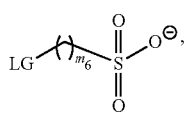
(XIV)

under conditions effective to produce the monomer of Formula (IIIb').

Another embodiment relates to a process for preparation of a monomer of Formula (IIIb') that further includes:
providing a compound of Formula (XV):

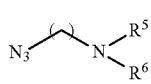
(XV)

and
forming the compound of Formula (XIII) from the compound of Formula (XV).

A further embodiment relates to a process for preparation of a monomer of Formula (IIIb'), wherein said forming the compound of Formula (XIII) comprises reacting the compound of Formula (XV) with the compound of Formula (VII):

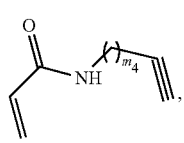
(VII)

under conditions effective to produce the compound of Formula (XIII).

Yet another embodiment relates to a process for preparation of a monomer of Formula (IIIb') that further includes:
providing a compound of Formula (XI):

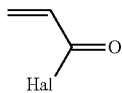

and
forming the compound of Formula (VII) from the compound of Formula (XI).

A further embodiment relates to a process for preparation of a monomer of Formula (IIIb'), wherein said forming the compound of Formula (VII) comprises reacting the compound of Formula (XI) with the compound of Formula (XII):

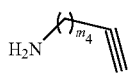

under conditions effective to produce the compound of Formula (VII).

Another aspect of the invention relates to a process for preparation of a monomer of Formula (IIIc'):

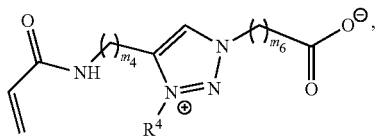

where
$m_4$ is 1 to 50;
$m_6$ is 1 to 50;
$R^4$ is $C_{1-20}$ alkyl;
This process includes:
providing a compound of Formula (XVI):

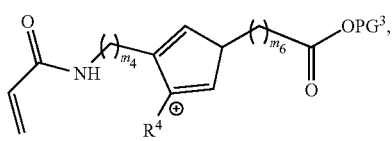

and where
PG is a suitable protecting group; and
forming the monomer of Formula (IIIc') from compound of Formula (XVI).

Any suitable protecting group (PG) can be used. A detailed description of these groups and their selection and chemistry is contained in "The Peptides, Vol. 3", Gross and Meinenhofer, Eds., Academic Press, New York, 1981, which is hereby incorporated by reference in its entirety.

In one embodiment, PG is selected form the group consisting of t-butyloxycarbonyl (t-BOC), 9-fluorenylmethoxycarbonyl (Fmoc), benzyloxycarbonyl (Cbz), 2,2,2-trichloroethoxycarbonyl (Troc), t-amyloxycarbonyl, 4-methoxybenzyloxycarbonyl, 2-(trichlorosilyl)ethoxycarbonyl, phthaloyl, acetyl (Ac), formyl, and trifluoroacetyl.

One embodiment relates to a process for preparation of a monomer of Formula (IIIc'), wherein said forming the monomer of Formula (IIIc') comprises reacting the compound of Formula (XVI) with a suitable protecting group removing agent.

Another embodiment relates to a process for preparation of a monomer of Formula (IIIc') that further includes:
providing a compound of Formula (XVII):

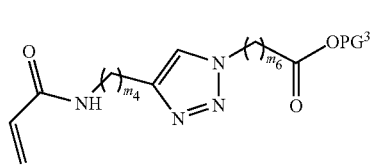

and
forming the compound of Formula (XVI) from the compound of Formula (XVII).

A further embodiment relates to a process for preparation of a monomer of Formula (IIIc'), wherein said forming the compound of Formula (XVI) comprises reacting the compound of Formula (XVII) with the compound of Formula (XVIII):

$$R^4Hal \qquad (XVIII),$$

under conditions effective to produce the compound of Formula (XVI).

Another embodiment relates to a process for preparation of a monomer of Formula (IIIc') that further includes:
providing a compound of Formula (VII):

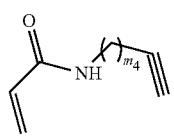

and
forming the compound of Formula (XVII) from the compound of Formula (VII).

A further embodiment relates to a process for preparation of a monomer of Formula (IIIc'), wherein said forming the compound of Formula (XVII) comprises reacting the compound of Formula (VII) with the compound of Formula (XIX):

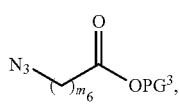

under conditions effective to produce the compound of Formula (XVII).

Yet another embodiment relates to a process for preparation of a monomer of Formula (IIIc') that further includes:
providing a compound of Formula (XI):

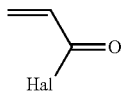
(XI)

and
forming the compound of Formula (VII) from the compound of Formula (XI).

A further embodiment relates to a process for preparation of a monomer of Formula (IIIc'), wherein said forming the compound of Formula (VII) comprises reacting the compound of Formula (XI) with the compound of Formula (XII):

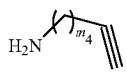
(XII)

under conditions effective to produce the compound of Formula (VII).

Another aspect of the invention relates to a process for preparation of a compound of Formula (XXa):

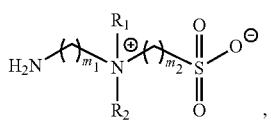
(XXa)

wherein
$m_1$ is 1 to 50;
$m_2$ is 1 to 10;
$R_1$ is $C_{1-20}$ alkyl; and
$R_2$ is $C_{1-20}$ alkyl.
This process includes:
providing a compound of Formula (XXI):

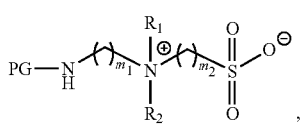
(XXI)

wherein
PG is a suitable protecting group; and
forming the compound of Formula (XXa) from compound of Formula (XXI).

Any suitable protecting group (PG) can be used. A detailed description of these groups and their selection and chemistry is contained in "The Peptides, Vol. 3", Gross and Meinenhofer, Eds., Academic Press, New York, 1981, which is hereby incorporated by reference in its entirety.

In one embodiment, PG is selected form the group consisting of t-butyloxycarbonyl (t-BOC), 9-fluorenylmethoxycarbonyl (Fmoc), benzyloxycarbonyl (Cbz), 2,2,2-trichloroethoxycarbonyl (Troc), t-amyloxycarbonyl, 4-methoxybenzyloxycarbonyl, 2-(trichlorosilyl)ethoxycarbonyl, phthaloyl, acetyl (Ac), formyl, and trifluoroacetyl.

One embodiment relates to a process for preparation of a compound of Formula (XXa), wherein said forming the compound of Formula (XXa) comprises reacting the compound of Formula (XXI) with a suitable protecting group removing agent.

Another embodiment relates to a process for preparation of a compound of Formula (XXa) that further includes:
providing a compound of Formula (XXII):

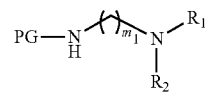
(XXII)

and
forming the compound of Formula (XXI) from the compound of Formula (XXII).

A further embodiment relates to a process for preparation of a compound of Formula (XXa), wherein said forming the compound of Formula (XXI) comprises reacting the compound of Formula (XXII) with the compound of Formula (XXIII):

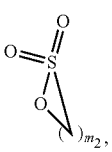
(XXIII)

under conditions effective to produce the compound of Formula (XXI).

Yet another embodiment relates to a process for preparation of a compound of Formula (XXa) that further includes:
providing a compound of Formula (XXIV):

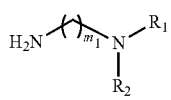
(XXIV)

and
forming the compound of Formula (XXII) from the compound of Formula (XXIV).

A further embodiment relates to a process for preparation of a compound of Formula (XXa), wherein said forming the compound of Formula (XXII) comprises reacting the compound of Formula (XXIV) with a suitable protecting group introducing agent, under conditions effective to produce the compound of Formula (XXII).

Another aspect of the invention relates to a process for preparation of a compound of Formula (XXb):

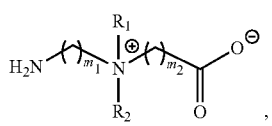
(XXb)

wherein
m₁ is 1 to 50;
m₂ is 1 to 10;
$R_1$ is $C_{1-20}$ alkyl;
$R_2$ is $C_{1-20}$ alkyl.
This process includes:
providing a compound of Formula (XXV):

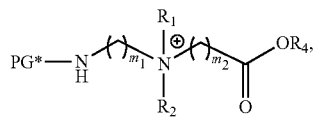

(XXV)

wherein
PG* is a suitable protecting group;
$R_4$ is $C_{1-6}$ alkyl, and
forming the compound of Formula (XXb) from compound of Formula (XXV).

Any suitable protecting group (PG*) can be used. A detailed description of these groups and their selection and chemistry is contained in "The Peptides, Vol. 3", Gross and Meinenhofer, Eds., Academic Press, New York, 1981, which is hereby incorporated by reference in its entirety.

In one embodiment PG* is selected form the group consisting of t-butyloxycarbonyl (t-BOC), 9-fluorenylmethoxycarbonyl (Fmoc), benzyloxycarbonyl (Cbz), 2,2,2-trichloroethoxycarbonyl (Troc), t-amyloxycarbonyl, 4-methoxybenzyloxycarbonyl, 2-(trichlorosilyl)ethoxycarbonyl, phthaloyl, acetyl (Ac), formyl, and trifluoroacetyl.

Another embodiment relates to a process for preparation of a compound of Formula (XXb), wherein said forming the compound of Formula (XXb) comprises reacting the compound of Formula (XXV) with a suitable protecting group removing agent.

Another embodiment relates to a process for preparation of a compound of Formula (XXb) that further includes:
providing a compound of Formula (XXII):

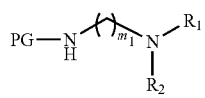

(XXII)

and
forming the compound of Formula (XXV) from the compound of Formula (XXII).

Another embodiment relates to a process for preparation of a compound of Formula (XXb), wherein said forming the compound of Formula (XXV) comprises reacting the compound of Formula (XXII) with a compound of Formula (XXVI):

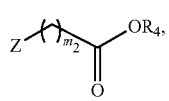

(XXVI)

wherein Z is halogen.

Yet another embodiment relates to a process for preparation of a compound of Formula (XXb) that further includes:
providing a compound of Formula (XXIV):

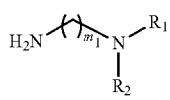

(XXIV)

and
forming the compound of Formula (XXII) from the compound of Formula (XXIV).

A further embodiment relates to a process for preparation of a compound of Formula (XXb), wherein said forming the compound of Formula (XXII) comprises reacting the compound of Formula (XXIV) with a suitable protecting group introducing agent, under conditions effective to produce the compound of Formula (XXII).

EXAMPLES

Materials for Examples 1-6

Di-tert-butyl dicarbonate, triethylamine, N,N-dimethylethylenediamine, barium chloride, magnesium sulfate, magnesium chloride hexahydrate, HEPES buffer, diethyl ether, ethyl alcohol, acetonitrile, and dichloromethane (DCM) were obtained from Sigma-Aldrich. 2-Chloro-4,6-dimethoxy-1,3,5-triazine (CDMT), N-methylmorpholine (NMM), 1,3-propanesultone, and trifluoroacetic acid (TFA) were purchased from the Alfa Aesar. All the sodium alginates including VLVG (>60% G, 25 kDa MW), SLG20 (>60% G, 75-220 kDa MW), and SLG100 (>60% G, 200-300 kDa MW), were purchased from FMC BioPolymer Co. (Philadelphia, PA). Cyano-functionalized silica was purchased from SiliCycle.

Immuno-competent male C57BL/6 mice were obtained from Jackson Lab and Sprague-Dawley rats were obtained from Charles River Laboratories. All animal procedures were approved by the Cornell Institutional Animal Care and Use Committee Example 1—Synthesis of Zwitterionic Sulfobetaine-Based and Carboxybetaine-Based Alginate Conjugates Di-tert-butyl dicarbonate (10.0 g, 45.8 mmol) and triethylamine (12.8 mL, 91.6 mmol) were added dropwise over 0.5 hours to a solution of N,N-dimethylethylenediamine (4.04 g, 45.8 mmol) in ethyl alcohol (150 mL) at 0° C. The mixture was stirred for 1 hour at 0° C. and then for 18 hours at room temperature. The white precipitate was filtered off and the filtrate was evaporated to obtain residue. The residue was dissolved in dichloromethane (150 mL), and the solution was washed successively with water. The organic layer was dried over anhydrous magnesium sulfate and evaporated to get N,N-dimethyl-2-((pivaloyloxy)amino)ethan-1-amine.

Example 2—Synthesis of Sulfobetaine-NH₂ Material

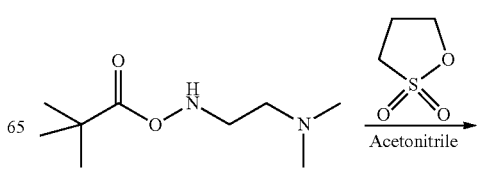

-continued

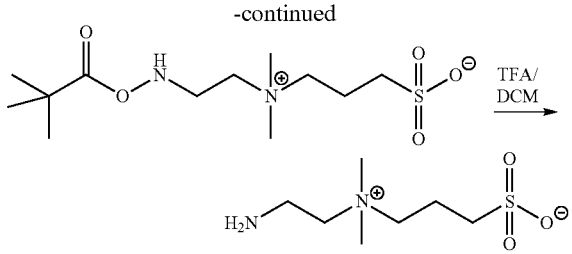

N,N-dimethyl-2-((pivaloyloxy)amino)ethan-1-amine (40.0 mmol), 1,3-propanesultone (4.9 g, 40.0 mmol), and acetonitrile (150 mL) were added into a 250 mL round-bottom flask. The mixture was stirred under nitrogen atmosphere for 48 hours at 40° C. After reaction, the solvent was removed by rotary evaporator. The product was precipitated by anhydrous diethyl ether and washed with anhydrous diethyl ether to get white powder. Finally, 10.0 g of the obtained product was treated with a mixture of 20 mL trifluoroacetic acid (TFA) and 20 mL dichloromethane overnight at room temperature, concentrated with rotary evaporator, precipitated in anhydrous diethyl ether to get white power (sulfobetaine-$NH_2$ material). $^1$H NMR ($D_2O$, 400 MHz): δ 3.70 (t, 2H), 3.54 (m, 4H), 3.20 (s, 6H), 2.97 (t, 2H), 2.24 (m, 2H).

Example 3—Synthesis of Carboxybetaine-$NH_2$ Material

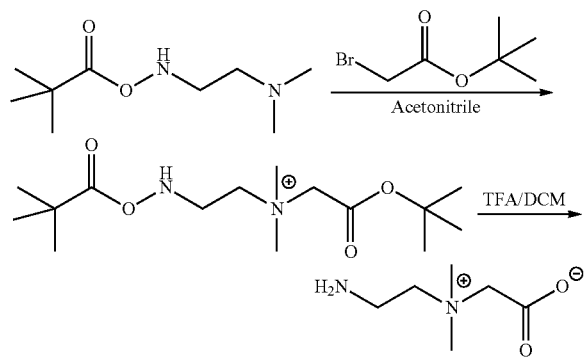

N,N-Dimethyl-2-((pivaloyloxy)amino)ethan-1-amine (40.0 mmol), tert-butyl bromoacetate (40.0 mmol), and acetonitrile (150 mL) were added into a 250 mL round-bottom flask. The mixture was stirred under nitrogen atmosphere for 48 hours at 40° C. After reaction, the solvent was removed by rotary evaporator. The product was precipitated by anhydrous diethyl ether and washed with anhydrous diethyl ether to get white powder. Finally, 10.0 g of the obtained product was treated with a mixture of 40 mL trifluoroacetic acid (TFA) and 40 mL dichloromethane overnight at room temperature, concentrated with rotary evaporator, precipitated in anhydrous diethyl ether to get white power (carboxybetaine-$NH_2$ material). $^1$H NMR ($D_2O$, 400 MHz): δ 4.31 (s, 2H), 3.99 (m, 2H), 3.55 (m, 2H), 3.36 (s, 6H).

Example 4—Sulfobetaine-Based and Carboxybetaine-Based Alginate Conjugation

VLVG alginate (0.5 g) was dissolved in the 40 ml of mixture solvent (30 ml of DI water and 10 ml acetonitrile). 2-Chloro-4,6-dimethoxy-1,3,5-triazine (CDMT) (225 mg) and N-methylmorpholine (NMM) (280 μl) were added. Then 0.84 g of sulfobetaine-$NH_2$ material was dissolved in 10 ml DI water and added into the mixture. The reaction was stirred overnight at 55° C. The solvent was removed under reduced pressure and the solid product was redissolved in DI water. The solution was filtered through a pad of cyano-functionalized silica. It was then dialyzed against a 10,000 MWCO membrane in DI water for three days. Finally, the water was removed under reduced pressure to obtain sulfobetaine-modified alginate. The carboxybetaine-modified alginate was synthesized using the similar procedure as that of sulfobetaine-modified alginate.

Example 5—Preparation of the Zwitterionic Sulfobetaine-Based Alginate Microcapsules To prepare alginate solution, 2% (w/v) alginate (VLVG, SLG20, or SLG100) was dissolved in 0.8% (w/v) NaCl solution. 2% (w/v) sulfobetaine-based alginate conjugate was dissolved in 0.8% (w/v) NaCl solution. The mixture of 80% (by volume) sulfobetaine-based alginate conjugate and 20% (by volume) SLG100 were blended to obtain the sulfobetaine-alginate (or SA) solution.

All the buffers were sterilized before use and alginate solutions were sterilized by filtration through a 0.2 μm filter. Alginate hydrogel microcapsules were prepared via the method of electrospraying. Briefly, a high voltage power generator was connected to a blunt-tipped needle. This needle was attached to a 3 ml syringe which was clipped to a syringe pump that was oriented vertically. The syringe pump pumped alginate solution out into a sterile, grounded dish containing a 20 mM barium chloride solution. After the alginate microcapsules were formed, they were collected and then washed with prepared buffer (NaCl 15.43 g, KCl 0.70 g, $MgCl_2 \cdot 6H_2O$ 0.49 g, 50 ml of HEPES (1 M) buffer solution in 2 L of DI water) 3 times. The alginate capsules were left overnight at 4° C. The capsules were finally washed 2 times in 0.8% saline and kept at 4° C. before use.

Example 6—Implantation of the Alginate Microcapsules

The mice were anesthetized using 3% isoflurane in oxygen and maintained at the same rate throughout the procedure. The abdomens of the mice were shaved and alternately scrubbed with betadine and isopropyl alcohol to create a sterile field before being transferred to the surgical field. A ~0.5 mm incision was made along the midline of the abdomen and the peritoneum was exposed using blunt dissection. The peritoneum was then grasped with forceps and a 0.5-1 mm incision was made along the linea alba. A volume of ~300 μl of microcapsules was then loaded into a sterile pipette and implanted into the peritoneal cavity through the incision.

The phase contrast images of the microcapsules were taken using an EVOS AMF4300 imaging system.

Results and Discussion of the Examples 1-6

Figure 1B:
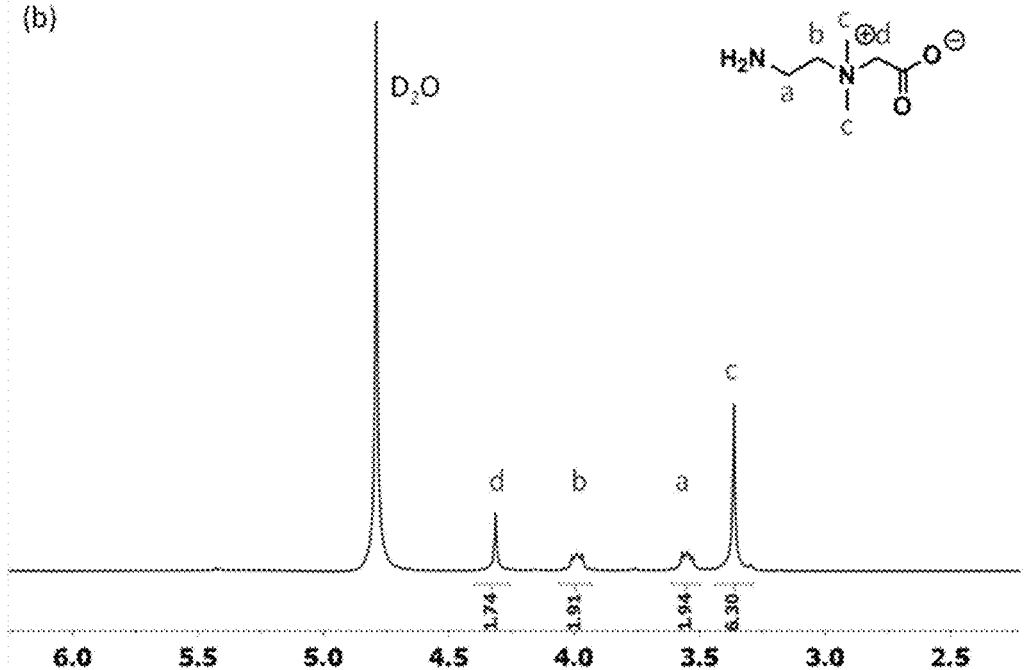

Among zwitterionic groups, sulfobetaine and carboxybetaine were chosen as examples. These zwitterionic materials have previously been shown to exhibit excellent antifouling properties (Zhang et al., "Superlow Fouling Sulfobetaine and Carboxybetaine Polymers on Glass Slides," Langmuir 22(24):10072-10077 (2006), which is hereby incorporated by reference in its entirety). The sulfobetaine-$NH_2$ and carboxybetaine-$NH_2$ monomers were synthesized according to Scheme 6. The structures of the monomers were confirmed by nuclear magnetic resonance (NMR), and the chemical shifts of the corresponding protons were marked in FIGS. 1A-B.

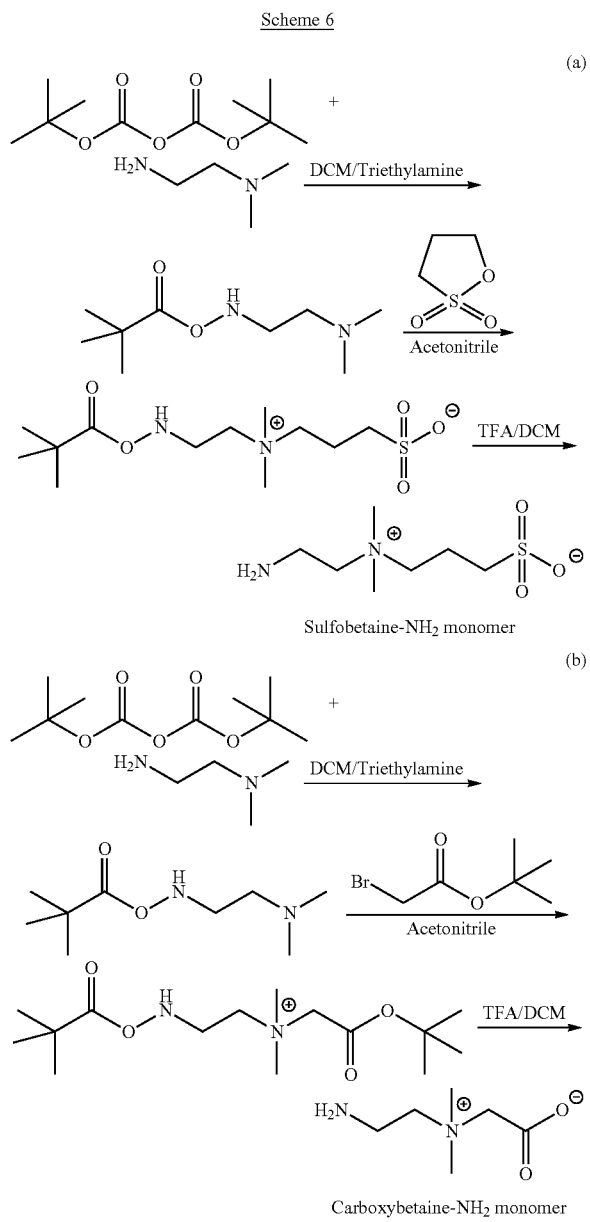

Scheme 6

Sulfobetaine-NH₂ monomer

Carboxybetaine-NH₂ monomer

The sulfobetaine-NH$_2$ and carboxybetaine-NH$_2$ monomers were prepared using N,N-dimethylethylenediamine and either (a) propanesultone or (b) tert-butyl bromoacetate.

Figure 2A:
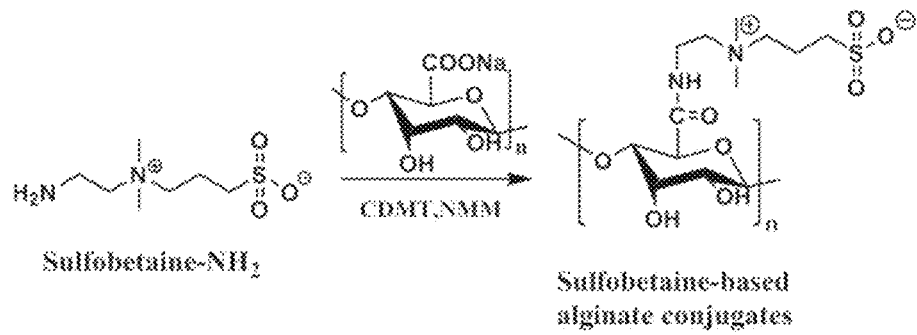
FIGS. 2A-2B show synthesis and characterization of the sulfobetaine-based alginate conjugates as described herein.
Figure 2B:
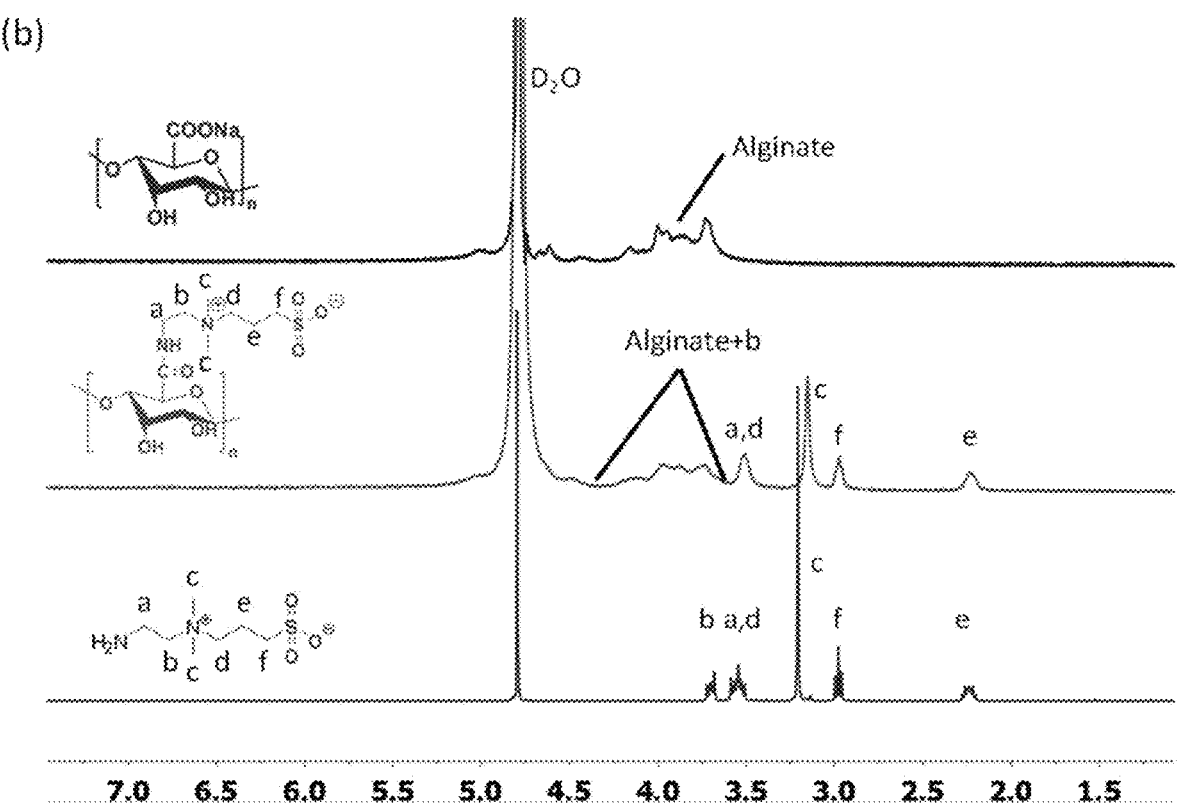
Figures 3A, 3B:
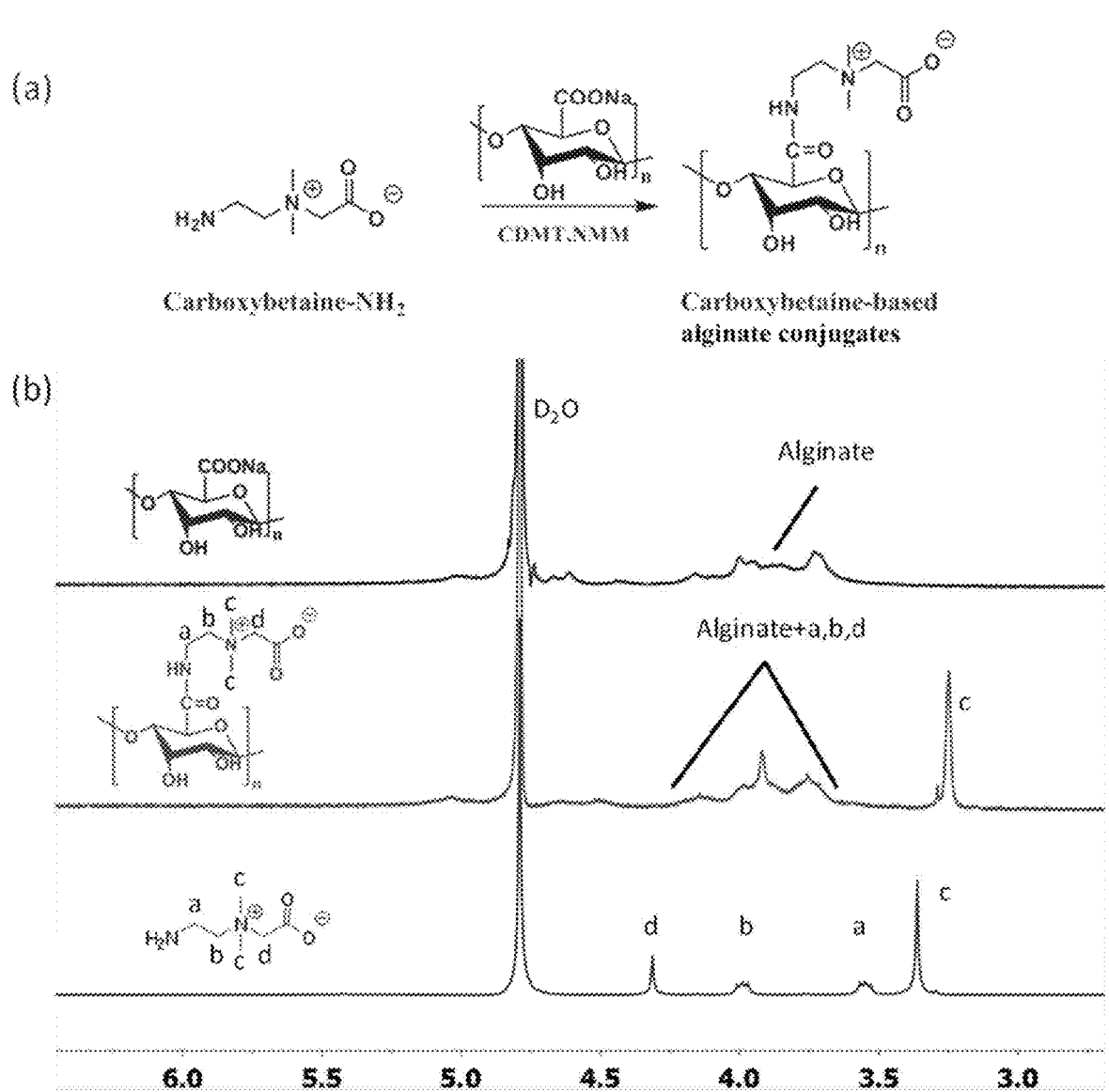
FIGS. 3A-3B show synthesis and characterization of the carboxybetaine-based alginate conjugates as described herein.

To modify the alginate, low molecular weight (MW), VLVG alginate was used as the starting material. 2-Chloro-4,6-dimethoxy-1,3,5-triazine (CDMT) and N-methylmorpholine (NMM) were used as coupling reagents to conjugate alginate with sulfobetaine-NH$_2$ via a triazine-based coupling reaction as shown in FIG. 2A. The sulfobetaine-based alginate conjugate was characterized by $^1$H NMR spectrum (FIG. 2B). The characteristic peak of sulfobetaine-NH$_2$ segment is as follows: the peak at 3.20 ppm is attributed to six protons in two methyl groups attached to the quaternary amine in the sulfobetaine pendant group. The result suggests that sulfobetaine-NH$_2$ was successfully conjugated to alginate. About 30.5% modification of the starting alginate was confirmed by NMR data analysis. Carboxybetaine-based alginate was prepared as shown in FIG. 3A. For the carboxybetaine-based alginate, characteristic peak of 3.25 ppm in FIG. 3B was attributed to six protons in two methyl groups attached to the quaternary amine in the carboxybetaine pendant group, and the modification degree is about 35.6%.

Since hydrogel microcapsules have been used extensively for cell encapsulation, culture, and transplantation, the microcapsules of sulfobetaine-based alginate conjugate were fabricated by electrospraying using barium chloride as cross-linker, although other polyvalent ions such as $Ca^{2+}$, $Sr^{2+}$ could be used, which were previously demonstrated to have long-term in vivo stability. The foreign body response to the SA microcapsules was evaluated in the intraperitoneal space of C57BL/6J mice 14 days post implantation, with SLG20 alginate as control.

Figure 4:
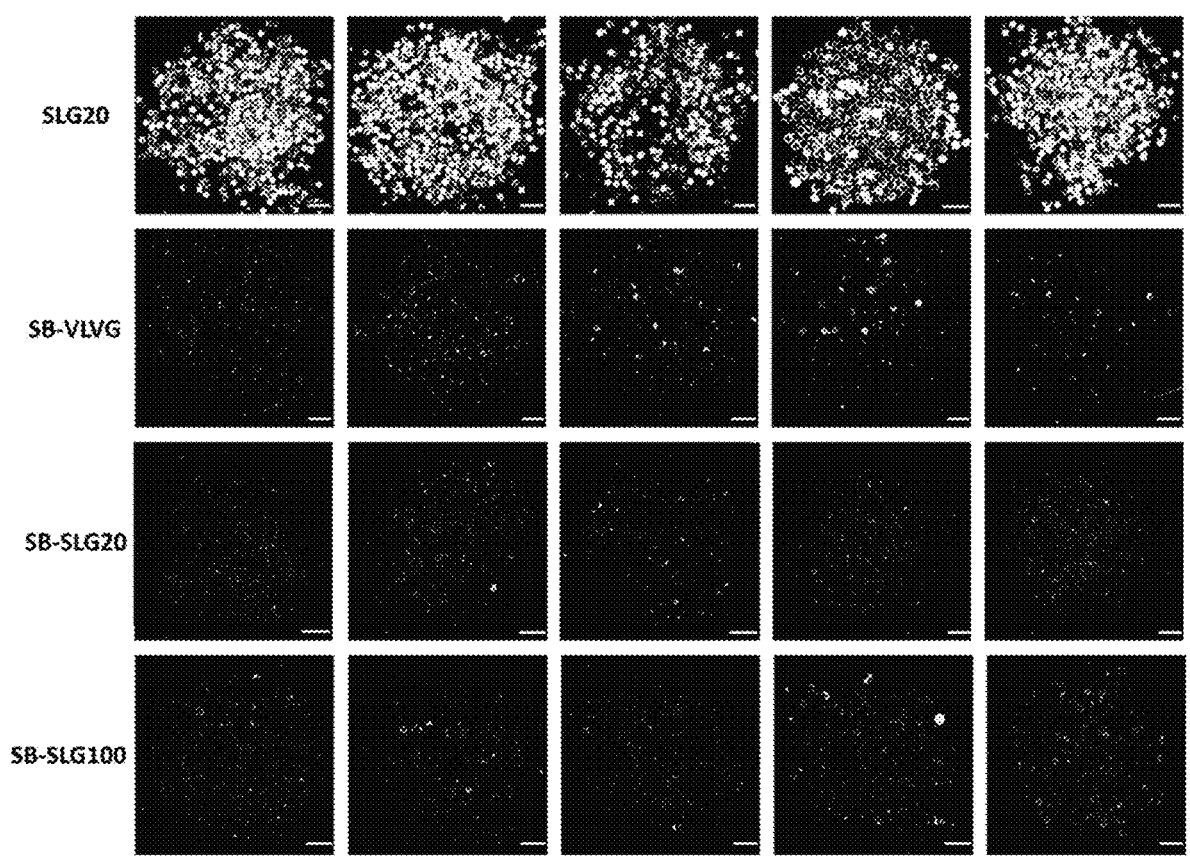
FIG. 4 are images showing three kinds of sulfobetaine-modified alginate microcapsules (SB-VLG, SB-SLG20, and SB-SLG100) with almost no fibrosis after 14 days of intraperitoneal implantation in C57BL/6J mice. Dark-field phase contrast images of the microcapsules retrieved after 2 weeks in the intraperitoneal space show much less fibrosis on SB-alginate microcapsules than on SLG20 unmodified control microcapsule. SLG20, VLVG, SLG100 are alginates with different molecular weights. Scale bars, 2000 μm; n=5; each image represents one mouse.

The whiteness on the microcapsule surfaces (FIG. 4, top row of images) indicated the fibrotic deposition, and therefore the control microcapsule (SLG 20) induced substantial fibrosis. In contrast, there was almost no fibrotic deposition on the sulfobetaine modified VLVG (SB-VLVG) microcapsules (FIG. 4, second row of images from top). Moreover, sulfobetaine modified SLG 20 (SB-SLG20) and sulfobetaine modified SLG 100 (SB-SLG 100) microcapsules also exhibited almost no fibrosis (FIG. 4, third and fourth rows of images from the top, respectively). These results suggested that the SB modified alginate microcapsules, regardless of alginate types, mitigated the foreign body response effectively and reproducibly.

Figure 5:
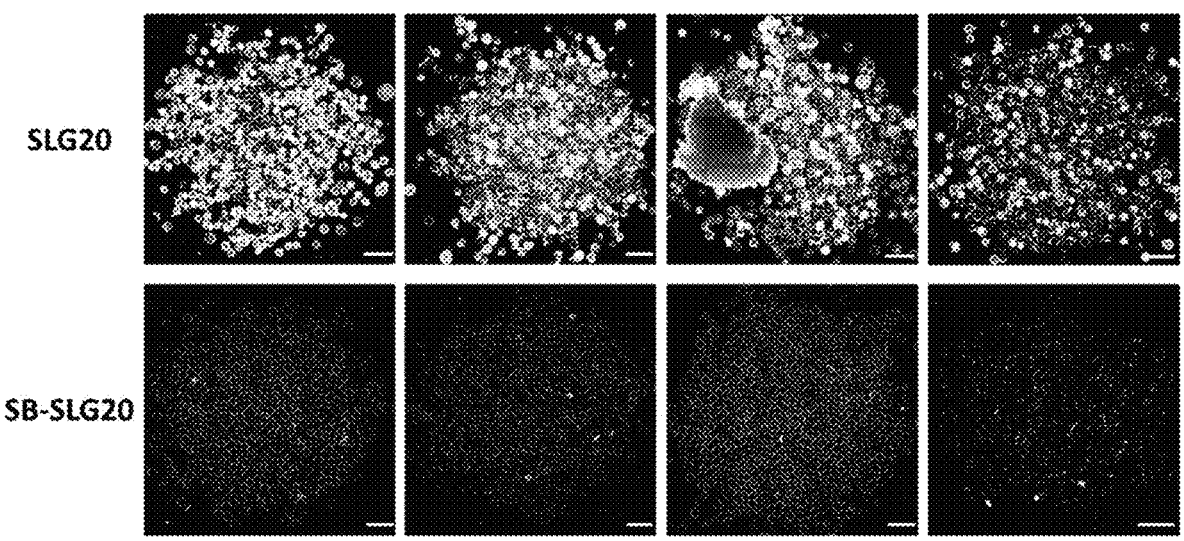
FIG. 5 shows sulfobetaine (SB) modified alginate (SB-SLG 20) microcapsules with almost no fibrosis after 100 days of intraperitoneal implantation in C57BL/6J mice. Dark-field phase contrast images of the microcapsules retrieved after 100 days in the intraperitoneal space show much less fibrosis on SB modified microcapsules (bottom row of images) than on SLG20 control microcapsules (top row of images). Scale bars, 2000 μm; each image represents one mouse, n=4.

To investigate the effect of SB modified alginate on the foreign body reactions in the long-term, SB-SLG 20 microcapsules were implanted into the intraperitoneal space of immunocompetent C57BL/6J mice and harvested after 100 days. Dark field phase contrast microscopy of retrieved SLG 20 microcapsules showed extensive fibrotic deposition (FIG. 5, top row of images), whereas SB-SLG20 microspheres showed much lower level of fibrotic deposition (FIG. 5, bottom row of images). Moreover, some of retrieved SLG 20 microcapsule even aggregated together, a sign of severe fibrosis (FIG. 5, top row, third image from left).

Figure 6:
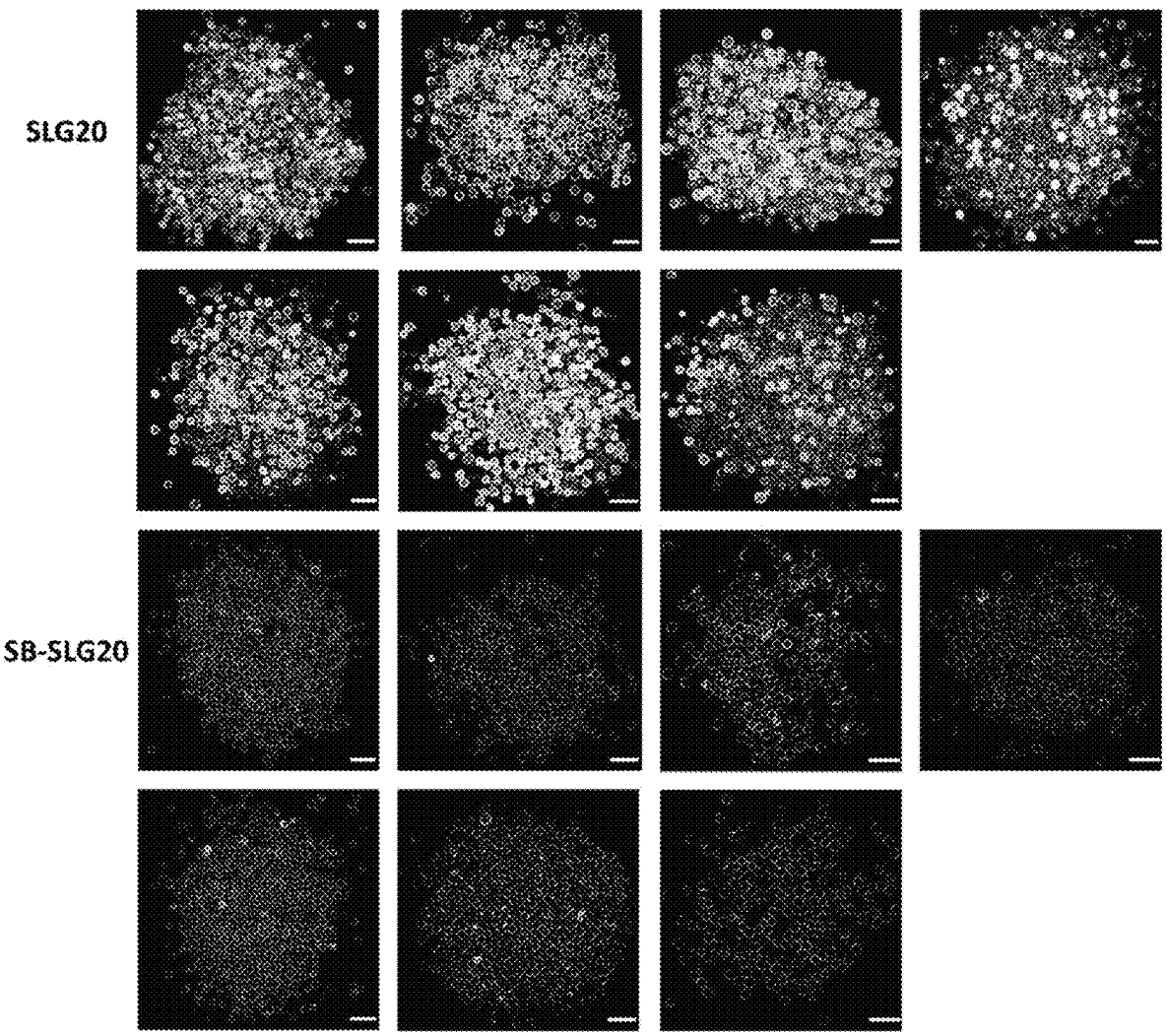
FIG. 6 shows SB-SLG 20 microcapsules with almost no fibrosis after 180 days of intraperitoneal implantation in C57BL/6J mice. Dark-field phase contrast images of the microcapsules retrieved after 180 days in the intraperitoneal space show much less fibrosis on SB modified microcapsules than on SLG20 control microcapsule. Scale bars, 2000 μm; each image represents one mouse, n=7.
Figure 7:
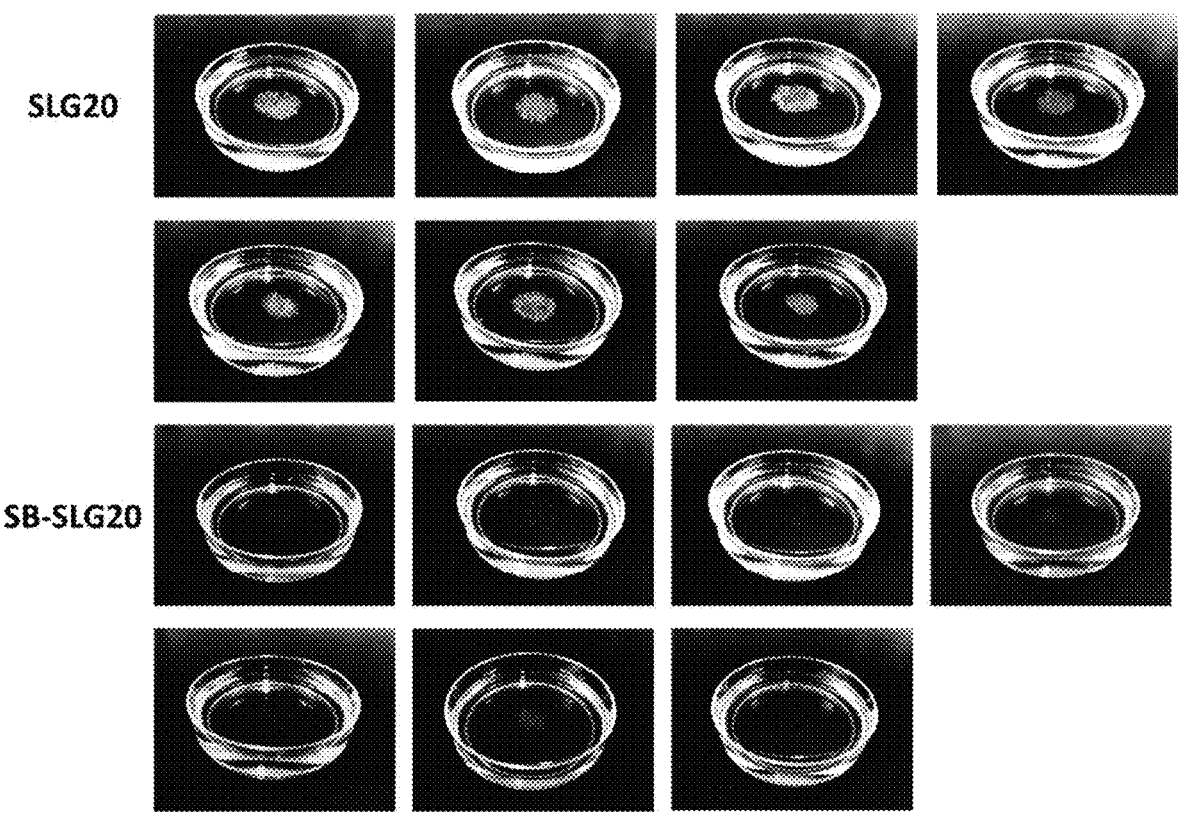
FIG. 7 shows images of the retrieved SB-SLG 20 (bottom two rows) and SLG 20 (top two rows) microcapsules after 180 days of intraperitoneal implantation in C57BL/J6 mice. n=7. The whiteness of the capsules indicates fibrosis.

To further evaluate performance of SB modified alginate, SB-SLG20 microcapsules were examined after 180 days implantation in C57BL/6J. As shown in FIG. 6, SB-SLG 20 microcapsules after retrieval were largely clean of fibrotic deposition (FIG. 6, top two rows of images) while there was substantial fibrosis observed on the conventional SLG 20 microcapsules surfaces (FIG. 6, bottom two rows of images). FIG. 7 shows numerous retrieved microcapsules in each dish. The whiteness on the microcapsule surfaces indicated the fibrotic deposition. Clearly, the whiteness mostly shown on the SLG 20 microcapsules indicated severe fibrosis (FIG. 7, top two rows); the absence of this whiteness for the SB-SLG 20 microcapsules indicated almost no fibrosis (FIG. 7, bottom two rows). This result suggested that SB modified alginate substantially reduced foreign body reactions in the intraperitoneal space of C57BL/6 mice for a significantly longer period of 180 days.

Figure 8:
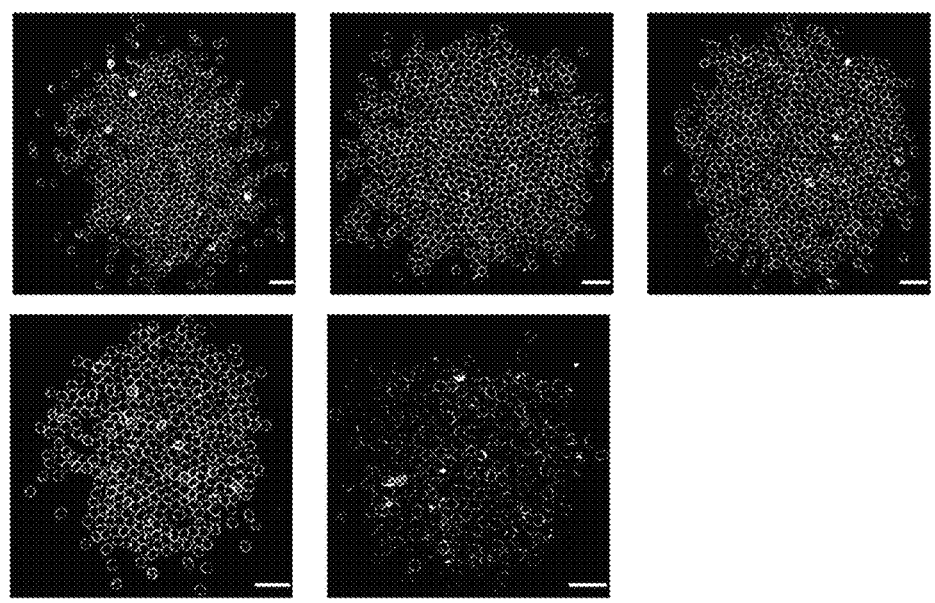
FIG. 8 shows dark-field phase contrast images of ethylene-glycol SB microcapsules with almost no fibrosis after 30 days of intraperitoneal implantation in C57BL/6J mice. Scale bars, 2000 μm; n=5.

Another type of sulfobetaine modified alginate: ethylene-glycol SB alginate was also designed and developed. The foreign body response to the ethylene-glycol SB-SLG20 microcapsules was evaluated in the intraperitoneal space of C57BL/6J mice 30 days post implantation. After retrieval, ethylene-glycol SB-SLG20 microcapsules (FIG. 8) were clean, and showed almost no fibrosis.

Taken together, zwitterionic modified alginates were capable of mitigating the foreign body response effectively and reproducibly. This may be attributed to the zwitterionic sulfobetaine group that reduces biofouling and improves the biocompatibility of alginate. This zwitterionic sulfobetaine-based alginate conjugate will be applicable to islet encapsulation to support long-term diabetes correction for type-1 diabetes (TD1).

Figure 9A:
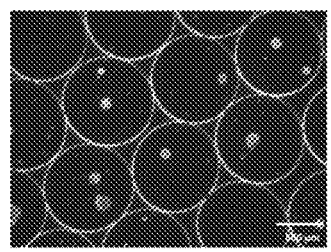
FIGS. 9A-9G show that rat islets encapsulated in SB-SLG 20 capsules maintained long-term normoglycemia in STZ-treated diabetic C57BL/6J mice as compared to the SLG20 control group.
Figure 9B:
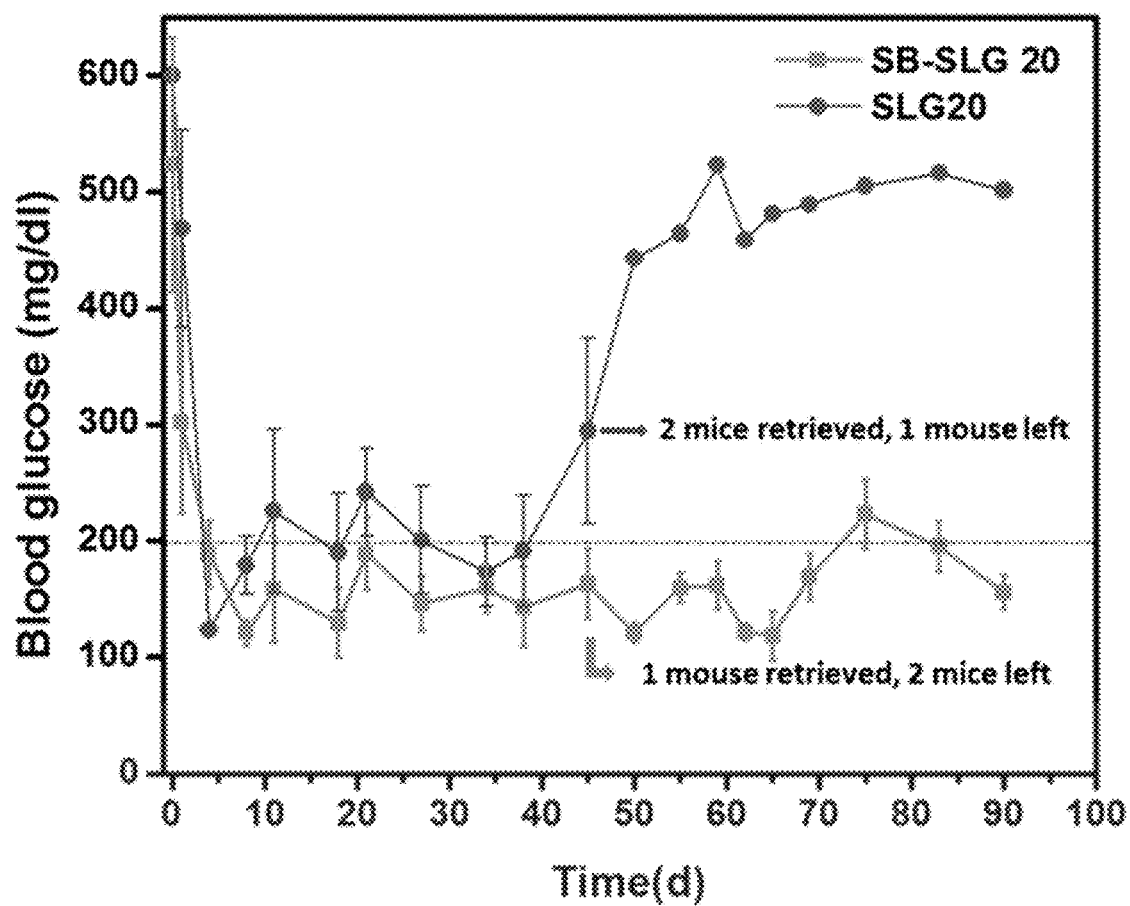

After confirming that zwitterionically modified alginates such as SB-SLG20 resists fibrosis in C57BL/6J mice, its therapeutic potential as a cell encapsulation medium for the treatment of diabetes was explored. Encapsulated rat islets were transplanted into the peritoneal cavity of streptozotocin (STZ)-induced C57BL/6 diabetic mice and evaluated for 90 days for their ability to restore normoglycemia. Rat islets were encapsulated with 1000 µm SB-SLG20 microcapsules as barrier to shield foreign body response, or with SLG 20 microcapsules as control (FIG. 9A). The blood glucose (BG) level of the mice decreased to the normal glycemic range (BG<200 mg/dL) a few days after the transplantation (FIG. 9B). However, mice transplanted with rat islets encapsulated in SLG 20 microcapsules showed a shorter duration of glycemic control and were unable to sustain normoglycemia beyond 45 days, while the mice transplanted with rat islets encapsulated in SB-SLG 20 microcapsules remained cured for 3 months before the microcapsules were retrieved.

Figures 9C, 9D, 9E, 9F, 9G:
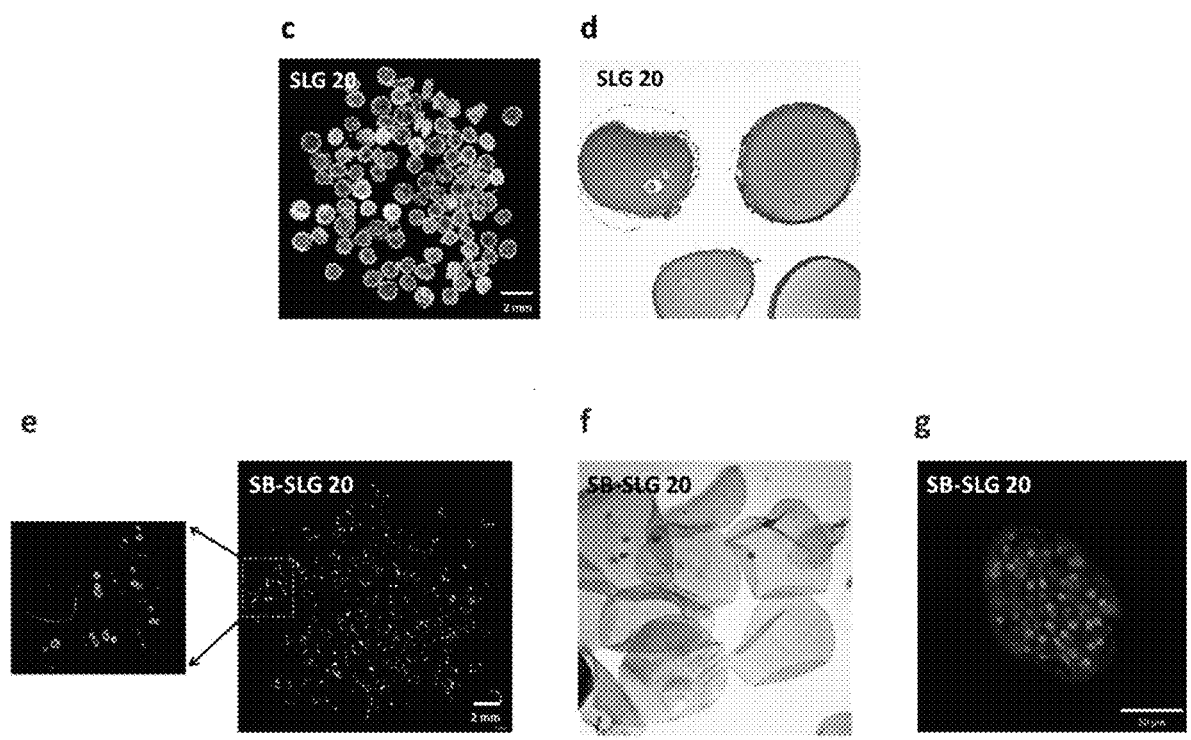

The whiteness was mostly shown on the retrieved SLG 20 microcapsules (FIG. 9C), suggesting severe fibrosis. It was also confirmed using H&E stained histological analysis (FIG. 9D). The result of H&E staining of tissue sections showed that SLG 20 produced microcapsules with high fibrotic deposition around the implant. On the contrary, retrieved SB-SLG 20 microcapsules encapsulating rat islets (FIG. 9E-F) showed almost no fibrous deposition. There were also numerous rat islets observed in the microcapsules after retrieval. Importantly, these islets were still functional after 3 months implantation, as indicated by the positive insulin staining (FIG. 9G) on the islets in retrieved SB-SLG 20 microcapsules. Taken together, encapsulated rat islets were able to achieve long-term glycemic correction (90 days) in STZ-treated C57BL/6J mice for T1D, using the zwitterionically modified alginate capable of mitigating the FBR effectively.

Super-biocompatible, zwitterionically modified alginates were designed and synthesized. Sulfobetaine-NH2, ethylene glycol sulfobetaine-NH2, and carboxybetaine-NH2 were successfully synthesized and subsequently conjugated to alginate. The sulfobetaine-modified alginate were tested in C57BL/6 mice and mitigated the foreign body response effectively compared to the unmodified control alginate. The therapeutic potential of the SB modified alginate was demonstrated through a type 1 diabetic mouse model using rat islets. SB-SLG 20 encapsulated islet cells were proven to be capable of providing long-term glycemic correction in immune-competent diabetic C57BL/6J mice. It was determined that this zwitterionically modified alginate may contribute to the translation of cell encapsulation for T1D and potentially other diseases.

Materials for Examples 7-16

Propargylamine, acryloyl chloride, sodium azide, sodium ascorbate, copper sulfate pentahydrate, iodomethane, trifluoroacetic acid (TFA), 2-chloro-N,N-dimethylethylamine hydrochloride, 1,3-propanesultone, 2-hydroxyethyl methacrylate (HEMA), 2-hydroxy-2-methylpropiophenone, phosphate buffered saline (PBS), dichloromethane (DCM), dimethyl sulfoxide (DMSO), acetonitrile, hexane, ethyl acetate, diethyl ether, and ethyl alcohol were purchased from Sigma-Aldrich. Tert-butyl bromoacetate and ion exchange resin (Amberlyst A-26, OH form) were obtained from Alfa Aesar. Procedures for the synthesis of qTR-CB, TR-CB, and TR-SB monomers are described below. Carboxybetaine methacrylate (CB) (Yang et al., "Pursuing "Zero" Protein Adsorption of Poly(carboxybetaine) from Undiluted Blood Serum and Plasma," *Langmuir* 25(19):11911-11916 (2009), which is hereby incorporated by reference in its entirety) and carboxybetaine diacrylamide (CBAAX) (Zhang et al., "Zwitterionic gel Encapsulation Promotes Protein Stability, Enhances Pharmacokinetics, and Reduces Immunogenicity," *Proceedings of the National Academy of Sciences* 112(39):12046-12051 (2015), which is hereby incorporated by reference in its entirety) were synthesized using methods reported previously.

Example 7—Hydrogel Preparation

The TR-ZW hydrogels were prepared via radical polymerization initiated by UV irradiation. The hydrogel solution consisted of 1 mL DI water, 600 mg monomer, 4% CBAAX cross linker (molar percent of monomer), and 3.5 mg 2-hydroxy-2-methylpropiophenone photo-initiator. The resulting solution was cast between a pair of glass slides, separated with a 2-mm-thickness poly(tetrafluoroethylene) (PTFE) spacer, and polymerized under UV (365 nm) for 45 min. PHEMA and PCB hydrogels were prepared using a similar procedure. After preparation, all hydrogel samples were equilibrated in sterile PBS buffer and the PBS buffer solution was changed at least three times a day for five days. For implantation, the hydrogels were punched into disks with a diameter of 6 mm, and stored in sterile PBS at 4° C. before use.

Example 8—Protein Adsorption Assay

P(qTR-CB) polymer brushes were grafted onto gold-coated surface plasmonic resonance (SPR) sensor chips following the procedure reported previously (Zhang et al., "Zwitterionic Hydrogels: an in vivo Implantation Study," *Journal of Biomaterials Science, Polymer Edition* 20(13): 1845-1859 (2009), which is hereby incorporated by reference in its entirety). The protein adsorption on the P(qTR-CB)-grafted gold surfaces was evaluated using a four-channel SPR sensor. Firstly, PBS buffer was flowed into the channels for 10 min to build the baseline. Secondly, a 1 mg/mL fibrinogen solution or 100% human blood plasma was run through the channels for 10 min followed by a PBS buffer wash to remove unbound protein molecules. The amount of adsorbed protein was finally quantified by the change of wavelength shift between the pre-adsorptive and post-adsorptive baselines. A 1 nm SPR wavelength shift at 750 nm corresponded to a protein surface coverage of 15 ng/cm$^2$ (Liu et al., "Amino Acid-Based Zwitterionic Poly (Serine Methacrylate) as an Antifouling Material," *Biomacromolecules* 14(1):226-231 (2012), which is hereby incorporated by reference in its entirety). The protein adsorption on the P(TR-CB) and P(TR-SB) surfaces was evaluated using the same procedure.

Example 9—Cell Attachment Assay

NIH/3T3 cells were cultured in a humidified incubator with 5% $CO_2$ at 37° C. The culture medium was composed of Dulbecco's modified Eagle medium (DMEM), 10% fetal bovine serum (FBS), and 2% penicillin streptomycin. The hydrogel disks with a diameter of 6 mm were individually placed into a 12-well plate and washed with sterile PBS buffer three times. Cell suspension (2 mL) (concentration: 105 cells/mL) was then transferred into each well and incubated with these hydrogels for 3 days at 37° C. After incubation, the hydrogels were transferred to a new 12-well plate containing sterile PBS in each well. The LIVE/DEAD assay solution was added into each well and incubated for 30 min. These hydrogels were finally imaged by using an EVOS AMF4300 imaging system.

Example 10—Tensile and Compression Tests

Tensile tests of hydrogel samples were performed on a TA instrument DMA Q800 Dynamic Mechanical Thermal Analysis (DMTA). All equilibrated hydrogel samples were cut in rectangular shape with 25 mm length, 6 mm width, and 2-3 mm thickness. Hydrogel samples were stretched until failure at a rate of 5 mm min$^{-1}$. The compression tests and loading-unloading tests of hydrogel samples were done on Instron 5965 with a 100 N load cell. For compression tests, each hydrogel disk with a diameter of 6 mm (about 2-3 mm thickness when equilibrated in PBS buffer) was compressed until failure at a rate of 1 mm min$^{-1}$. The shape recovery property of the hydrogels was evaluated by ten consecutive loading and unloading cycles at a constant rate of 1 mm min$^{-1}$ in the strain range of 0-65%. All samples were measured at the room temperature.

Example 11—Cytokine Secretion

Bone marrow derived macrophages (BMDMs) were seeded on the tissue culture plates or various hydrogel surfaces at a cell density of $10^6$ cells/cm$^2$ and stimulated with different combinations: 0.3 ng/mL lipopolysaccharide (LPS) (Sigma-Aldrich), 1.0 ng/mL IFNγ (R&D systems, Minneapolis, MN), 20 ng/mL IL-4 (Invitrogen), and 20 ng/mL IL-13 (Invitrogen). After stimulation for 36 hours, supernatants were collected and analyzed for TNF-α and IL-10 secretion by ELISA (enzyme-linked immunosorbent assay) following the manufacturer's instructions (BioLegend, San Diego, CA).

Example 12—Hydrogel Implantation and Histological Analysis

All animal protocols were approved by the Cornell Institutional Animal Care and Use Committee. Eight-week-old, immune-competent male C57BL/6 mice were obtained from Jackson Laboratory. The equilibrated hydrogel disks were implanted subcutaneously in mice for 1, 2, and 3 months, respectively. For each mouse, hydrogel disks made from different monomers were implanted on the back of the mouse and the sites of various hydrogel samples were alternated in order to eliminate the effect of implantation positions. At the end of each experiment, mice were euthanized by $CO_2$ asphyxiation. The hydrogel disks together with surrounding tissues were dissected and fixed in 10% neutrally buffered formalin. After embedded in paraffin wax, the samples were sectioned and stained with Masson's trichrome by Cornell Histology Core Facility. The stained histology slides were scanned using an Aperio CS2 ScanScope (Leica Biosystems, Nusslock GmbH). The blue-pixel density was measured using an Image J software. The collagen density was quantified as a percentage of average maximum blue-pixel density as determined from all analyzed sections. For each sample, three random fields were analyzed for each fixed distance (e.g. 0 to 10 μm; 10 to 20 μm; etc.) within 60 μm from the tissue-hydrogel interface. The sample size was n=5.

In order to assess the blood vessel formation upon the hydrogels, paraffin-embedded sections were stained using primary Goat anti-mouse CD31 (R&D Systems, dilution 1:200), which is an endothelial cell biomarker. The Alexa Fluor 488 donkey anti-Goat as secondary antibody (Life Technologies, dilution 1:500) was used in this work. Two stained sections at different positions of each hydrogel disks were used and five different fields were randomly examined in each section. The density of blood vessels were quantified by counting the number of the vascular features normalized to the capsule area. The sample size was n=5.

Example 13—Statistical Analysis

All the data are presented as the mean value±standard deviation. The difference was considered statistically significant when the p value is less than 0.05. A Student's t-test was used for all statistical analysis.

Example 14—Synthesis of qTR-CB Monomer

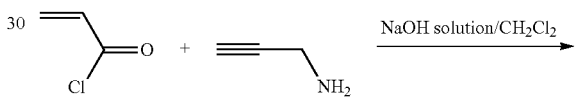

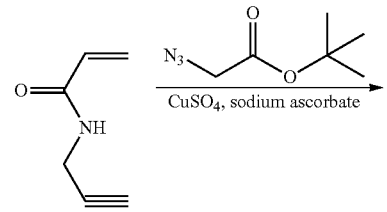

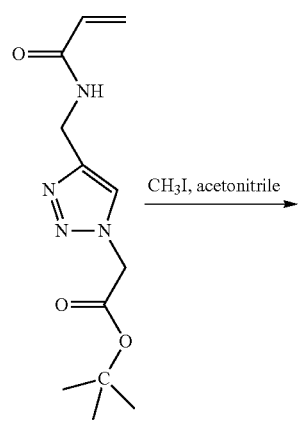

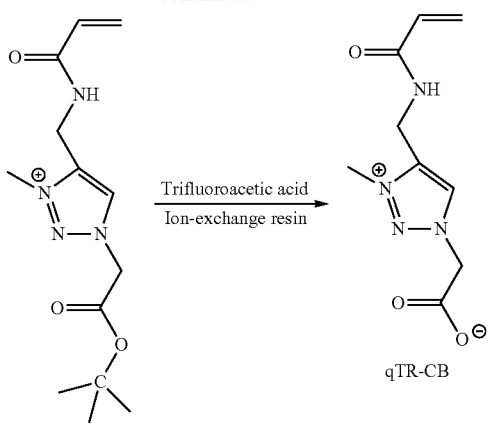

qTR-CB

N-Propargylacrylamide (10a)

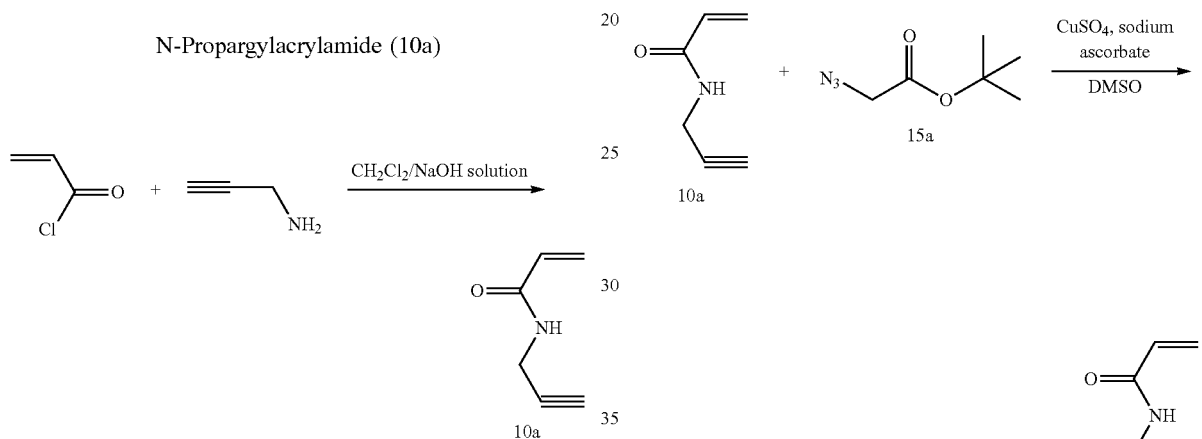

Figure 10:
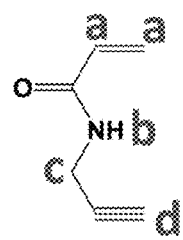
FIG. 10 shows $^1$H NMR spectrum of product 10a at 400 MHz, CDCl$_3$.
Figure 10:
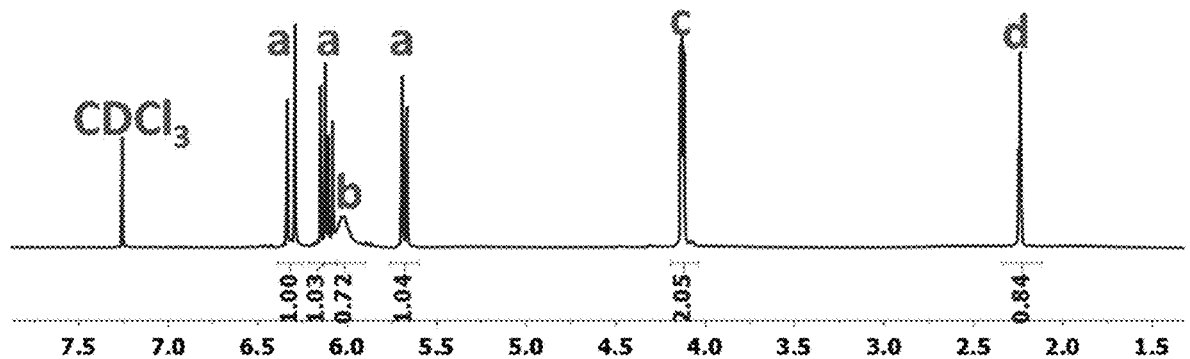

Propargylamine (3.3 g, 60 mmol) was dissolved in 150 mL DCM at 0° C. Aqueous NaOH (1.5 M, 100 mL) was then added into the solution. Acryloyl chloride (14.9 g, 165 mmol) was added dropwise into the denser dichloromethane layer over 30 minutes resulting in a yellow orange solution. The mixture was stirred for 1 hour at 0° C. and then for 18 hours at room temperature. The resulting solution was washed successively with water. The organic layer was dried over anhydrous sodium sulfate and evaporated to get yellow oil. The product N-propargylacrylamide (4.2 g, 64%) was obtained as light yellow solid by silica gel column chromatography (eluent: ethyl acetate/hexane, 1:1, v/v). $^1$H NMR (CDCl$_3$, 400 MHz): δ 6.32 (dd, 1H), 6.13 (dd, 1H), 5.68 (dd, 1H), 4.12 (m, 2H), 2.23 (m, 1H) (FIG. 10). $^{13}$C NMR (CDCl$_3$, 400 MHz): 165.4, 130.1, 127.2, 79.3, 71.6, 29.2.

Tert-butyl 2-azidoacetate (15a)

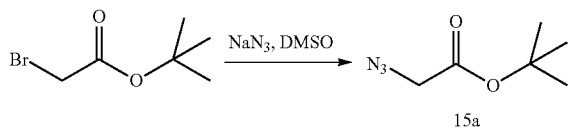

Figure 11:
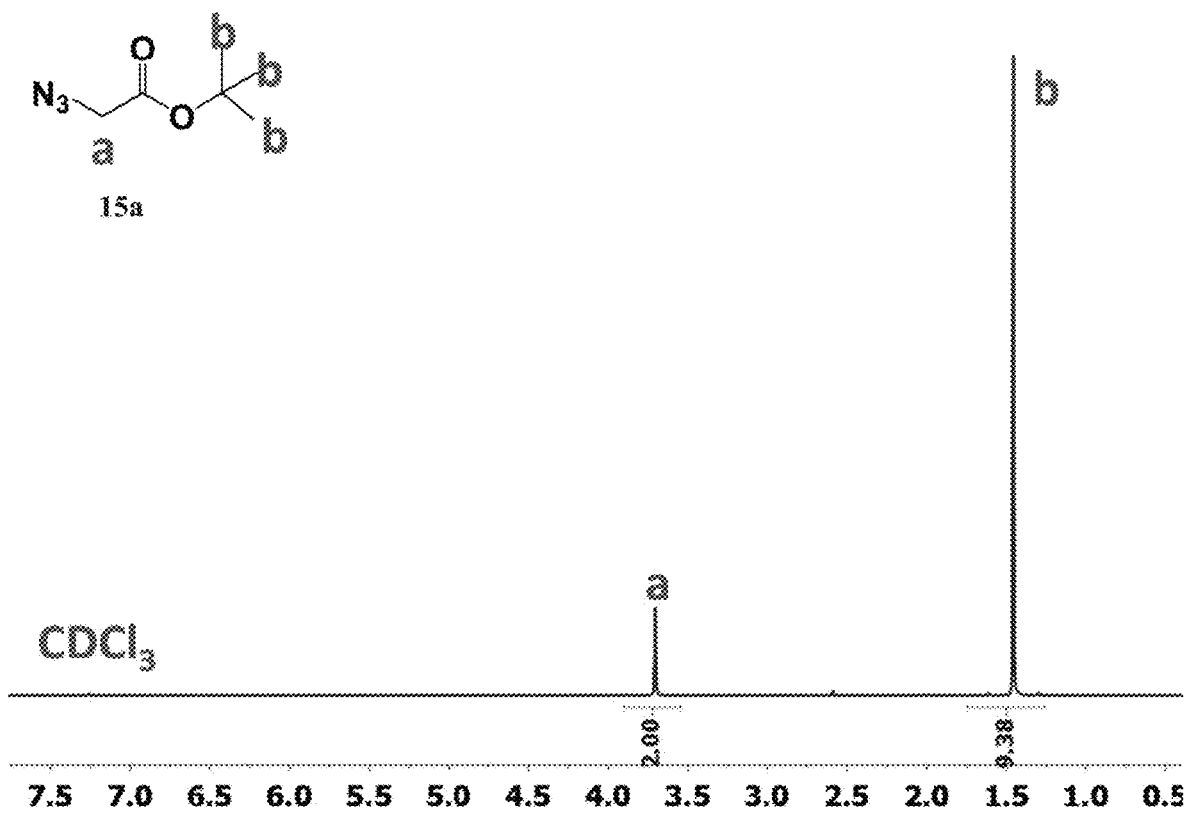
FIG. 11 shows $^1$H NMR spectrum of product 15a at 400 MHz, CDCl$_3$.

Tert-butyl bromoacetate (15.6 g, 80 mmol) was dissolved in 100 mL DMSO at room temperature. Sodium azine (NaN$_3$) (6.5 g, 100 mmol) was added slowly into the solution and stirred for overnight at 70° C. Water (150 mL) was added to quench the reaction and the water layer was extracted with 3×200 mL anhydrous diethyl ether. The combined organic phase was washed successively with brine and dried over anhydrous sodium sulfate. The organic solvent was removed under reduced pressure to obtain the product of tert-butyl 2-azidoacetate (14.2 g, 90%). $^1$H NMR (CDCl$_3$, 400 MHz): δ 3.74 (s, 2H), 1.49 (s, 9H) (FIG. 11). $^{13}$C NMR (CDCl$_3$, 400 MHz): 167.3, 82.9, 50.8, 27.9.

Tert-butyl 2-(4-(acrylamidomethyl)-1H-1,2,3-triazol-1-yl)acetate (16a)

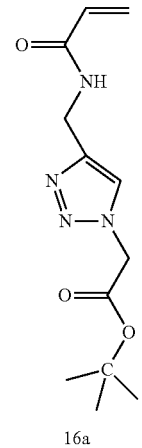

Figure 12:
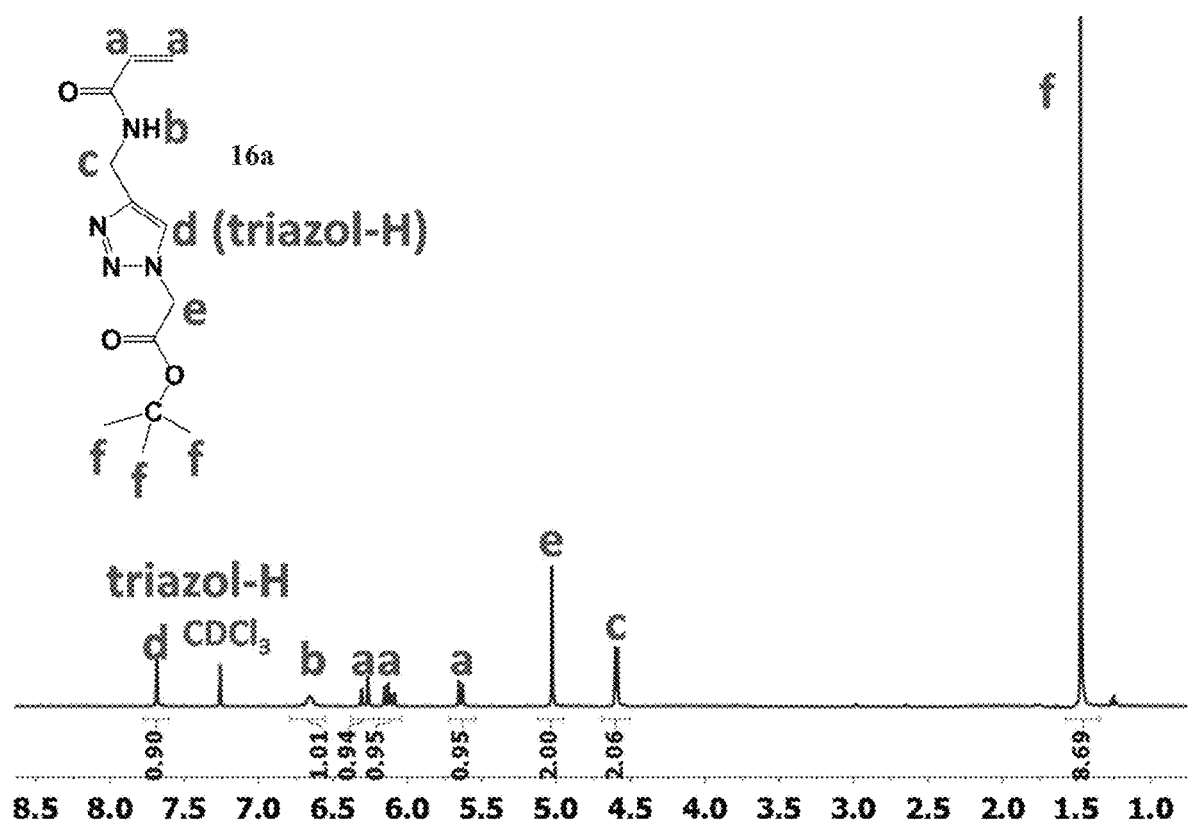
FIG. 12 shows $^1$H NMR spectrum of product 16a at 400 MHz, CDCl$_3$.

The mixture of product 10a (4.2 g, 38.4 mmol), product 15a (6.1 g, 38.4 mmol), sodium ascorbate (0.76 g, 3.8 mmol), CuSO4·5H2O (0.96 g, 3.8 mmol), and 100 mL DMSO were added into a 250 mL round-bottom flask. The mixture was stirred under nitrogen atmosphere for 48 hours at 60° C. 150 mL water was added to quench the reaction. Then the resulting solution was extracted with ethyl acetate three times. The combined organic layer was dried over anhydrous sodium sulfate and the solvent was removed under reduced pressure to get the crude product. The product 16a (8.0 g, 78%) was further purified by silica gel column chromatography (eluent: ethyl acetate). $^1$H NMR (CDCl$_3$, 400 MHz): δ 7.68 (s, 1H), 6.27 (dd, 1H), 6.13 (dd, 1H), 5.63 (dd, 1H), 5.01 (s, 2H), 4.57 (m, 2H), 1.45 (s, 9H) (FIG. 12). $^{13}$C NMR (CDCl$_3$, 400 MHz): 165.5, 165.1, 144.7, 130.4, 126.4, 123.9, 83.6, 51.3, 34.5, 27.7.

4-(Acrylamidomethyl)-1-(2-(tert-butoxy)-2-oxo-ethyl)-3-methyl-1H-1,2,3-triazol-3-ium (17a)

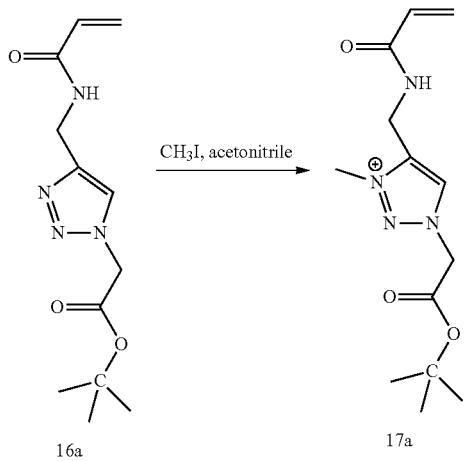 [SMILES: C=CC(=O)NCc1cn(CC(=O)OC(C)(C)C)nn1 ; C=CC(=O)NCc1cn(CC(=O)OC(C)(C)C)n[n+]1C]

Figure 13:
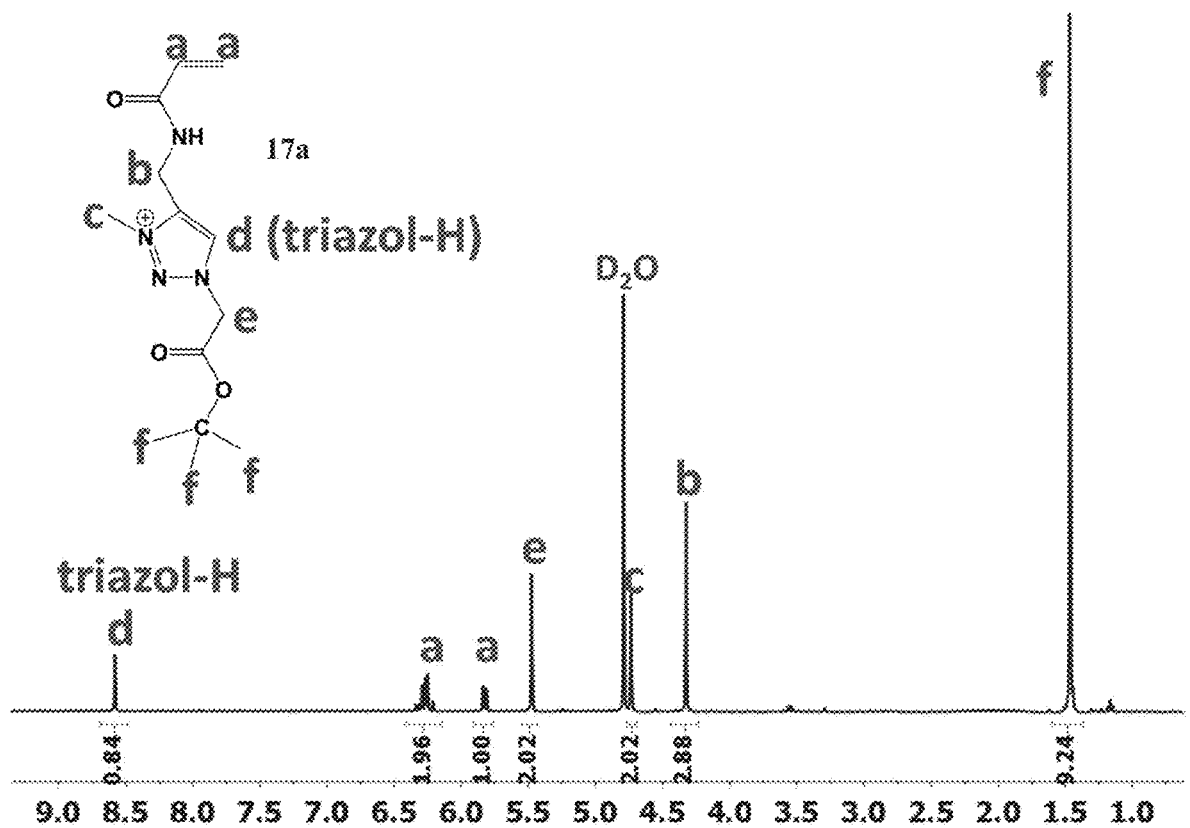
FIG. 13 shows $^1$H NMR spectrum of product 17a at 400 MHz, D$_2$O.

Product 16a (8.0 g, 30 mmol), iodomethane (25.6 g, 180 mmol), and acetonitrile (150 mL) were added into a 250 mL round-bottom flask. The mixture was stirred under nitrogen atmosphere for 48 hours at 60° C. After reaction, the solvent was removed by rotary evaporator. The resulting product was precipitated by anhydrous diethyl ether and washed with anhydrous diethyl ether to get tan powder of product 17a (7.5 g, 61%). $^1$H NMR (D$_2$O, 400 MHz): δ 8.58 (s, 1H), 6.26 (dd, 2H), 5.83 (dd, 1H), 5.48 (s, 2H), 4.74 (s, 2H), 4.34 (s, 3H), 1.47 (s, 9H) (FIG. 13). $^{13}$C NMR (D$_2$O, 400 MHz): 168.7, 164.8, 141.0, 129.0, 128.9, 128.7, 86.3, 54.2, 38.0, 32.2, 27.0.

Quaternized Triazole Carboxybetaine Acrylate (qTR-CB)

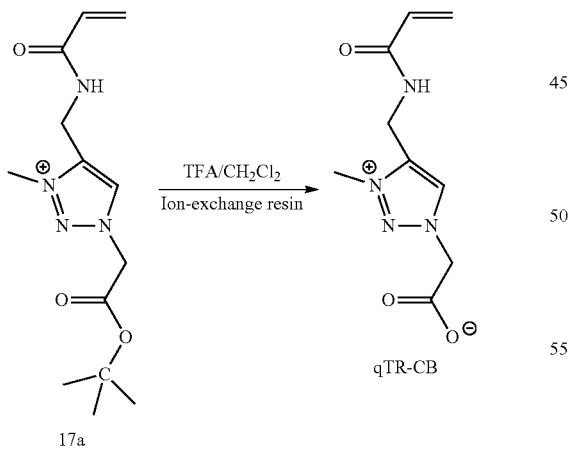

Figure 14:
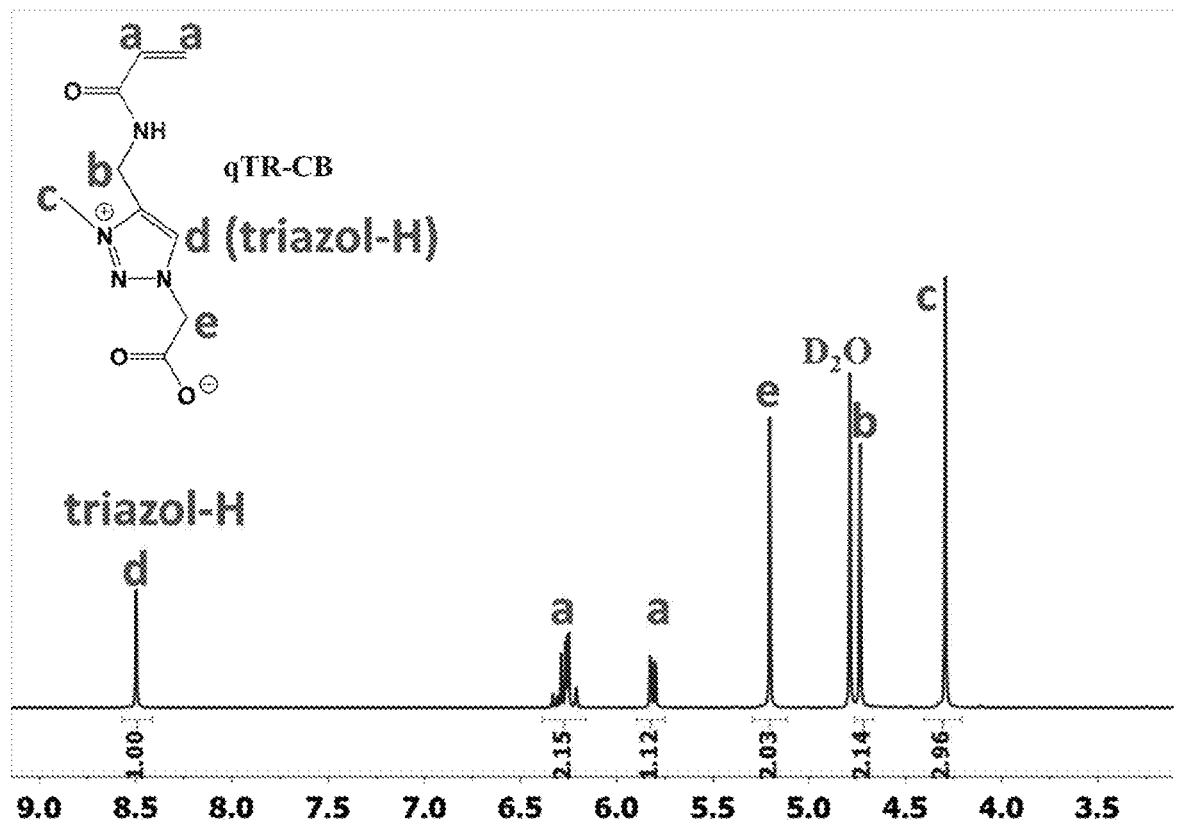
FIG. 14 shows $^1$H NMR spectrum of qTR-CB at 400 MHz, D$_2$O.

The obtained product 17a (7.5 g) was treated with a mixture of 15 mL trifluoroacetic acid (TFA) and 15 mL DCM overnight at room temperature, concentrated by rotary evaporator, precipitated in anhydrous diethyl ether, and redissolved in methanol. Ion-exchange resin (Amberlyst A26, OH-form) was added into it for complete neutralization. The residue was dissolved in water and lyophilized by freeze dryer to give product qTR-CB. (2.2 g, 54%) $^1$H NMR (D$_2$O, 400 MHz): δ 8.49 (s, 1H), 6.28 (dd, 2H), 5.82 (dd, 1H), 5.22 (s, 2H), 4.74 (s, 2H), 4.30 (s, 3H) (FIG. 14). $^{13}$C NMR (D$_2$O, 400 MHz): 170.0, 168.7, 140.6, 130.0, 128.9, 128.6, 55.6, 37.6, 32.1.

Example 15—Synthesis of TR-CB Monomer

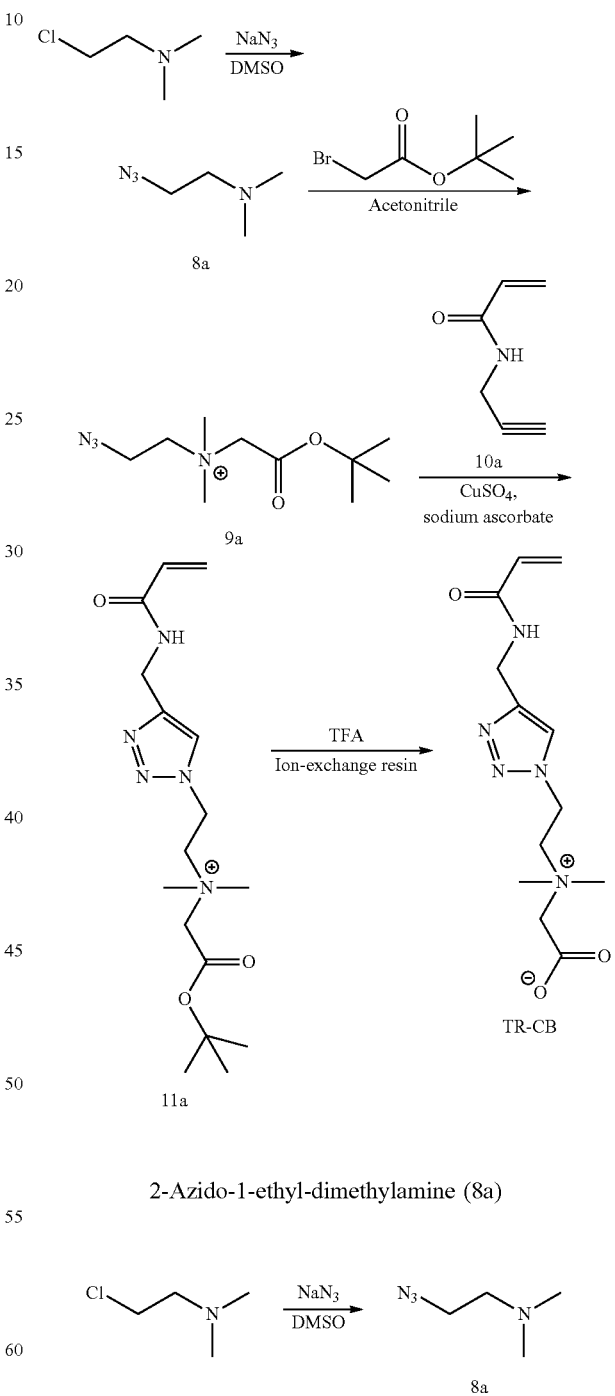

2-Azido-1-ethyl-dimethylamine (8a)

NaN$_3$ (13.7 g, 210 mmol) was added into a solution of 2-chloro-N,N-dimethylethylamine hydrochloride (10.0 g, 70 mmol) in 100 mL water and the reaction mixture was heated to 70° C. for overnight. The solution was basified with 4 M NaOH solution and extracted with anhydrous diethyl ether three times. The resulting solution was dried over MgSO4 and concentrated to give volatile colorless oil. (5.9 g, 74%) $^1$H NMR (CDCl$_3$, 400 MHz): δ 3.31 (t, 2H), 2.45 (t, 2H), 2.21 (s, 6H, N(CH$_3$)$_2$).

N-(2-Azidoethyl)-2-(tert-butoxy)-N,N-dimethyl-2-oxoethan-1-aminium (9a)

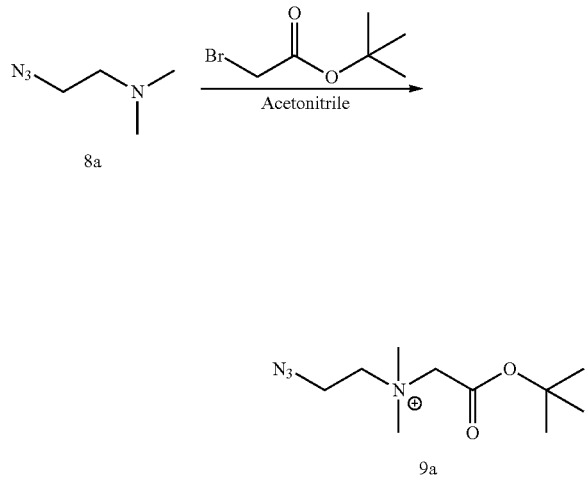

Figure 15:
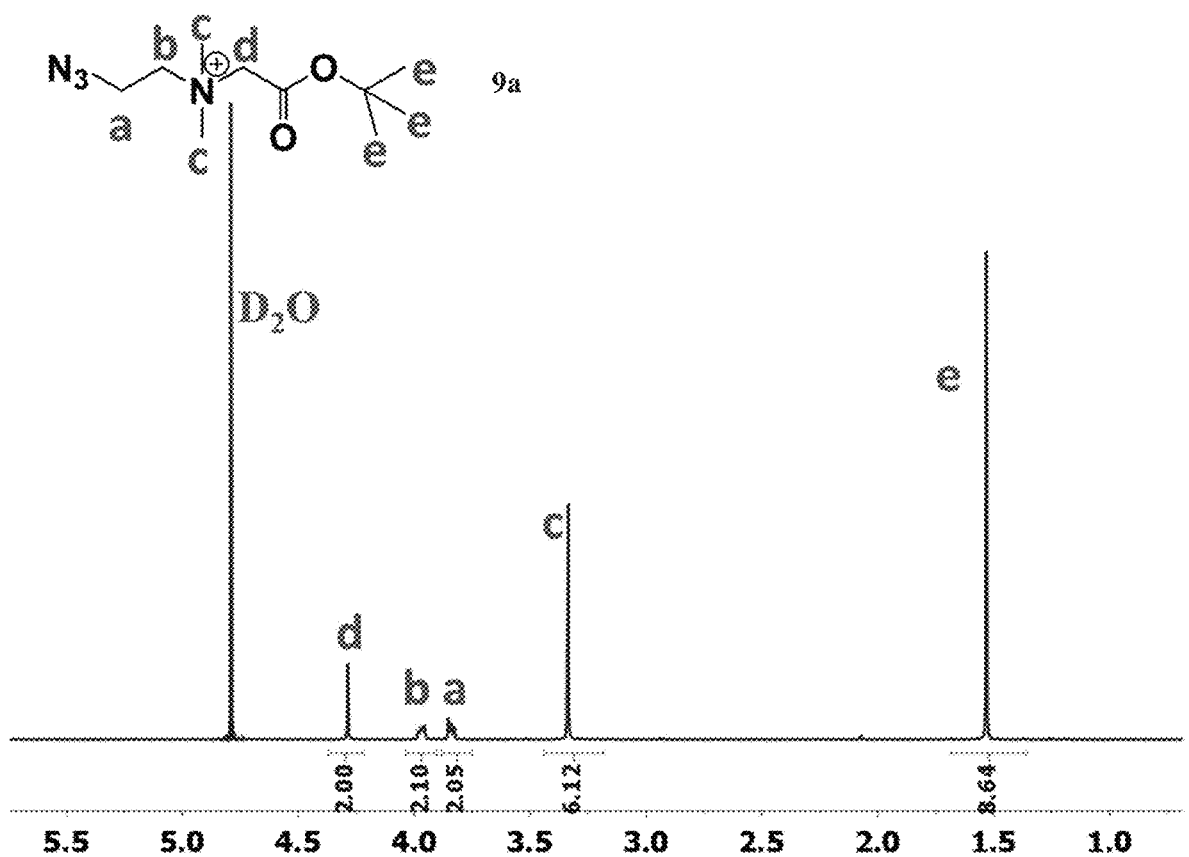
FIG. 15 shows $^1$H NMR spectrum of product 9a at 400 MHz, D$_2$O.

Product 8a (5.9 g, 52 mmol), tert-butyl bromoacetate (12.7 g, 65 mmol), and acetonitrile (100 mL) were added into a 250 mL round-bottom flask. The mixture was stirred under nitrogen atmosphere for 24 hours at 60° C. After reaction, the solvent was removed by rotary evaporator. The product 9a was precipitated by anhydrous diethyl ether and washed with anhydrous diethyl ether to get white powder (12.6, 79%). $^1$H NMR (D$_2$O, 400 MHz): δ 4.29 (s, 2H), 3.98 (t, 2H), 3.83 (t, 2H), 3.34 (s, 6H), 1.53 (s, 9H) (FIG. 15). $^{13}$C NMR (D$_2$O, 400 MHz): δ 164.0, 86.3, 62.6, 62.1, 52.9, 44.7, 27.2.

N-(2-(4-(Acrylamidomethyl)-1H-1,2,3-triazol-1-yl)ethyl)-2-(tert-butoxy)-N,N-dimethyl-2-oxoethan-1-aminium (11a)

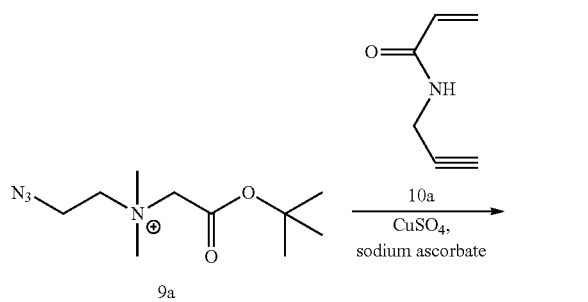

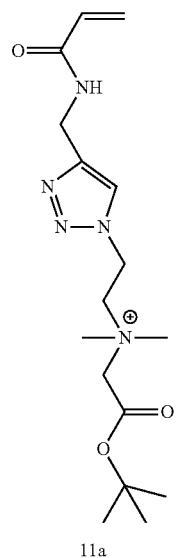

Figure 16:
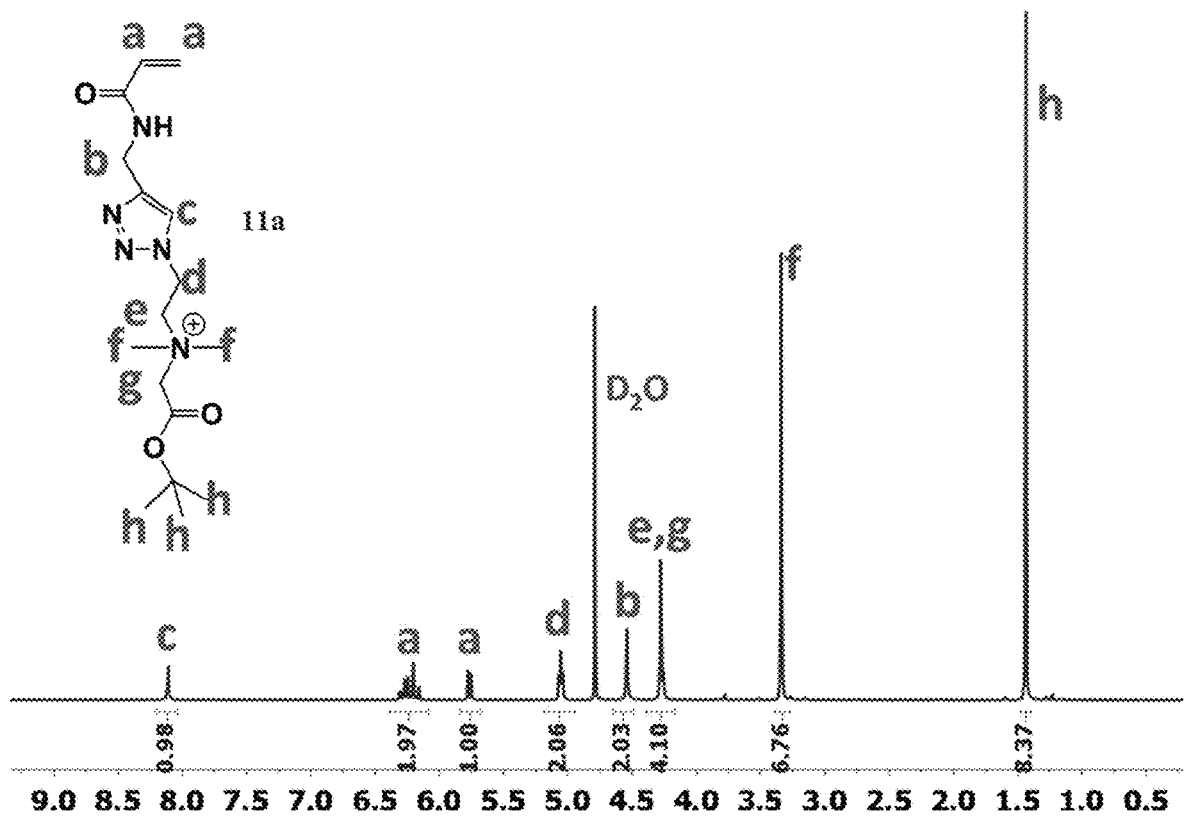
FIG. 16 shows $^1$H NMR spectrum of product 11a at 400 MHz, D$_2$O.

The mixture of product 10a (4.9 g, 45.1 mmol), product 9a (12.6 g, 41.0 mmol), sodium ascorbate (0.8 g, 4 mmol), CuSO4·5H2O (1.0 g, 4 mmol), and 100 mL methanol were added into a 250 mL round-bottom flask. The mixture was stirred under nitrogen atmosphere for 48 hours at 60° C. After the reaction, the solvent was removed by rotary evaporator and the crude product was precipitated by anhydrous diethyl ether. The product 1a (11.7 g, 68%) was further purified by silica gel column chromatography (eluent: methanol). $^1$H NMR (D$_2$O, 400 MHz): δ 8.11 (s, 1H), 6.24 (dd, 2H), 5.75 (dd, 1H), 5.07 (t, 2H), 4.58 (s, 2H), 4.28 (m, 4H), 3.34 (s, 6H), 1.44 (s, 9H) (FIG. 16). $^{13}$C NMR (D$_2$O, 400 MHz): 168.1, 163.3, 145.4, 129.3, 127.4, 124.7, 86.6, 62.3, 62.1, 52.7, 48.8, 44.0, 34.3, 27.1.

Triazole Carboxybetaine Acrylate (TR-CB)

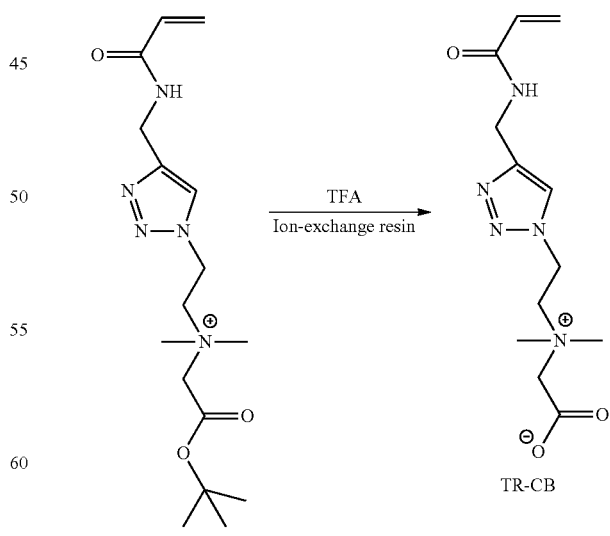

Figure 17:
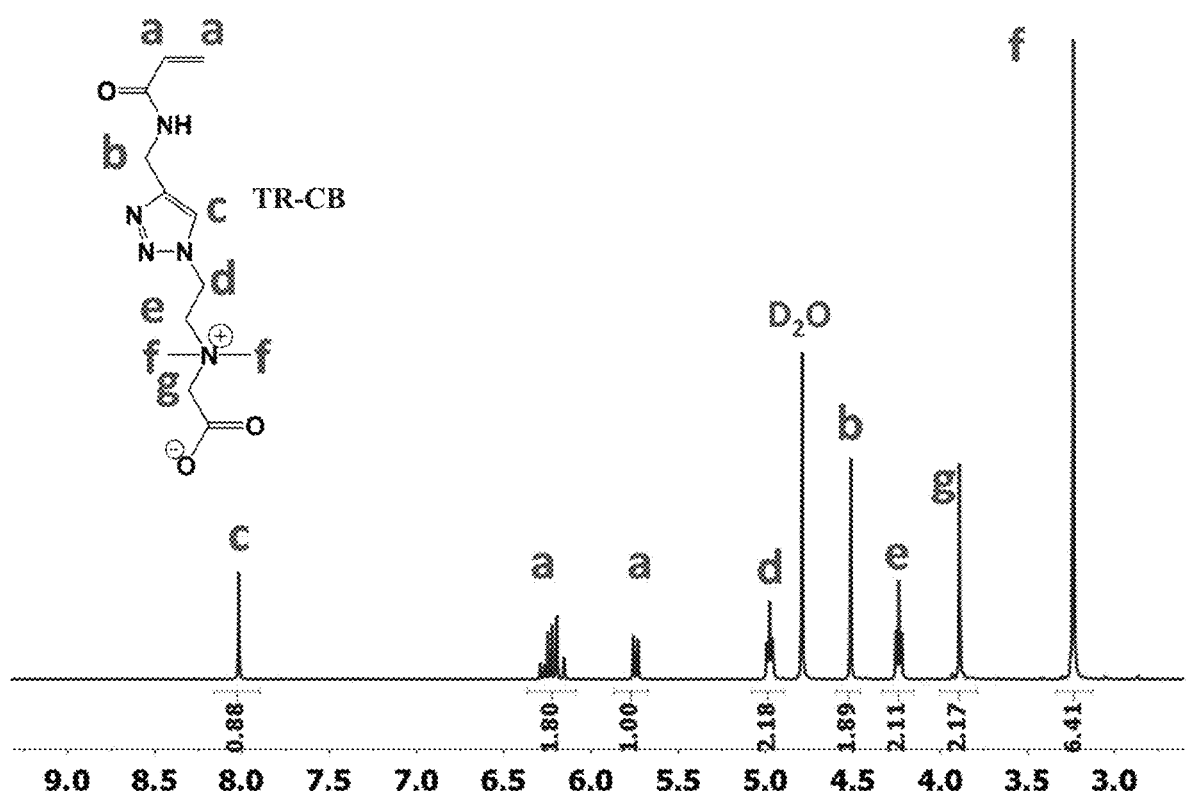
FIG. 17 shows $^1$H NMR spectrum of TR-CB at 400 MHz, D$_2$O.

The obtained product 11a (8.0 g) was treated with a mixture of 16 mL TFA and 16 mL DCM overnight at room temperature, concentrated with rotary evaporator, precipitated in anhydrous diethyl ether, and dissolved in methanol. Ion-exchange resin (Amberlyst A26, OH-form) was then added into it for complete neutralization. The resulting solution was added into neutral alumina column to remove residual copper ion. The product TR-CB (3.1 g, 57%) was collected after removing methanol solvent. $^1$H NMR (D$_2$O, 400 MHz): δ 8.02 (s, 1H), 6.22 (dd, 2H), 5.75 (dd, 1H), 4.98 (t, 2H), 4.51 (s, 2H), 4.24 (t, 2H), 3.89 (s, 2H), 3.24 (s, 6H) (FIG. 17). $^{13}$C NMR (D$_2$O, 400 MHz): 168.3, 168.1, 145.1, 129.5, 127.7, 124.2, 63.9, 61.3, 51.9, 44.0, 34.3.

Example 16—Synthesis of TR-SB Monomer

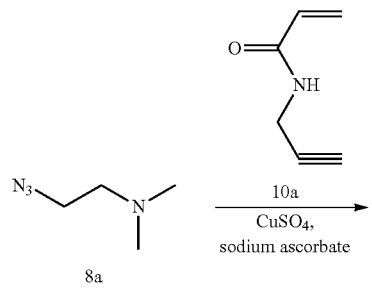

N-((1-(2-(Dimethylamino)ethyl)-1H-1,2,3-triazol-4-yl)methyl)acrylamide (12a)

Figure 18:
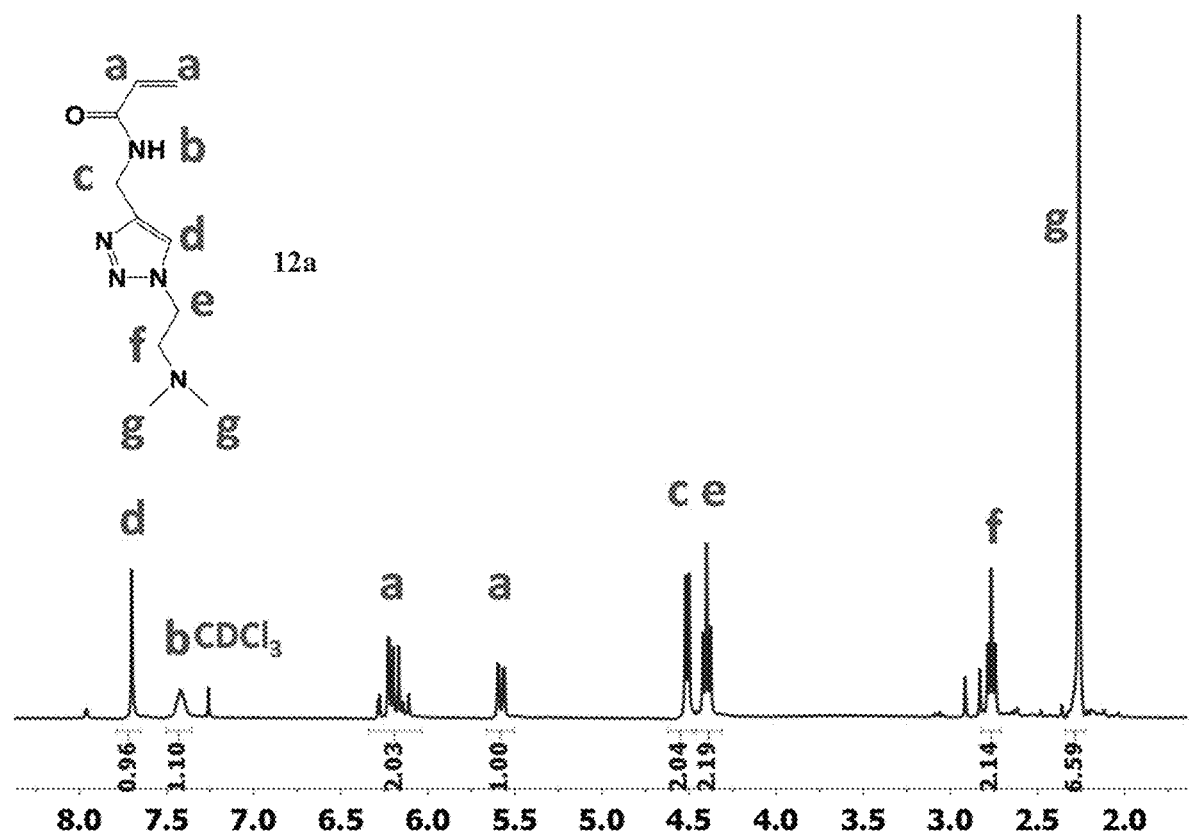
FIG. 18 shows $^1$H NMR spectrum of product 12a at 400 MHz, CDCl$_3$.

The mixture of product 10a (4.9 g, 45.1 mmol), product 8a (4.7 g, 40 mmol), sodium ascorbate (0.8 g, 4 mmol), CuSO4·5H2O (1.0 g, 4 mmol), and 100 mL methanol were added into a 250 mL round-bottom flask. The mixture was stirred under nitrogen atmosphere for 48 hours at 60° C. After the reaction, the solvent was removed by rotary evaporator. The product 12a (8.0 g, 78%) was further purified by silica gel column chromatography (eluent: ethyl acetate/methanol, 1:1, v/v). $^1$H NMR (CDCl$_3$, 400 MHz): δ 7.68 (s, 1H), 7.24 (s, 1H), 6.19 (dd, 2H), 5.60 (dd, 1H), 4.54 (m, 2H), 4.38 (m, 2H), 2.71 (m, 2H), 2.23 (s, 6H) (FIG. 18). $^{13}$C NMR (CDCl$_3$, 400 MHz): 165.6, 144.3, 130.6, 126.7, 122.9, 58.7, 48.2, 45.4, 34.8.

Triazole Sulfobetaine Acrylate (TR-SB)

Figure 19:
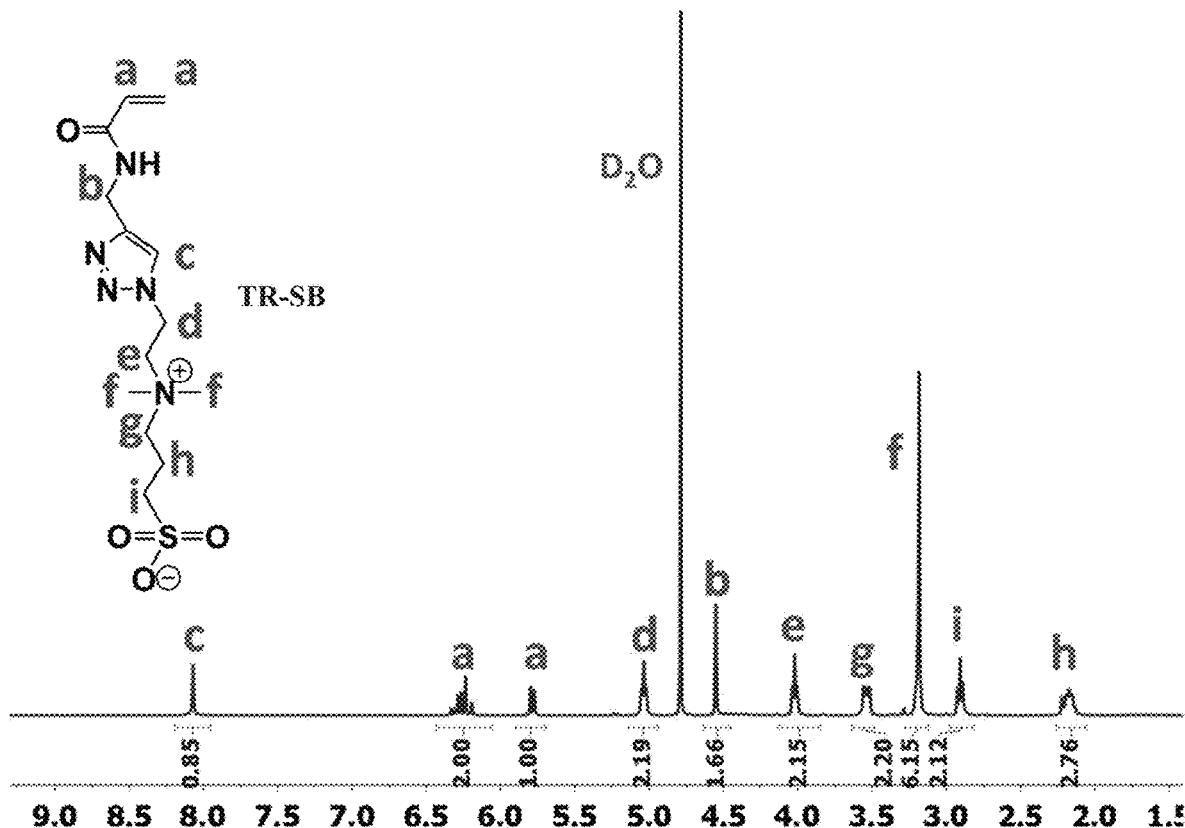
FIG. 19 shows $^1$H NMR spectrum of TR-SB at 400 MHz, D$_2$O.

Product 12a (4.5 g, 20 mmol) in 50 mL anhydrous acetone was stirred at room temperature. 1,3-Propanesultone (20 mmol, 2.4 g) was added dropwise into the solution. The reaction mixture was heated to 40° C. under nitrogen atmosphere for 6 hours. The precipitate was collected and washed with anhydrous acetone to get white powder (TR-SB) (2.8 g, 41%). $^1$H NMR (D$_2$O, 400 MHz): δ 8.06 (s, 1H), 6.26 (dd, 2H), 5.79 (dd, 1H), 5.02 (m, 2H), 4.55 (s, 2H), 4.01 (m, 2H), 3.53 (m, 2H), 3.17 (s, 6H), 2.90 (m, 2H), 2.18 (m, 2H) (FIG. 19). $^{13}$C NMR (D$_2$O, 400 MHz): 168.4, 145.2, 129.5, 127.7, 124.2, 63.0, 61.6, 51.1, 46.9, 43.7, 34.3, 18.1.

Results and Discussion of Examples 7-16

Figure 20A:
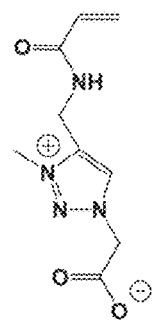
FIGS. 20A-20D show synthesis and characterization of the qTR-CB.
Figure 20B:
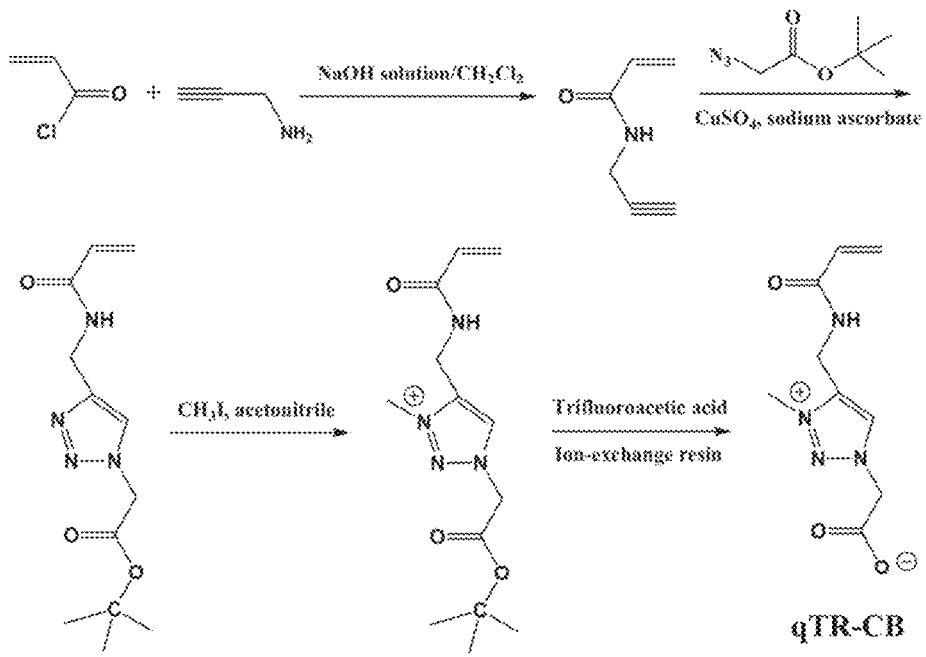

A new zwitterionic monomer qTR-CB was designed (FIG. 20A). This monomer includes a triazole moiety that plays a critical role in the anti-fibrotic properties of modified alginates and forms energy-dissipating π-π stacking. As shown in FIG. 20B, the synthesis of qTR-CB involved several steps. First, N-propargylacrylamide with dual reactive alkyne and vinyl groups was developed. Next, the alkyne group was then transformed into triazole group through Azide-Alkyne Huisgen Cycloaddition chemistry followed by a subsequent quaternization. Finally the qTR-CB monomer was obtained after removal of the protecting group of the carboxylic acid. The chemical structure of the qTR-CB monomer was confirmed by $^1$H NMR (FIG. 17) and $^{13}$C NMR.

Figure 20C:
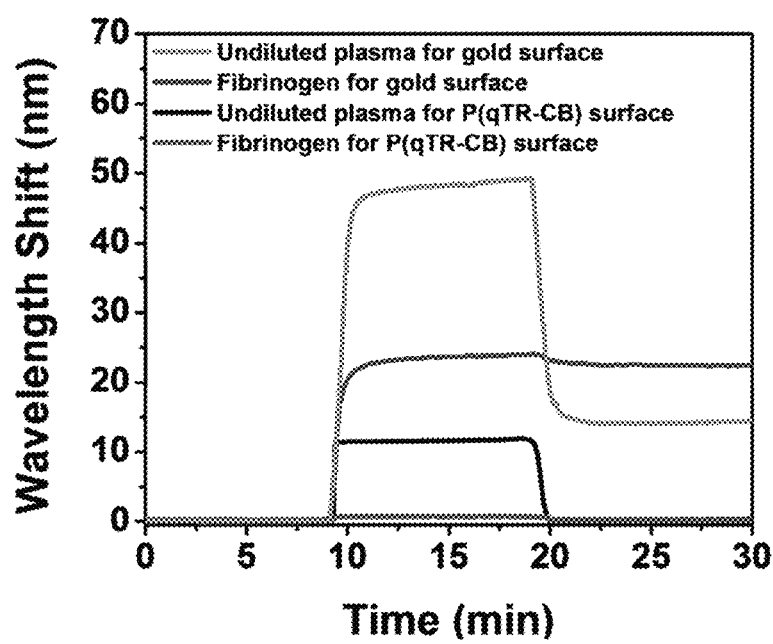
Figure 20D:
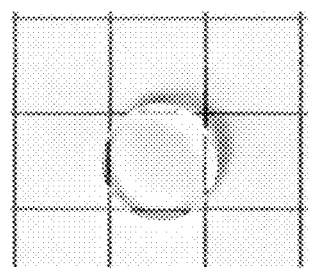

Non-specific protein adsorption on the implant surface is considered the initial, critical step in the foreign body response. To determine whether the qTR-CB was anti-biofouling and resistant to non-specific protein adsorption, a gold surface was grafted with P(qTR-CB) using a surface-initiated photoiniferter-mediated polymerization. The protein-resistance of P(qTR-CB) was evaluated via surface plasmon resonance (SPR) using a single protein solution and an undiluted human plasma. FIG. 20C shows the typical SPR sensorgrams of protein adsorption on the P(qTR-CB)-grafted and bare gold surfaces. From a 1 mg/mL fibrinogen (Fg) solution, the bare gold and P(qTR-CB)-grafted surfaces had adsorptions of 337.5±36.1 and 0.6±0.3 ng/cm$^2$, respectively. From undiluted human plasma, the protein adsorptions were 211.6±10.3 and 3.1±1.8 ng/cm$^2$ respectively for these two surfaces. Clearly, the P(qTR-CB)-grafted surface was highly resistant to non-specific protein adsorption, as compared to the bare gold surface. It should be noted that protein adsorption values on the P(qTR-CB)-grafted surfaces were well below the criteria for ultralow-fouling materials (less than 5 ng/cm$^2$ adsorbed fibrinogen). These data suggest that incorporation of triazole group did not change the zwitterionic or anti-fouling properties. The P(qTR-CB) hydrogel (FIG. 20D) was then prepared by crosslinking the qTR-CB monomer with a bifunctional zwitterionic carboxybetaine diacrylamide cross-linker (CBAAX) via a photo-initiated polymerization.

Figures 21A, 21B, 21C, 21D, 21E:
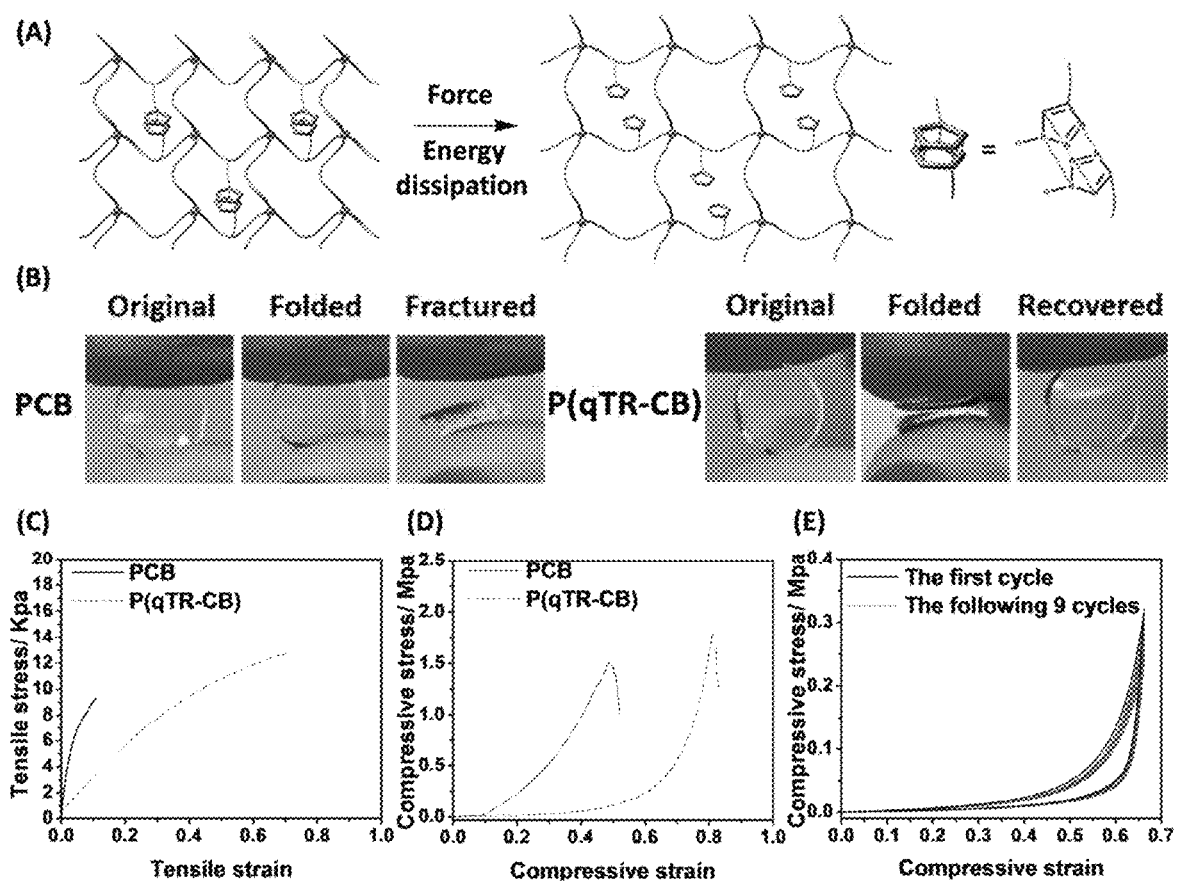
FIGS. 21A-21E show mechanical properties of the P(qTR-CB) hydrogel.

The P(qTR-CB) hydrogel was designed to address the mechanical property challenge faced by current zwitterionic hydrogels which are known to be relatively brittle or weak (Chin et al., "Additive Manufacturing of Hydrogel-Based Materials for Next-Generation Implantable Medical Devices," *Science Robotics* 2(2):eaah6451 (2017); Lynn et al., "Characterization of the in Vitro Macrophage Response and in Vivo Host Response to Poly (Ethylene Glycol)-Based Hydrogels," *Journal of Biomedical Materials Research Part A* 93(3):941-953 (2010), which are hereby incorporated by reference in their entirety). Robust mechanical properties are highly desirable for handling, implantation and any future clinical applications. The reversible π-π stacking between the triazole rings within the P(qTR-CB) hydrogel (FIG. 21A) dissipates energy under load and therefore make the hydrogel more resilient. To determine whether the incorporation of the triazole rings indeed improved the mechanical property, the P(qTR-CB) and conventional PCB hydrogels were compared in several mechanical tests. First, their fold-resistance property was qualitatively examined. As shown in FIG. 21B, the P(qTR-CB) hydrogel could be completely folded close to 180 degree without fracturing or any damage, and was even amenable to repeated folding. In contrast, the conventional PCB hydrogel fractured even with a small-angle folding. More quantitative tensile and compression tests were then performed. For the tensile test, the P(qTR-CB) hydrogel had a breaking strain close to 71% while the PCB hydrogel could only be stretched 11% (FIG. 21C). That represented a 6.5-fold increase in the breaking strain. For the compressive test (FIG. 21D), the P(qTR-CB) hydrogel sustained a 80% compression, while the PCB hydrogel could only be compressed 48%, which was in agreement with previous work (Merino et al., "Nanocomposite Hydrogels: 3D Polymer-Nanoparticle Synergies for On-Demand Drug Delivery," *ACS nano* 9(5):4686-4697 (2015), which is hereby incorporated by reference in its entirety). To further demonstrate the resilience of the P(qTR-CB) hydrogel, a compressive loading-unloading test was performed. As shown in FIG. 21E, the P(qTR-CB) hydrogel tolerated 65% compression for at least 10 cycles without any crack and maintained its original shape. The hysteresis loop observed in each cycle seemed to suggest that there was an energy dissipation mechanism probably due to the π-π stacking between the triazole groups, confirming the hypothesis.

Figure 22A:
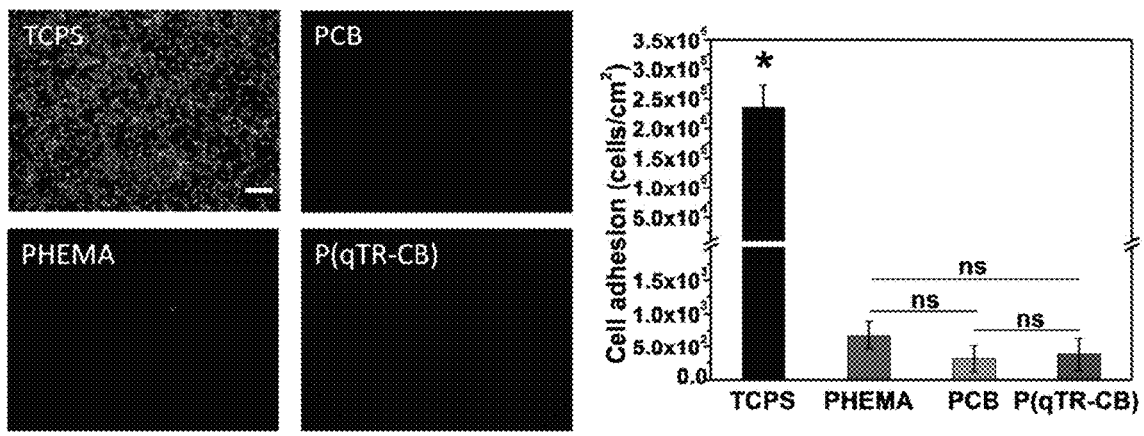
FIGS. 22A-22B show in vitro characterization of the P(qTR-CB) hydrogel.
Figure 22B:
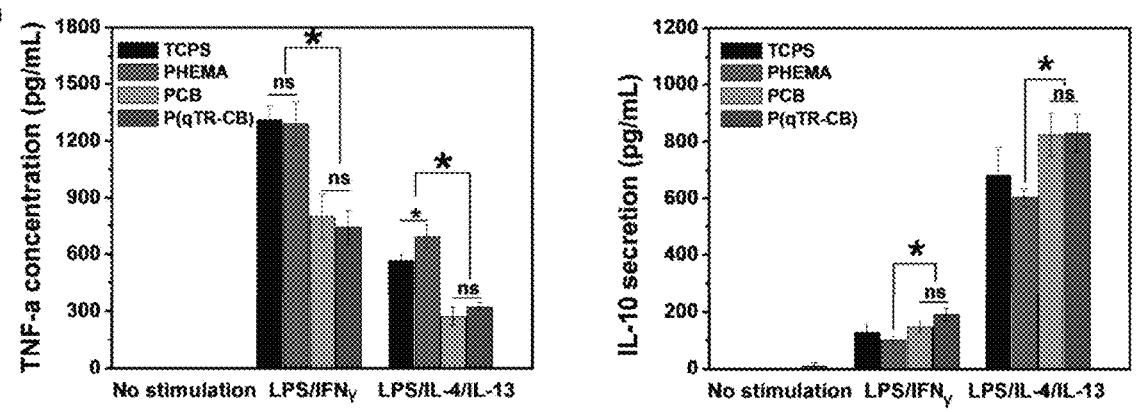

Next, cell attachment and macrophage activation on the P(qTR-CB) hydrogel was investigated in vitro. Hydrogels that resist cell attachment are desirable for many biomedical applications. Cell attachment on the P(qTR-CB) hydrogel was studied by culturing NIH/3T3 fibroblasts on its surface for three days. For comparison, PHEMA and PCB hydrogels as well as tissue culture polystyrene (TCPS) were used as controls. FIG. 22A showed that cells quickly attached, proliferated, and formed a confluent layer on the TCPS surfaces while there were almost no cells observed on the P(qTR-CB), PHEMA, and PCB hydrogel surfaces, suggesting that P(qTR-CB) hydrogel behaved similarly to PHEMA and PCB. The macrophage activation was then explored. Macrophages as a key component of the FBR regulate pro-inflammatory or pro-healing processes. Pro-inflammatory macrophages secrete inflammatory cytokines such as tumor necrosis factor-α (TNF-α) that triggers further recruitment and activation of inflammatory cells, while pro-healing macrophages produce anti-inflammatory cytokines such as interleukin (IL-10) that facilitates angiogenesis and tissue repair. Understanding how a biomaterial regulates macrophage phenotype is of importance to its biomedical applications. As shown in FIG. 22B, the levels of TNF-α and IL-10 secretion were almost undetectable for all the hydrogels without stimulation. With the stimulation of lipopolysaccharide/Interferon gamma (LPS/IFNγ) which was known to induce a pro-inflammatory macrophage phenotype, the cells on the PCB and P(qTR-CB) hydrogels secreted lower levels of TNF-α when compared to those cultured on the PHEMA hydrogel or the TCPS. With the stimulation of LPS/IL-4/IL-13 which was known to promote a pro-healing macrophage phenotype, the cells on PCB and P(qTR-CB) hydrogels had an enhanced IL-10 secretion when compared to those on the PHEMA hydrogel. Taken together, these results showed that P(qTR-CB) hydrogels inhibited inflammatory activation and promoted pro-healing macrophage phenotype.

Figures 23A, 23B, 23C, 23D, 23E:
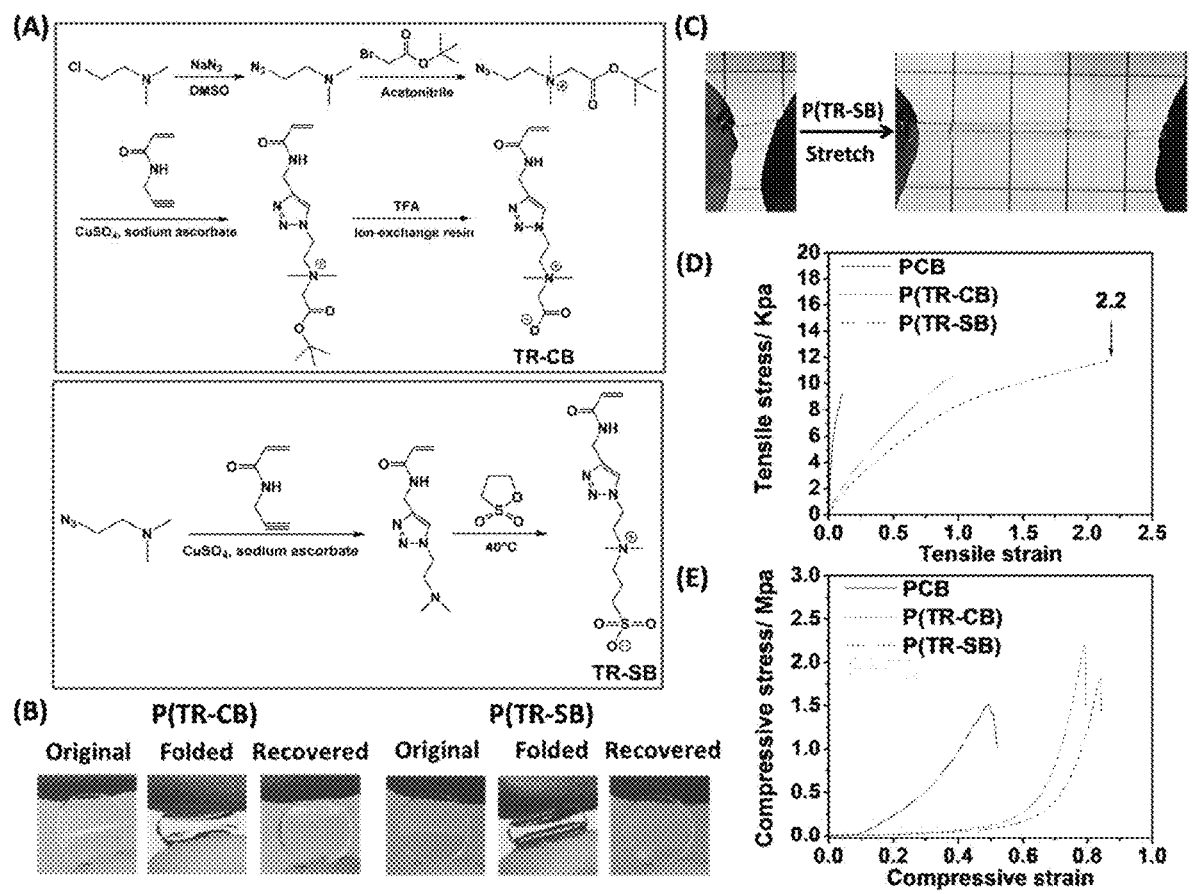
FIGS. 23A-23E show synthesis of P(TR-CB) and P(TR-SB) hydrogels and characterizations of their mechanical properties.
Figure 25:
FIG. 25 shows fluorescence microscopic images of NIH/3T3 cells attached after 3-days culturing on P(TR-CB) and P(TR-SB) hydrogel surfaces (Scale bars: 100 μm).

Encouraged by the results obtained from the P(qTR-CB), two more crosslinkable, triazole-containing zwitterionic monomers, TR-CB and TR-SB, were designed (FIG. 23A and FIG. 25). Hydrogels from these monomers were made and tested for FBR in mice. The synthetic routes for the TR-CB or TR-SB monomers are shown in FIG. 23A, and their chemical structures were confirmed by $^1$H NMR (FIGS. 17 and 19) and $^{13}$C NMR. Compared to the qTR-CB in which the triazole moiety was quaternized, the TR-CB and TR-SB monomers have an original, un-modified triazole group. The mechanical properties of the P(TR-CB) and P(TR-SB) hydrogels were evaluated. As shown in FIG. 23B, the P(TR-CB) and P(TR-SB) hydrogels could endure repeated folding, similar to that of P(qTR-CB) hydrogels. Both hydrogels were highly resilient (FIG. 23C-23E). Especially for the P(TR-SB) hydrogel (FIG. 23C-23D), the tensile strain was as high as 218%, while the maximum tensile strain for zwitterionic hydrogels reported to date is only 65% (Lynn et al., "Characterization of the in Vitro Macrophage Response and in Vivo Host Response to Poly (Ethylene Glycol)-Based Hydrogels," *Journal of Biomedical Materials Research Part A* 93(3):941-953 (2010), which is hereby incorporated by reference in its entirety). This is a drastic improvement in the field of zwitterionic hydrogels. When compared to PCB hydrogel, the breaking strains of P(TR-CB) and P(TR-SB) hydrogels were 9-fold and 20-fold higher, respectively. It should be also noted that P(TR-CB) and P(TR-SB) hydrogels were more elastic than the P(qTR-CB). This may be attributed to the position of the positive charge on the qTR-CB triazole ring. The electrostatic repulsion between the charges may attenuate the π-π stacking interaction. For compressive tests (FIG. 23E), both the P(TR-CB) and P(TR-SB) hydrogels had high compressive strains (79% and 83%, respectively). These TR-ZW hydrogels represent a first class of zwitterionic hydrogel with robust mechanical properties.

Figure 24A:
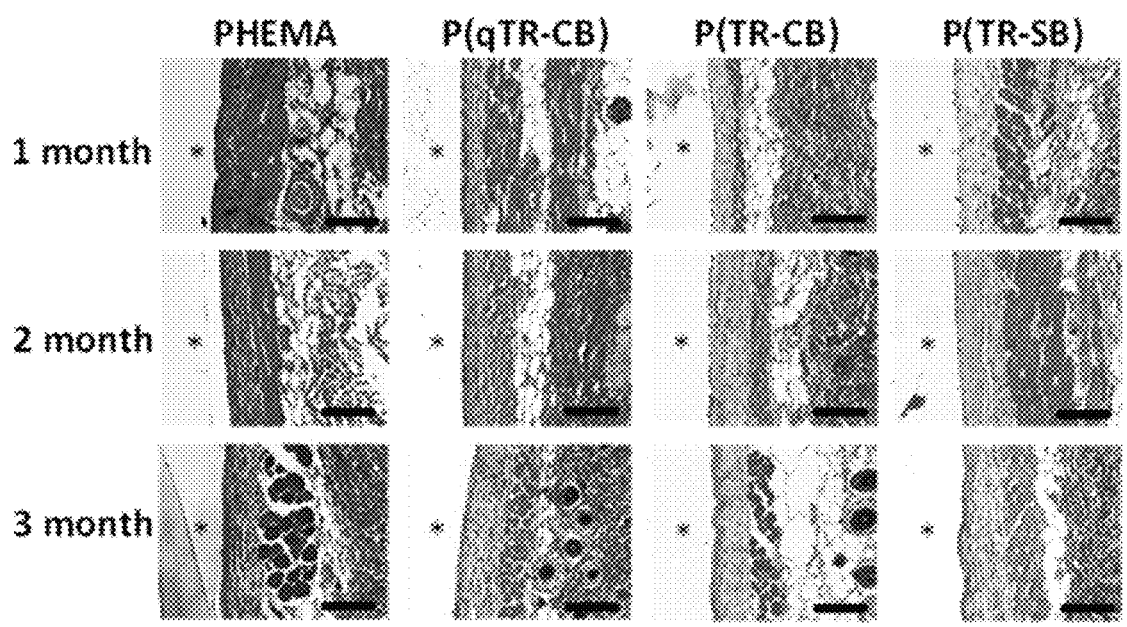
FIGS. 24A-24B show characterization of the foreign body response (FBR) to various hydrogels in immunocompetent mice.
Figure 24B:
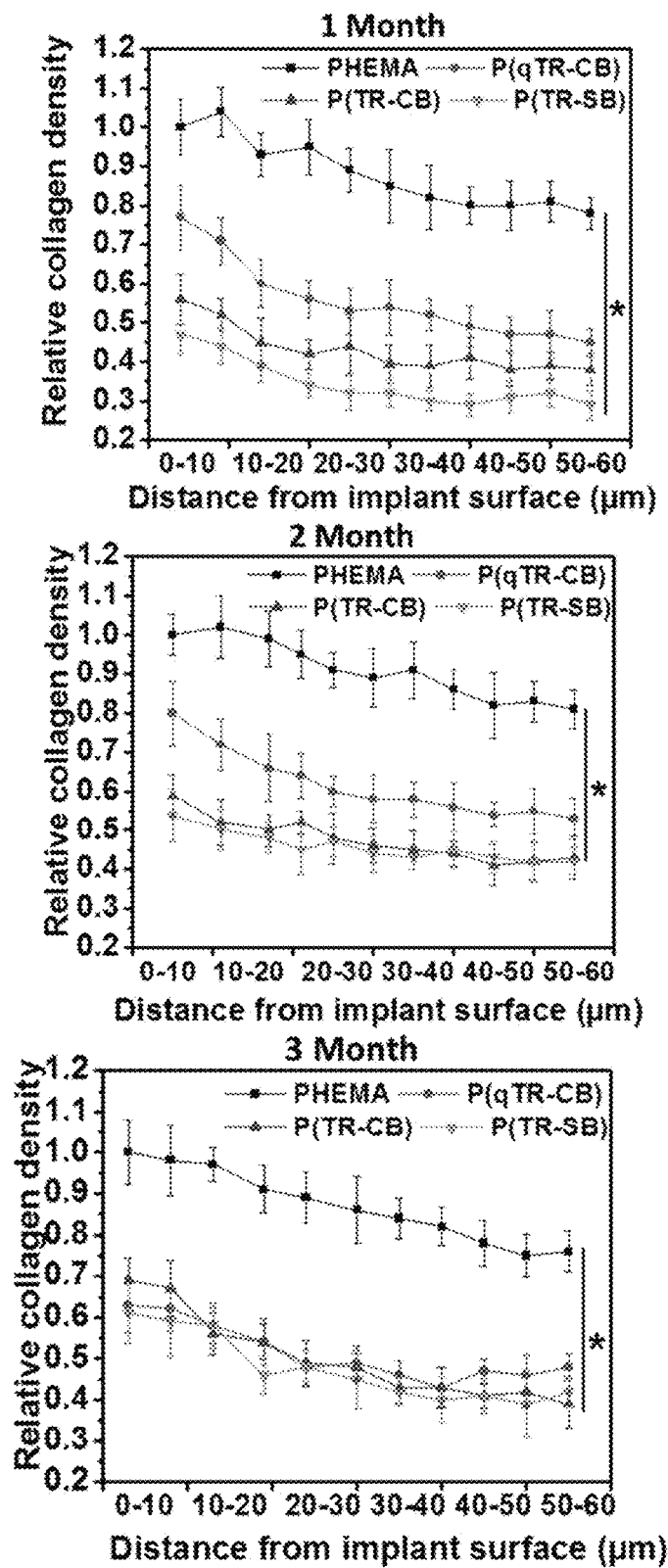

To investigate whether these new TR-ZW hydrogels (P(qTR-CB), P(TR-CB), and P(TR-SB)) had FBR-resistant properties, they were subcutaneously implanted in immunocompetent C57BL/6 mice. To date, the FBR is still a major concern for the performance and longevity of implanted materials and devices. There is a critical need for development of novel materials that mitigate FBR and are mechanically robust. In the present application, the FBR to the implants at selected time points post implantation (1, 2, and 3 months) were evaluated. A commonly used PHEMA hydrogel was chosen as control. At each time point, the hydrogel samples were retrieved and examined the FBR including the fibrosis around the implants using Masson's trichrome staining as well as the blood vessel formation using CD31 staining. At 1 month, it was observed that all TR-ZW hydrogels had loose collagen layers around them as indicated by the light blue color (FIG. 24A), while the PHEMA hydrogels had a much denser collagen deposition. The P(TR-SB) hydrogel had a particularly low density collagen deposition. The loose collagen deposition has been thought to affect less the mass transfer between the body and implant and therefore is desirable in many applications. Longer-term implantation experiments (i.e. 2 and 3 months) revealed similar results. The collagen density at the interface between the TR-ZW hydrogels and tissues was significantly lower when compared to the case of PHEMA control (FIG. 24B).

Figures 26A, 26B:
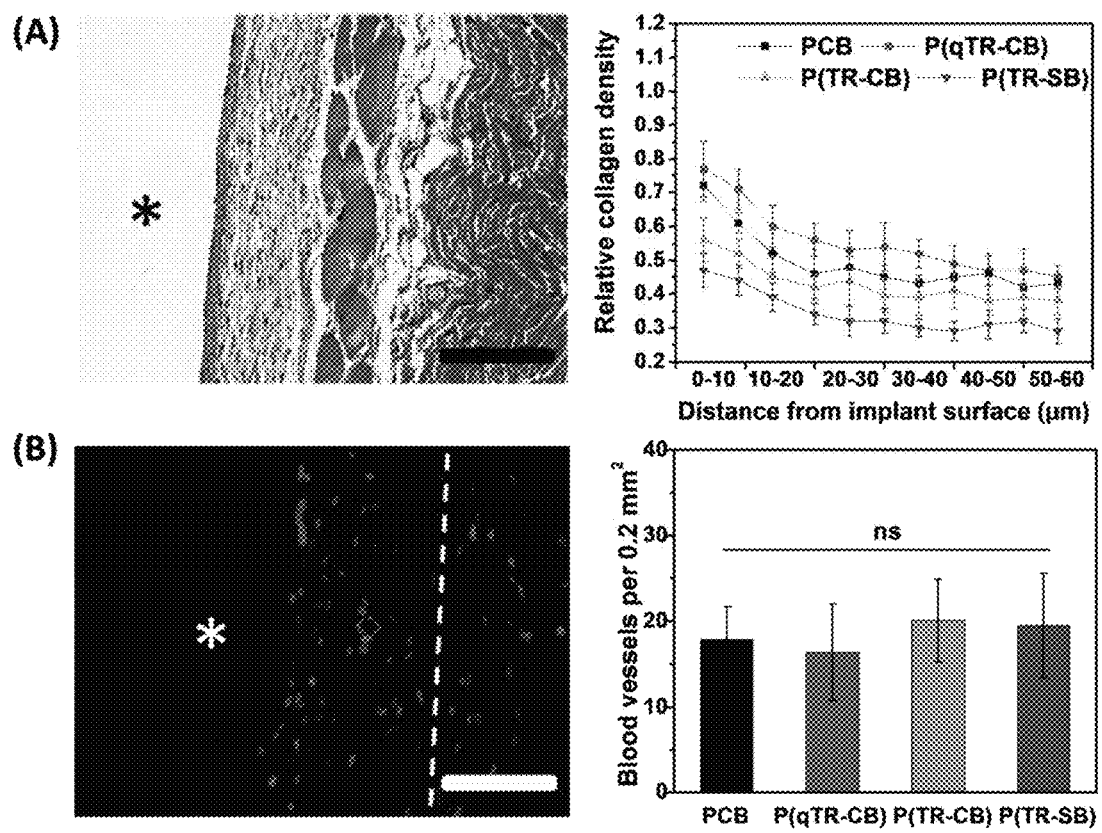
FIG. 26A-26B show characterization of FBR to various hydrogels in immunocompetent mice after 1 month subcutaneous implantation.

When comparing the TR-ZW hydrogels with the previously reported PCB hydrogels (Jiang et al., "Click Hydrogels, Microgels and Nanogels: Emerging Platforms for Drug Delivery and Tissue Engineering," *Biomaterials* 35(18): 4969-4985 (2014); Lee et al., "Light-Triggered in Vivo Activation of Adhesive Peptides Regulates Cell Adhesion, Inflammation and Vascularization of Biomaterials," *Nature Materials* 14(3):352-360 (2015), which are hereby incorporated by reference in their entirety), it was found that the density of collagen deposition and the number of blood vessels for the TR-ZW hydrogels were comparable to or even better than those for the PCB (Jiang et al., "Click Hydrogels, Microgels and Nanogels: Emerging Platforms for Drug Delivery and Tissue Engineering," *Biomaterials* 35(18):4969-4985 (2014), which is hereby incorporated by reference in its entirety) (FIGS. 26A-26B). It is generally held that the antifouling property or biocompatibility is compromised if hydrophobic moiety is incorporated into zwitterionic materials. The triazole group as a hydrophobic moiety indeed affected its antifouling property. For example, the amount of plasma adsorption for P(qTR-CB), P(TR-CB), and P(TR-SB) surfaces was 3.1±1.8, 6.4±2.5, and 10.9±3.2 ng/cm2, respectively (Table 1) while PCB surface was reported to only adsorb <0.3 ng/cm2 protein from plasma. However, the in vivo biocompatibility or the FBR-resistant property of the TR-ZW hydrogels was not affected. The triazole group plays a role here in mitigating the fibrotic response in addition to the zwitterionic moiety. Chemically modified alginates containing triazole groups were reported to be capable of mitigating the fibrotic response effectively (Desai et al., "Versatile Click Alginate Hydrogels Crosslinked via Tetrazine-Norbornene Chemistry," *Biomaterials* 50:30-37 (2015), which is hereby incorporated by reference in its entirety). The FBR-resistant property of the TR-ZW hydrogels was also consistent with the macrophage activation data (FIG. 22B). Thus, a new class of hydrogels was developed that exhibited similar FBR-resistant properties but were much more mechanically robust than the zwitterionic hydrogels developed to date.

TABLE 1

Protein Adsorption (Undiluted human plasma) Measured by SPR

| | Surface | | | |
|---|---|---|---|---|
| | Bare gold | P(qTR-CB) | P(TR-CB) | P(TR-SB) |
| Surface mass (ng/cm$^2$) | 211.6 ± 10.3 | 3.1 ± 1.8 | 6.4 ± 2.5 | 10.9 ± 3.2 |

Average values and standard deviations of three measurements.

In summary, a new class of triazole-zwitterionic hydrogels that is mechanically robust and FBR-resistant have been designed and synthesized. Compared to conventional zwitterionic hydrogels which are typically weak or brittle, these novel TR-ZW hydrogels exhibited high resilience including higher stretchability and better compression-resistance or folding-resistance. They retained antifouling characteristics, expected for zwitterionic materials. More importantly, upon subcutaneous implantation in immunocompetent mice, the TR-ZW hydrogels mitigated the fibrosis and promoted the blood vessel formation. The combination of mechanical and FBR-resistant properties is highly desirable for many biomedical applications such as cell encapsulation and implant modifications, both of which require material stability and integration with the body for the long-term function and performance.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A monomer of Formula (III):

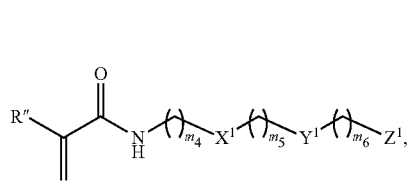

wherein $X^1$ is absent or is

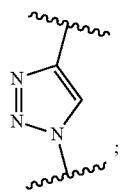

$Y^1$ is

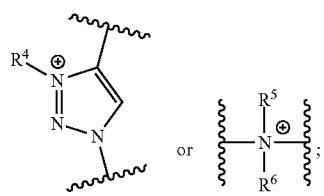

$Z^1$ is

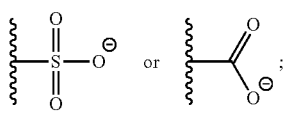

$m_4$ is 1 to 50;
$m_5$ is 0 to 10;
$m_6$ is 1 to 50;
R″ is H or $C_{1-6}$ alkyl;
$R_4$ is $C_{1-20}$ alkyl;
$R_5$ is $C_{1-20}$ alkyl; and
$R_6$ is $C_{1-20}$ alkyl,
with the proviso that when $X^1$ is absent, $Y^1$ is not

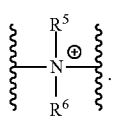

2. The monomer of claim 1, which has Formula (IIIa):

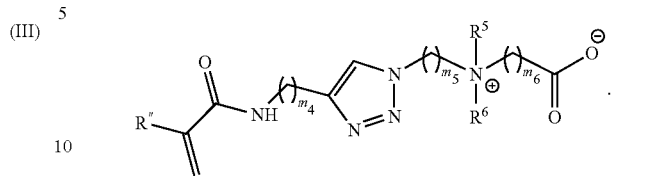

3. The monomer of claim 1, which has Formula (IIIb):

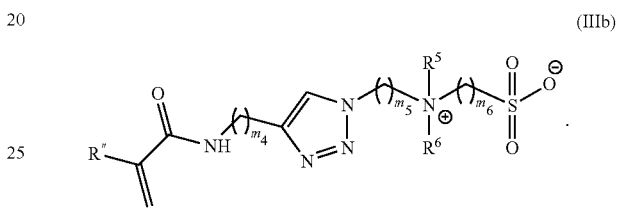

4. The monomer of claim 1, which has Formula (IIIc):

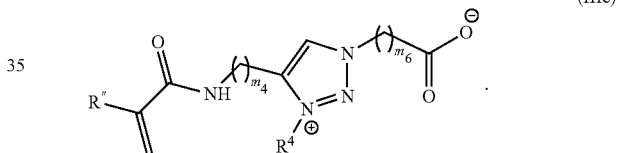
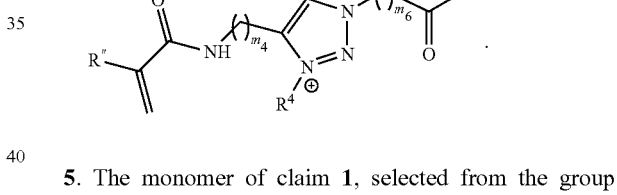

5. The monomer of claim 1, selected from the group consisting of:

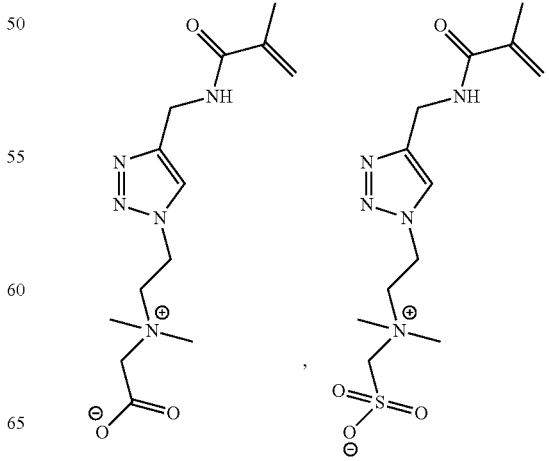

-continued

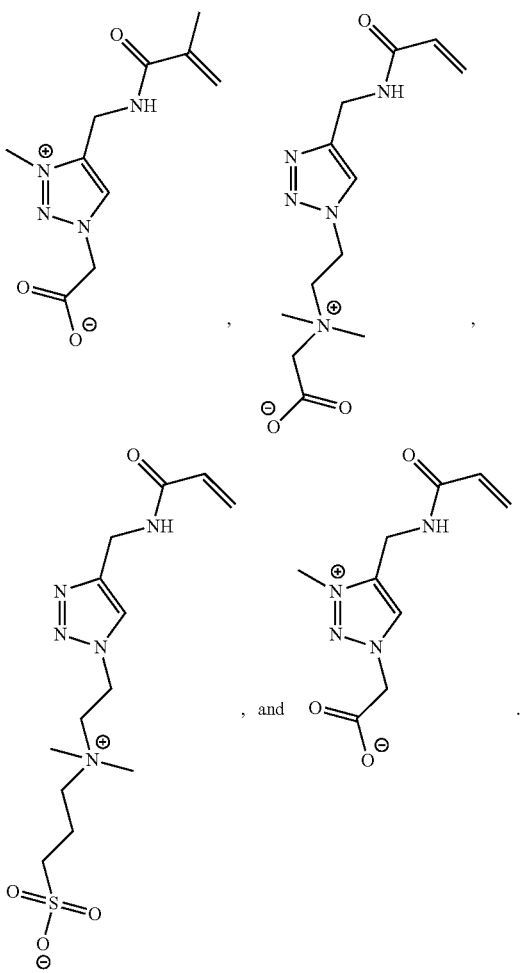
, , , and .

6. A polymeric network comprising crosslinked monomers of Formula (III):

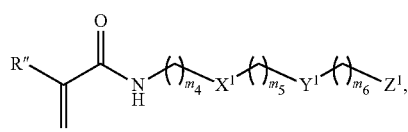
(III)

wherein $X^1$ is absent or is

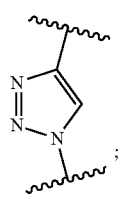
;

$Y^1$ is

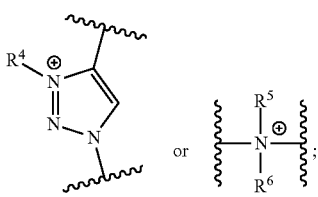
or ;

$Z^1$ is

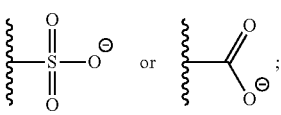
or ;

$m_4$ is 1 to 50;
$m_5$ is 0 to 10;
$m_6$ is 1 to 50;
$R''$ is H or $C_{1-6}$ alkyl;
$R^4$ is $C_{1-20}$ alkyl;
$R^5$ is $C_{1-20}$ alkyl; and
$R^6$ is $C_{1-20}$ alkyl, with the proviso that when $X^1$ is absent, $Y^1$ is not

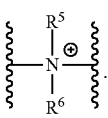
.

7. The polymeric network of claim 6, wherein the cross-linked monomers of the network are the same.

8. The polymeric network of claim 6, wherein the cross-linked monomers of the network are different.

9. The polymeric network of claim 6, wherein the monomers are cross-linked with a carboxybetaine diacrylamide cross-linker (CBAAX).

10. A hydrogel comprising the polymeric network of claim 6.

11. A capsule comprising:
the hydrogel of claim 10 and
a therapeutic agent encapsulated in said hydrogel.

12. The capsule of claim 11, wherein said therapeutic agent comprises a preparation of cells.

13. The capsule of claim 11 further comprising:
a preparation of cells encapsulated in the hydrogel, wherein the therapeutic agent is an agent that is released from the preparation of cells.

14. The capsule of claim 13, wherein the preparation of cells comprises a preparation of islets.

15. The capsule of claim 11, wherein the therapeutic agent is selected from the group consisting of a therapeutic protein, peptide, antibody or binding fragment thereof, antibody mimetic, nucleic acid, small molecule, hormone, growth factor, angiogenic factor, cytokine, anti-inflammatory agents, and any combination thereof.

16. A method of delivering a therapeutic agent to a subject, said method comprising:
administering the capsule according to claim 11 to the subject.

17. The method of claim 16, wherein said administering comprising:
implanting the capsule into the subject.

18. A method of treating a diabetic subject, said method comprising:
   implanting the capsule according to claim 14 into a subject with diabetes.

* * * * *